US009155743B2

(12) United States Patent
Buck et al.

(10) Patent No.: US 9,155,743 B2
(45) Date of Patent: Oct. 13, 2015

(54) BICYCLIC HETEROCYCLE COMPOUNDS AND THEIR USES IN THERAPY

(75) Inventors: Ildiko Maria Buck, Cambridge (GB); Gianni Chessari, Cambridge (GB); Steven Howard, Cambridge (GB); David Charles Rees, Cambridge (GB); Alison Jo-Anne Woolford, Cambridge (GB)

(73) Assignee: ASTEX THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 14/112,581

(22) PCT Filed: Apr. 20, 2012

(86) PCT No.: PCT/GB2012/050866
§ 371 (c)(1),
(2), (4) Date: Oct. 18, 2013

(87) PCT Pub. No.: WO2012/143725
PCT Pub. Date: Oct. 26, 2012

(65) Prior Publication Data
US 2014/0045831 A1    Feb. 13, 2014

Related U.S. Application Data

(60) Provisional application No. 61/477,718, filed on Apr. 21, 2011.

(30) Foreign Application Priority Data

Apr. 21, 2011    (GB) .................................. 1106814.5

(51) Int. Cl.
| | | |
|---|---|---|
| *C07D 498/10* | (2006.01) | |
| *A61K 31/5365* | (2006.01) | |
| *A61K 31/5386* | (2006.01) | |
| *C07D 471/04* | (2006.01) | |
| *C07D 498/04* | (2006.01) | |
| *A61K 45/06* | (2006.01) | |
| *A61K 31/519* | (2006.01) | |
| *A61K 31/437* | (2006.01) | |
| *A61K 31/4985* | (2006.01) | |
| *A61K 31/5383* | (2006.01) | |

(52) U.S. Cl.
CPC ........... *A61K 31/5386* (2013.01); *A61K 31/437* (2013.01); *A61K 31/4985* (2013.01); *A61K 31/519* (2013.01); *A61K 31/5383* (2013.01); *A61K 45/06* (2013.01); *C07D 471/04* (2013.01); *C07D 498/04* (2013.01); *C07D 498/10* (2013.01)

(58) Field of Classification Search
CPC .......................... C07D 498/04; A61K 31/5365
USPC ........................................ 514/230.5; 544/105
See application file for complete search history.

(56) References Cited

U.S. PATENT DOCUMENTS

| | | |
|---|---|---|
| 8,314,094 B2 | 11/2012 | Ishikawa et al. |
| 8,394,792 B2 | 3/2013 | Ahn et al. |
| 2014/0045831 A1 | 2/2014 | Buck et al. |
| 2014/0179666 A1 | 6/2014 | Woolford et al. |

FOREIGN PATENT DOCUMENTS

| | | |
|---|---|---|
| JP | 2004/123649 | 4/2004 |
| WO | 02/44183 A2 | 6/2002 |
| WO | 2004/006906 A2 | 1/2004 |
| WO | 2005/011601 A2 | 2/2005 |
| WO | 2006/024834 A1 | 3/2006 |
| WO | 2006/134378 A1 | 12/2006 |
| WO | 2007/051119 A1 | 5/2007 |
| WO | 2008/073306 A1 | 6/2008 |
| WO | 2008/153947 A2 | 12/2008 |
| WO | 2012/143725 A1 | 10/2012 |
| WO | 2012/143726 A1 | 10/2012 |
| WO | 2014/060767 A1 | 4/2014 |
| WO | 2014/060768 A1 | 4/2014 |
| WO | 2014/060770 A1 | 4/2014 |

OTHER PUBLICATIONS

Flygare, J., et al., "Small-molecule pan-IAP antagonists: a patent review", Expert Opinion on Therapeutic Patents, Informa Healthcare, GB, vol. 20 (2), pp. 251-267 (2010).
Park, C., et al., "Non-peptidic Small Molecule Inhibitors of XIAP", Bioorganic & Medicinal Chemistry Letters, vol. 15(3), pp. 771-775 (2005).
Search Report for GB1106814.5 dated Jul. 25, 2011.
International Search Report for PCT/GB2012/050866 dated Jun. 18, 2012.

*Primary Examiner* — Kahsay Habte
(74) *Attorney, Agent, or Firm* — Heslin Rothenberg Farley & Mesiti P.C.

(57) ABSTRACT

The invention relates to bicyclic heterocycle compounds of formula (I): or tautomeric or stereochemically isomeric forms, N-oxides, pharmaceutically acceptable salts or the solvates thereof; wherein $R^1$, $R^2$, $R^3$, A, W, U and V are as defined herein; to pharmaceutical compositions comprising said compounds and to the use of said compounds in the treatment of diseases, e.g. cancer.

18 Claims, No Drawings

BICYCLIC HETEROCYCLE COMPOUNDS AND THEIR USES IN THERAPY

CROSS REFERENCE TO RELATED APPLICATIONS

This application is a national stage filing under section 371 of International Application No. PCT/GB2012/050866, filed on Apr. 20, 2012, and published in English on Oct. 26, 2012 as WO/2012/143725, and claims priority to British Application No. 1106814.5 filed on Apr. 21, 2011, and to U.S. Provisional Application No. 61/477,718, filed on Apr. 21, 2011. The entire disclosures of each of the prior applications are hereby incorporated herein by reference.

RELATED APPLICATIONS

This application is related to: U.S. provisional patent application No. 61/477,718 filed 21 Apr. 2011 and United Kingdom patent application number 1106814.5 filed 21 Apr. 2011, the contents of both of which are incorporated herein by reference in their entirety.

FIELD OF THE INVENTION

The invention relates to new bicyclic compounds, to pharmaceutical compositions comprising said compounds and to the use of said compounds in the treatment of diseases, e.g. cancer.

BACKGROUND OF THE INVENTION

IAP Family

The family of inhibitor of apoptosis (IAP) proteins comprises 8 members, XIAP, cIAP1, cIAP2, NAIP, ILP2, ML-IAP, survivin and BRUCE (also known as apollon). Members of the IAP family have been shown to inhibit programmed cell death through their ability to directly inhibit members of the caspase family of apoptotic enzymes, although the precise role of all 8 members is yet to be fully defined. The common structural feature of all IAP family members is a ~70 amino acid zinc-binding fold termed the baculovirus IAP repeat (BIR) domain, which is present in one to three copies.

Many interactions between IAPs and other proteins are mediated via a surface groove on the BIR domain. BIR domains may be classified by their peptide-binding specificity. There are three types of BIR domains; type III domains (capable of binding caspase (and caspase-like) peptides with a specificity for proline in the third (P3) position (e.g. XIAP BIR3), type II domains (like type III domains but lacking the proline requirement e.g. XIAP BIR2) and type I domains (which do not bind caspases or similar peptides, e.g. XIAP BIR1) (Eckelman et al. Cell Death and Differentiation 2008; 15: 920-928). BIRs are small (~70 amino acids) Zn-coordinated domains and a variety of proteins use their N-terminal to interact with the BIR domains grooves. BIR antagonists prevent caspases binding to BIRs and hence result in increased caspase activity thereby inducing auto-ubiquitination and proteasomal degradation of IAPs.

IAPs are overexpressed in many cancers including renal, melanoma, colon, lung, breast, ovarian and prostate cancers (Tamm et al., Clin. Cancer Research 2000; 6(5): 1796-803), and have been implicated in tumour growth, pathogenesis and resistance to chemo- and radio-therapy (Tamm 2000).

XIAP

XIAP is a 57 kDa protein with three BIR domains, the second and third of which bind caspases and a RING-type zinc finger (E3 ligase). XIAP binds several proteins in addition to caspases, including ligation substrates such as TAK1 and cofactor TAB1, MURR1 involved in copper homeostasis (Burstein et al., EMBO 2004; 23: 244-254), endogenous inhibitors such as second mitochondria-derived activator of caspases (SMAC), and those of less clear function such as MAGE-D1, NRAGE (Jordan et al., J. Biol. Chem. 2001; 276: 39985-39989). The BIR3 domain binds and inhibits caspase-9, an apical caspase in the mitochondrial pathway of caspase activation. A groove on the surface of the BIR3 domain interacts with the N-terminus of the small subunit of caspase-9, locking capsase-9 in its inactive monomeric form with an incompetent catalytic site (Shiozaki et al., Mol. Cell 2003; 11: 519-527).

In addition to caspase-binding, XIAP also inhibits apoptosis through other mechanisms. XIAP forms a complex with TAK1 kinase and its cofactor TAB1 that leads to activation of JNK and MAPK signal transduction pathways, in turn leading to activation of NFκB (Sanna et al., Mol Cell Biol 2002; 22: 1754-1766). XIAP also activates NFκB by promoting NFκB translocation to the nucleus and degradation of IκB (Hofer-Warbinek et al., J. Biol. Chem. 2000; 275: 22064-22068, Levkau et al., Circ. Res. 2001; 88: 282-290). Cells transfected with XIAP are able to block programmed cell death in response to a variety of apoptotic stimuli (Duckett et al., EMBO 1996; 15: 2685-2694, Duckett et al., MCB 1998; 18: 608-615, Bratton, Lewis, Butterworth, Duckett and Cohen, Cell Death and Differentiation 2002; 9: 881-892).

XIAP is ubiquitously expressed in all normal tissues, but it is pathologically elevated in many acute and chronic leukaemias, prostate, lung, renal, and other types of tumours (Byrd et al., 2002; Ferreira et al., 2001; Hofmann et al., 2002; Krajewska et al., 2003; Schimmer et al., 2003; Tamm et al., 2000). In de novo acute myeloid leukaemia (AML), XIAP expression correlates with myelomonocytic French-American-British (FAB) subtypes M4/M5 ($P<0.05$) and expression of monocytic markers in AML blasts. In addition, XIAP was found to be overexpressed in normal monocytes but undetectable in granulocytes. In AML, XIAP expression was significantly lower in patients with favourable rather than intermediate or poor cytogenetics (n=74; $P<0.05$) (Tamm et al., Hematol. J. 2004; 5(6): 489-95). Overexpression renders cells resistant to multi-agent therapy and is associated with poor clinical outcome in disease including AML, renal cancer, melanoma (Tamm et al., Clin. Cancer Research 2000; 6: 1796-1803) and lung cancer (Hofmann et al., J. Cancer Res. Clin. Oncology 2002; 128(10): 554-60).

XIAP is translated by a cap-independent mechanism of translation initiation that is mediated by a unique internal ribosome entry site (IRES) sequence element located in its 5' untranslated region. This allows XIAP mRNA to be actively translated during conditions of cellular stress when the majority of cellular protein synthesis is inhibited. Translational upregulation of XIAP in response to stress increases resistance to radiation induced cell death (Holcik et al., Oncogene 2000; 19: 4174-4177).

XIAP inhibition has been investigated in vitro via several techniques including RNA silencing, gene knockout, peptidic ligand mimetics and small molecule antagonists, and has been shown to promote apoptosis as a monotherapy and to sensitise many tumour types to chemotherapy, including bladder (Kunze et al., 2008; 28(4B): 2259-63). XIAP knockout mice are born at the expected Mendelian frequency, with no obvious physical or histological defects, and normal life spans (Harlin et al., Mol. Cell Biol. 2001; 21(10): 3604-

3608). This indicates that lacking XIAP activity is not toxic in normal tissues and suggests a therapeutic window over tumour cells. It was noted that the cIAP1 and cIAP2 levels are upregulated in the XIAP knockout mouse and may protect from pathology via a compensatory mechanism, suggesting pan-inhibition may be required for functional knockout. Similarly, cIAP1 and cIAP2 knockout mice are also asympotomatic (Conze et al., Mol. Biol. Cell 2005; 25(8): 3348-56). While lack of any one of the IAPs produced no overt phenotype in mice, deletion of cIAP1 with cIAP2 or XIAP resulted in mid embryonic lethality (Moulin, EMBO J., 2012).

Endogenous IAP antagonists such as SMAC have been used to validate members of this family as targets for therapeutic agents. SMAC peptides chemosensitise tumour cells, and in combination with platins and Tumour Necrosis Factor α-related apoptosis inducing ligand (TRAIL) in xenografts, results in tumour growth delay (Fulda et al., Nat. Med. 2002; 808-815; Yang et al., Cancer Res. 2003; 63: 831-837). A natural product, embellin, was identified as binding at the surface groove of the BIR3 domain of XIAP with similar affinity to the natural SMAC peptide. Embellin induces apoptosis in cell lines in vitro and results in tumour growth delay in xenografts (Nikolovska-Coleska et al., J. Med. Chem. 2004; 47(10): 2430-2440; Chitra et al., Chemotherapy 1994; 40: 109-113).

XIAP antisense oligonucleotides have been developed as therapeutic agents for solid tumour and haematological malignancies. In vitro these antisense oligonucleotides have been shown to knockdown protein expression levels by ~70%, induce apoptosis and sensitise cells to chemotherapy and delay tumour growth in vivo. One of these agents, AEG351156, has been studied in clinical trials (Hu et al., Clin. Cancer Res. 2003; 9: 2826-2836; Cummings et al., Br. J. Cancer 2005; 92: 532-538). Small molecule antagonists of XIAP developed include peptidomimetics as well as synthetic agents. The peptidomimetics target the BIR3 domain, mimicking SMAC disruption of caspase-9 binding to XIAP, have shown induction of apoptosis in a variety of tumour cell lines as a single agent, as well as chemosensitisers and are being further investigated clinically (Oost et al., J. Med. Chem. 2004; 47: 4417-4426; Sun et al., Bioorg. Med. Chem. Lett. 2005; 15: 793-797).

Synthetic small molecule antagonists of BIR3 and BIR2 domains also demonstrate anti-tumour activity in several different models, including induction of apoptosis by annexin-V staining and IC50s of <10 µM against over one-third of the NCI60 cell line panel. XIAP antagonists also induced dose-dependent cell death of primary-cultured leukaemia cells in 5 out of 5 chronic lymphocytic leukaemia cell lines and 4 out of 5 acute myeloid leukaemia cell lines (Schimmer et al., Cancer Cell 2004; 5: 25-35; Berezovskaya et al., Cancer Res. 2005; 65(6): 2378-86).

High levels of XIAP protein in tumour cell lines were inversely correlated with sensitivity to some anti-cancer drugs, particularly cytarabine and other nucleosides (Tamm et al., Clin. Cancer Research 2000; 6: 1796-1803). XIAP inhibition potentiates TRAIL-induced antitumor activity in two preclinical models of pancreatic cancer in vivo (Vogler 2008). Gene expression and transfection studies suggest that the increased expression of apoptosis suppressor XIAP plays an important role in anoikis resistance and in the survival of circulating human prostate carcinoma cells, thereby promoting metastasis. Small molecule antagonists were found to be anti-metastatic in these models (Berezovskaya et al., Cancer Res. 2005; 65(6): 2378-86).

XIAP has also been found to be involved in other pathways associated with cancer and other diseases and these may also benefit from XIAP targeted agents. The E3 ligase activity of the RING finger domain of XIAP is able to bind both to TAB1 and to an upstream BMP receptor (type 1), suggesting that XIAP may signal in a TGF-β-mediated pathway (Yamaguchi et al., EMBO 1999; 179-187). Focal adhesion kinase (FAK) overexpression has been shown to result in upregulated XIAP expression (Sonoda et al., J. Biol. Chem. 2000; 275: 16309-16315). E3 ligases are attractive therapeutic targets and molecules which target this activity in other proteins such as MDM2 are being developed (Vassilev et al., Science 2004; 303: 844-848). Direct or indirect inhibition of the XIAP ligase activity may also be useful in the treatment of cancer and other diseases. Dysregulated apoptotic signalling, which would result from inhibition of IAP function in controlling programmed cell death, has also been implicated in many diseases, including disorders associated with cell accumulation (e.g. cancer, autoimmunity, inflammation and restenosis) or disorders where excessive apoptosis results in cell loss (e.g. stroke, heart failure, neurodegeneration such as Alzheimer's disease, Parkinson's disease, Huntington's disease, amyotrophic lateral sclerosis, AIDS, ischaemia (stroke, myocardial infarction) and osteoporosis).

XIAP is an important apoptotic regulator in experimental autoimmune encephalomyelitis and a potential pharmacological target for treating autoimmune diseases such as multiple sclerosis (MS) (Moore et al., 2004; 203(1): 79-93). Antisense-mediated knockdown of XIAP reverses paralysis in an animal model of MS suggesting that treatments targeting XIAP, and perhaps other IAPs, may have utility in the treatment of MS (Hebb et al., Curr. Drug Disc. Tech. 2008; 5(1): 75-7).

cIAP1, cIAP-2, XIAP and survivin are overexpressed in malignant pleural mesothelioma and are responsible for a large degree of the resistance of cultured mesothelioma cells to cisplatin. Levels of circulating TNF-α are significantly higher in mesothelioma patients prior to surgical tumor debulking compared with those after surgery. TNF-α increases mRNA and protein levels of IAP-1, IAP-2 and XIAP (Gordon et al., 2007). NF-Kb upregulation plays an important survival role in mesotheliomas in response to the inflammatory effects of exposure to asbestos fibres (Sartore-Bianchi et al., 2007). IAP antagonists have the potential to reverse the pro-survival effect of TNF-α.

The ability of cell lines to upregulate TNF-alpha expression sufficiently to act in an autocrine fashion and kill the cells, once cIAP1 & 2 are depleted, is believed to be important for IAP activity (Nature Reviews Cancer (2010), 10(8), 561-74, Gryd-Hansen, M). In vivo, however, certain tumour types are surrounded by a pro-inflammatory cytokine network and hence the tumour cells which, on depletion of cIAP1/2 are switched towards cell killing by apoptosis, may be triggered to apoptose by TNF-alpha (or other Death Receptor cytokine agonists) already being produced by surrounding cells in the tumour microenvironment, such as tumour-associated macrophages, or indeed by the tumour cells themselves. Certain tumour types such as breast, ovarian and melanoma display this "inflammatory phenotype" which could potentially be targeted by IAP antagonists.

cIAP1 and cIAP2

Cellular IAP (cIAP) 1 and 2 are closely related members of the IAP family with three BIR domains, a RING domain and a caspase-recruitment (CARD) domain. A functional nuclear export signal exists within the CARD domain of cIAP1 which appears to be important for cell differentiation (Plenchette et al., Blood 2004; 104: 2035-2043). The presence of this CARD domain is unique to cIAP1 and cIAP2 within the IAP family of proteins. These two genes reside in tandem on chromosome 11 q22 and given their high degree of similarity are thought to have arisen via gene duplication.

cIAP1, like XIAP and survivin, is widely expressed in tumour cell lines, and has been found to be expressed at high levels in colorectal cancers in particular, as well as lung, ovarian, renal, CNS and breast cancers (Tamm et al., Clin. Cancer Res. 2000; 6: 1796-1803). cIAP2 expression is generally more restricted and is thought to be regulated though constitutive ubiquitination and degradation by cIAP1 (Conze et al., Mol. Biol. Cell 2005; 25(8): 3348-56; Mahoney et al., PNAS 2008; 105: 11778-11783). Immunohistochemistry and western blot analysis identified cIAP1 and cIAP2 as potential oncogenes as both are overexpressed in multiple lung cancers with or without higher copy numbers (Dia et al., Human Mol. Genetics 2003; 12(7): 791-801). cIAP1 expression level preferentially seems to play an important role in low-stage adenocarcinoma (Hofmann et al., J. Cancer Res. Clin. Oncology 2002; 128(10): 554-60).

Increased levels of cIAP1 and cIAP2 and reduced levels of endogenous inhibitors are associated with chemoresistance as has been seen for XIAP. cIAP overexpression has been found to correlate in vitro to resistance to DNA alkylating agents such as carboplatin, cisplatin and topoisomerase inhibitor VP-16 (Tamm et al., Clin. Cancer Res. 2000; 6: 1796-1803). Levels of cIAP1 and survivin were found to be high in thyroid cancer cells after cisplatin and doxorubicin treatment. Cells resistant to chemotherapy such as taxol showed reduced expression of SMAC and released minimal amounts of this protein from the mitochondria. Down-regulation of cIAP1 and survivin has been found to increase the cytotoxicity of cisplatin and doxorubicin, whereas overexpression of SMAC improved the efficacy of taxol. However, silencing of cIAP1 and survivin by RNA interference restored sensitivity to doxorubicin and cisplatin (Tirrò et al.; Cancer Res. 2006; 66(8): 4263-72).

SMAC mimetics such as LBW242 were originally thought to primarily target XIAP. However studies have shown that cIAP1 was targeted for degradation by autoubiquitination in cells (Yang et al., J. Biol. Chem. 2004; 279(17): 16963-16970) and may have contributed to the apoptotic effects that resulted. SiRNA of cIAP1 and Tumour Necrosis Factor (TNF)-alpha induction (or stimulation) were found to combine synergistically and render cell lines more sensitive (Gaither et al. Cancer Res. 2007; 67 (24): 11493-11498).

cIAP1 and cIAP2 have been demonstrated to be critical regulators of the NFκB signalling pathway which is involved in a diverse range of biological processes, particularly in innate and adaptive immunity as well as in proliferation and survival. NFκB pathway deregulation is associated with inflammation and cancers including hepatitis and ulcerative colitis, gastritis, hepatocellular carcinoma colorectal cancer and gastric cancers, as well as angiogenesis and metastasis (Shen et al., Apoptosis 2009; 14: 348-363).

On ligand binding, the TNF Receptor (TNFR) recruits TNFR-associated Death Domain (TRADD) and receptor-interacting protein (RIP)$_1$. TRAF2 and cIAP1/cIAP2 are then recruited to form a large membrane complex. RIP1 is ubiquitinated and these polyubiquitin chains serve as a docking site for downstream kinases, resulting in NFκB pathway signalling effects (Ea et al., Mol. Cell 2006; 22: 245-257; Wu et al., Nat. Cell Biol. 2006; 8: 398-406). The extended roles are complex and yet to be fully defined but cIAP1 and cIAP2 are identified as key components of TNF-alpha mediated NFκB signalling regulation as well as constitutive (ligand-independent/classical) NFκB signalling (Varfolomeev et al., Cell 2007; 131(4): 669-81). cIAP1 and cIAP2 have been shown to bind TRAF2, an adapter protein that functions in both the classical and alternative NFκB pathways as well as MAPK pathway signalling pathway (Rothe et al., Cell 2005; 83: 1243-1252). cIAP1 and cIAP2 directly target RIP1 for ubiquitination in vitro (Betrand et al., Mol. Cell 2008; 30: 689-700).

TNF-alpha regulates many cellular functions, including apoptosis, inflammation, immune response, and cell growth and differentiation (Trace et al., Annu. Rev. Med. 1994; 45: 491-503) and therapeutic IAP antagonists may be of benefit in conditions where these functions are affected.

Production of TNF-alpha is seen in many malignant tumours, and is one of the key drivers of cancer-related inflammation that drives tumour development and/or progression. cIAPs protect cancer cells from the lethal effects of TNF-alpha.

NAIP

NAIP was the first IAP to be discovered (Roy et al., Cell 1995; 80: 167-178). NAIP is unique among the IAPs in that it possesses a nucleotide-binding and oligomerisation domain, as well as leucine rich repeats which are similar to those contained in proteins normally involved in innate immunity. There are indications that NAIP may also be over expressed in some cancers including breast and oesophageal cancer (Nemoto et al., Exp. Mol. Pathol. 2004; 76(3): 253-9) as well as MS (Choi et al., J. Korean Med. 2007; 22 Suppl: S17-23; Hebb et al., Mult. Sclerosis 2008; 14(5): 577-94).

ML-IAP

Melanoma inhibitor of apoptosis protein (ML-IAP) contains a single BIR and RING finger motif. ML-IAP is a powerful inhibitor of apoptosis induced by death receptors and chemotherapeutic agents, probably functioning as a direct inhibitor of downstream effector caspases (Vucic et al., Curr. Biol. 2000; 10(21): 1359-66). ML-IAP is also known as Baculoviral IAP repeat-containing protein 7 (BIRC7), Kidney inhibitor of apoptosis protein (KIAP), RING finger protein 50 (RNF50) and Livin. The BIR domain of ML-IAP possesses an evolutionarily conserved fold that is necessary for anti-apoptotic activity. It has been found that the majority of melanoma cell lines express high levels of ML-IAP in contrast to primary melanocytes, which expressed undetectable levels. These melanoma cells were significantly more resistant to drug-induced apoptosis. Elevated expression of ML-IAP renders melanoma cells resistant to apoptotic stimuli and thereby potentially contributes to the pathogenesis of this malignancy.

ILP-2

ILP-2, also known as BIRC8, has a single BIR domain and a RING domain. ILP-2 is expressed only in testis in normal cells, and binds to caspase 9 (Richter et al, Mol. Cell. Biol. 2001; 21: 4292-301).

Survivin

Survivin, also known as BIRC5, inhibits both caspase 3 and caspase 7, but its primary function is mitotic progression regulation, rather than the regulation of apoptosis. Survivin promotes formation of microtubules in the mitotic spindle, counteracting apoptosis during cell cycle. Apoptosis inhibition by survivin is predictive of poor outcome in colorectal cancer (Kawasaki et al., Cancer Res. 1998; 58(22): 5071-5074) and stage III gastric cancer (Song et al., Japanese J. Clin. Oncol. 2009; 39(5): 290-296).

BRUCE

BRUCE (BIR repeat-containing ubiquitin-conjugating enzyme) is a peripheral membrane protein in the trans-Golgi network with a single BIR domain, most similar to that of survivin. BRUCE is inhibited via three mechanisms: (i) SMAC binding, (ii) HtrA2 protease and (iii) caspase-medi-

SUMMARY OF THE INVENTION

The present invention provides compounds according to formula (I). The present invention provides compounds which are useful in therapy, in particular in the treatment of cancer. The compounds of formula (I) may be antagonists of the IAP family of proteins (IAP), and especially XIAP, and/or cIAP (such as cIAP1 and/or cIAP2) and may be useful in the treatment of IAP-mediated conditions.

Accordingly, in first aspect of the invention, there is provided a compound of formula (I):

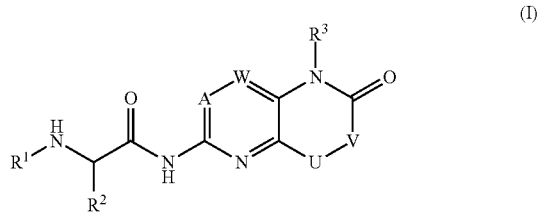

(I)

or tautomeric or stereochemically isomeric forms, N-oxides, pharmaceutically acceptable salts or the solvates thereof; wherein
A is selected from CH or N;
W is selected from $CR^6$ or N;
U is absent or is selected from $CH_2$, NH, S or O;
V is selected from $CR^4R^{4'}$ and $NR^5$ wherein when U is NH, S or O, V must be $CR^4R^{4'}$;
$R^1$ is selected from hydrogen, $C_{1-6}$ alkyl, $C_{2-6}$ alkenyl, $C_{2-6}$ alkynyl, —$(CH_2)_s$—$C_{3-8}$ cycloalkyl and —$(CH_2)_s$—$C_{3-8}$ cycloalkenyl, wherein said $C_{1-6}$ alkyl, $C_{2-6}$ alkenyl, $C_{2-6}$ alkynyl, $C_{3-8}$ cycloalkyl and $C_{3-8}$ cycloalkenyl may be optionally substituted by one or more $R^a$ groups;
$R^a$ is selected from halogen, —OH and $C_{1-6}$alkoxy;
$R^2$ is selected from hydrogen, $C_{1-4}$ alkyl, halo$C_{1-4}$ alkyl, $C_{2-4}$ alkenyl and —$(CH_2)_s$—$C_{3-8}$ cycloalkyl;
$R^3$ is selected from hydrogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —$(CH_2)_s$CN, —$S(O)_q$—$R^x$, —$C(=O)R^x$, —$C(=S)R^x$, —$C(=N)R^x$, —$(CR^xR^y)_s$—$C(=O)OR^z$, —$(CR^xR^y)_s$—$C(=O)NR^xR^y$, —$(CR^xR^y)_s$—$C(=S)NR^z$, —$(CR^xR^y)_s$—$C(=N)NR^z$, and —$(CH_2)_s$—$SO_2NR^xR^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups;
$R^4$ and $R^{4'}$ are independently selected from hydrogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —$(CR^xR^y)_s$—O—$R^z$, —O—$(CR^xR^y)_n$—$OR^z$, —$(CH_2)_s$—CN, —$S(O)_q$—$R^x$, —$C(=O)R^x$, —$C(=S)R^x$, —$C(=N)R^x$, —$(CR^xR^y)_s$—$C(=O)OR^z$, —$(CR^xR^y)_s$—O—$C(=O)$—$R^z$, —$(CR^xR^y)_s$—$C(=O)NR^xR^y$, —$(CH_2)_s$—$NR^xC(=O)R^y$, —$(CH_2)_s$—OC(=O)NR^xR^y$, —$(CH_2)_s$—$NR^xC(=O)OR^y$, —$(CH_2)_s$—$NR^xR^y$, —$NR^x$—$(CH_2)_s$—$R^z$, —$(CR^xR^y)_s$—$C(=S)NR^z$, —$(CR^xR^y)_s$—$C(=N)NR^z$, —$(CH_2)_s$—O—$C(=O)$—$C_{1-4}$alkyl-$NR^xR^y$, —$(CH_2)_s$—$NR^x$—$(CH_2)_n$—O—C(=O)—$R^z$, —$(CH_2)_s$$NR^x$—$(CH_2)_s$—$SO_2$—$R^y$, —$(CH_2)_s$—NH—$SO_2$—$NR^xR^y$ and —$(CH_2)_s$—$SO_2NR^xR^y$ groups, or $R^4$ and $R^{4'}$ together with the carbon atom to which they are attached, can join to form a 3-10 membered carbocyclyl or heterocyclyl group,
wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups;
$R^5$ is selected from hydrogen, $C_{1-8}$ alkyl, $C_{2-8}$ alkenyl, $C_{2-8}$ alkynyl, —Y—$C_{3-12}$-carbocyclyl, —Z-(3-12 membered heterocyclyl), —$(CH_2)_s$—CN, —$S(O)_q$—$R^x$, —$C(=O)R^x$, —$C(=S)R^x$, —$C(=N)R^x$, —$(CR^xR^y)_s$—$C(=O)OR^z$, —$(CR^xR^y)_s$—$C(=O)NR^xR^y$, —$(CR^xR^y)_s$—$C(=S)NR^z$, —$(CR^xR^y)_s$—$C(=N)NR^z$, and —$(CH_2)_s$—$SO_2NR^xR^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups;
$R^6$ is selected from hydrogen, halogen, $C_{1-4}$ alkyl, halo$C_{1-4}$ alkyl, halo$C_{1-4}$ alkoxy and $C_{1-4}$alkoxy;
$R^b$ is independently selected from halogen, $C_{1-8}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$—(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —$S(O)_q$—$R^x$, —$C(=O)R^x$, —$(CR^xR^y)_s$—$C(=O)OR^z$, —$(CR^xR^y)_s$—O—$C(=O)$—$R^z$, —$(CR^xR^y)_s$—$C(=O)NR^xR^y$, —$(CH_2)_s$—$NR^xC(=O)R^y$, —$(CH_2)_s$—OC(=O)NR^xR^y$, —$(CH_2)_s$—$NR^xC(=O)OR^y$, —$(CH_2)_s$—$NR^xR^y$, —$NR^x$—$(CH_2)_s$—$R^z$, —$(CH_2)_s$—O—$C(=O)$—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$, —$(CH_2)_s$—$SO_2NR^xR^y$ groups, wherein said $C_{1-6}$ alkyl, $C_{2-6}$ alkenyl, $C_{2-6}$ alkynyl, $C_{3-8}$ cycloalkyl, $C_{3-8}$ cycloalkenyl and heterocyclyl groups may be optionally substituted by one or more $R^x$ groups;
$R^c$ is independently selected from halogen, $C_{1-6}$ alkyl, $C_{2-6}$ alkenyl, $C_{2-6}$ alkynyl, —$(CH_2)$, —$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$alkoxy, $C_{1-6}$ alkanol, =O, =S, nitro, $Si(R^x)_4$, —$(CH_2)_s$—CN, —$S(O)_q$—$R^x$, —$C(=O)R^x$, —$(CR^xR^y)_s$—$C(=O)OR^z$, —$(CR^xR^y)$, —O—$C(=O)$—$R^z$, —$(CR^xR^y)_s$—$C(=O)NR^xR^y$, —$(CH_2)_s$—$NR^xC(=O)R^y$, —$(CH_2)_s$—OC(=O)NR^xR^y$, —$(CH_2)_s$—$NR^xC(=O)OR^y$, —$(CH_2)_s$—$NR^xR^y$, —$NR^x$—$(CH_2)_s$—$R^z$, —$(CH_2)_s$—O—$C(=O)$—$C_{1-4}$alkyl-$NR^xR^y$, —$(CH_2)_s$—$NR^x$—$(CH_2)_n$—O—C(=O)—$R^z$, —$(CH_2)_s$—$NR^x$—$(CH_2)$, —$SO_2$—$R^y$, —$(CH_2)_s$—NH—$SO_2$—$NR^xR^y$, —$(CH_2)_s$—$SO_2NR^xR^y$ and —$P(=O)(R^x)_2$ groups, wherein said $C_{1-6}$ alkyl, $C_{2-6}$ alkenyl, $C_{2-6}$ alkynyl, $C_{3-8}$ cycloalkyl, $C_{3-8}$ cycloalkenyl and heterocyclyl groups may be optionally substituted by one or more $R^x$ groups;
$R^x$, $R^y$ and $R^z$ independently represent hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-(4-7 membered saturated heterocyclyl), $C_{1-6}$ alkanol optionally substituted with one or more halo, —C(=O)OC_{1-6}$ alkyl, hydroxy, $C_{1-6}$ alkoxy, halo$C_{1-6}$ alkyl, —$(CH_2)_n$—O—$C_{1-6}$alkyl, —C(=O)—$(CH_2)_n$—$C_{1-6}$ alkoxy, —C(=O)—$C_{1-6}$alkyl, —$(CH_2)$, —CN, $C_{1-6}$ alkyl-$N(H)_{2-q}(C_{1-6}$alkyl)$_q$, —$N(H)_{2-q}(C_{1-6}$alkyl)$_q$, —C(=O)—$N(H)_{2-q}(C_{1-6}$alkyl)$_q$, —$(CH_2)_s$—NH—$SO_2$—$N(H)_{2-q}(C_{1-6}$alkyl)$_q$, —$(CH_2)_s$—$N(C_{1-4}$alkyl)-$SO_2$—$N(H)_{2-q}(C_{1-6}$alkyl)$_q$ and —$(CH_2)$, —O—C(=O)—$C_{1-4}$alkyl-$N(H)_{2-q}(C_{1-6}$alkyl)$_q$, and when attached to nitrogen or carbon or phosphorus or silicon atom $R^x$ and $R^y$ may join to form a 3-7 membered ring optionally containing one or two additional heteroatoms selected from O, N, S and oxidised forms of N or S;

Y and Z are independently selected from a bond, $-(CR^xR^y)_m-$, $-NR^x-$, $-C(=O)NR^x-$, $-NR^xC(=O)-$, $-(CR^xR^y)_q-O-$, $-O-(CR^xR^y)_q-$ and $-S(O)_q-$;

s independently represents an integer from 0-4;

n independently represents an integer from 1-4;

q represents an integer from 0-2;

m represents an integer from 1-2.

In a further aspect of the invention there is provided a compound of formula (I) for use in the prophylaxis or treatment of a disease or condition as described herein, pharmaceutical compositions comprising a compound of formula (I) and processes for the synthesis of compound of formula (I).

DEFINITIONS

Unless the context indicates otherwise, references to formula (I) in all sections of this document (including the uses, methods and other aspects of the invention) include references to all other sub-formula, sub-groups, preferences, embodiments and example as defined herein.

By "IAP" we mean any of the IAP family members XIAP, cIAP (cIAP1 and/or cIAP2), NAIP, ILP2, ML-IAP, survivin and/or BRUCE, in particular XIAP, cIAP1, cIAP2, ML-IAP, more particularly XIAP, cIAP1 and/or cIAP2, most particularly XIAP and/or cIAP1. In particular we mean the BIR domains of IAP, in particular the BIR domains of XIAP, cIAP1, or cIAP2.

By "one or more IAP family members" we mean any of the IAP family members in particular XIAP, cIAP1 and/or cIAP2, more particularly XIAP and/or cIAP1.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonist efficacy for their cognate receptors, and binding will disrupt the interaction and inhibit the function of any ligand (e.g. endogenous ligands or substrates, agonist or inverse agonist) at receptors. The antagonism may arise directly or indirectly, and may be mediated by any mechanism and at any physiological level. An example of indirect antagonism, would be the indirect antagonism of cIAP as a consequence of ubiquination of cIAP resulting in its degradation. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

As used herein, the term "mediated", as used e.g. in conjunction with IAP as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term 'optionally substituted' as used herein refers to a group which may be substituted or unsubstituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine.

The term 'nitro' as used herein refers to an $NO_2$ group.

The term '$C_{1-4}$alkyl', '$C_{1-6}$alky' or '$C_{1-8}$alkyl' as used herein as a group or part of a group refers to a linear or branched saturated hydrocarbon group containing from 1 to 4, 1 to 6 or 1 to 8 carbon atoms respectively. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{2-4}$alkenyl', '$C_{2-6}$alkenyl' or '$C_{2-8}$alkenyl' as used herein as a group or part of a group refers to a linear or branched hydrocarbon group containing from 2 to 4, 2 to 6 or 2 to 8 carbon atoms, respectively, and containing a carbon carbon double bond. Examples of such groups include $C_{3-4}$alkenyl or $C_{3-6}$alkenyl groups, such as ethenyl (vinyl), 1-propenyl, 2-propenyl (allyl), isopropenyl, butenyl, buta-1, 4-dienyl, pentenyl, and hexenyl.

The term '$C_{2-6}$alkynyl' or '$C_{2-8}$alkynyl' as used herein as a group or part of a group refers to a linear or branched hydrocarbon group having from 2 to 6 or 2 to 8 carbon atoms, respectively, and containing a carbon carbon triple bond. Examples of such groups include $C_{3-4}$alkynyl or $C_{3-6}$alkynyl groups such as ethynyl and 2 propynyl (propargyl) groups.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-6}$alkanol' as used herein as a group or part of a group refers to a $C_{1-6}$ alkyl group as defined herein wherein one or more than one hydrogen atom is replaced with a hydroxyl group.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$ alkyl' or 'hydroxy$C_{1-6}$ alkyl' therefore include monohydroxy$C_{1-4}$ alkyl, monohydroxy$C_{1-6}$ alkyl and also polyhydroxy$C_{1-4}$ alkyl and polyhydroxy$C_{1-6}$ alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The terms 'halo$C_{1-4}$ alkyl' or 'halo$C_{1-6}$alkyl' therefore include monohalo$C_{1-4}$ alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'halo$C_{1-4}$alkoxy' or 'halo$C_{1-6}$alkoxy' as used herein as a group or part of a group refers to a —O—$C_{1-4}$alkyl or —O—$C_{1-6}$alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy or trifluoromethoxy and the like.

The terms "heterocyclyl" and "carbocyclyl" as used herein shall, unless the context indicates otherwise, include both aromatic and non-aromatic ring systems. Thus, for example, the terms "heterocyclyl group" and "carbocyclyl group" include within their scope aromatic, non-aromatic, unsaturated, partially saturated and fully saturated carbocyclyl or heterocyclyl ring systems. In general, unless the context indicates otherwise, such groups may be monocyclic or bicyclic (including fused and bridged bicyclic groups) and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to heterocyclyl or carbocyclyl groups, the heterocyclyl or carbocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms typically selected from nitrogen, sulfur and oxygen. Typically the heterocyclyl ring will contain up to 4 heteroatoms, more typically up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;

c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms typically selected from nitrogen, sulfur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine. Partially saturated heterocyclyl groups include pyrazolines, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulfur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholine, piperidine (e.g. piperidin-1-yl, piperidin-2-yl, piperidin-3-yl and piperidin-4-yl), piperidinone, pyrrolidine (e.g. pyrrolidin-1-yl, pyrrolidin-2-yl and pyrrolidin-3-yl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. tetrahydropyran-4-yl), imidazoline, imidazolidinone, oxazoline, thiazoline, pyrazolin-2-yl, pyrazolidine, piperazinone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The nitrogen-containing heterocyclyl ring can be N-linked or C-linked. The heterocylic groups can contain, for example cyclic amine moieties (e.g. as in pyrrolidine), cyclic amides (such as a pyrrolidinone, piperidinone or caprolactam), cyclic sulfonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclyl groups include aziridine, morpholine, thiomorpholine, piperidine (e.g. piperidin-1-yl, piperidin-2-yl, piperidin-3-yl and piperidin-4-yl), pyrrolidine (e.g. pyrrolidin-1-yl, pyrrolidin-2-yl and pyrrolidin-3-yl), pyrrolidone, dihydrothiazole, imidazoline, imidazolidinone, oxazoline, thiazoline, 6H-1,2,5-thiadiazine, pyrazolin-2-yl, pyrazolin-3-yl, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

The carbocyclyl groups can be aryl groups having from 5 to 12 ring members, more usually from 5 to 10 ring members. The term 'aryl' as used herein refers to carbocyclyl aromatic groups including phenyl, naphthyl, indanyl, indenyl, and tetrahydronaphthyl groups. The term "aryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring. Examples of polycyclic (e.g. bicyclic) aryl groups containing an aromatic ring and a non-aromatic ring include indanyl groups. Non-aromatic carbocyclic groups include cycloalkyl and cycloalkenyl groups as defined herein.

The heterocyclyl or carbocyclyl groups can each be unsubstituted or substituted by one or more substituent groups. For example, heterocyclyl or carbocyclyl groups can be unsubstituted or substituted by 1, 2, 3 or 4 substituents. Where the heterocyclyl or carbocyclyl group is monocyclic or bicyclic, typically it is unsubstituted or has 1, 2 or 3 substituents as defined herein.

A combination of substituents is permissible only if such as combination results in a stable or chemically feasible compound (i.e. one that is not substantially altered when kept at 40° C. or less for at least a week).

The various functional groups and substituents making up the compounds of the invention are typically chosen such that the molecular weight of the compound of the invention does not exceed 1000. More usually, the molecular weight of the compound will be less than 750, for example less than 700, or less than 650, or less than 600, or less than 550. More preferably, the molecular weight is less than 525 and, for example, is 510, 500 or less.

DETAILED DESCRIPTION OF THE INVENTION

In one embodiment A is CH. In another embodiment A is N.

In one embodiment W is N. In another embodiment W is $CR^6$. In one embodiment W is CH.

In one embodiment A-W is CH—N. In another embodiment A-W is N—CH.

In a further embodiment A-W is $CR^6$—CH. In another embodiment A-W is CH—CH.

In one embodiment U is selected from $CH_2$, NH or O. In one embodiment U is absent. In another embodiment U is NH. In a further embodiment U is O. In a further embodiment U is $CH_2$.

In one embodiment V is $CR^4R^{4'}$. In another embodiment V is $NR^5$.

In one embodiment U is absent and V is $CR^4R^{4'}$. In another embodiment U is absent and V is $NR^5$.

In one embodiment U is $CH_2$ and V is $CR^4R^{4'}$. In another embodiment U is $CH_2$ and V is $NR^5$.

In a further embodiment U is NH and V is $CR^4R^{4'}$. In another embodiment U is O and V is $CR^4R^{4'}$.

In one embodiment when U is NH or O, then V is $CR^4R^{4'}$ and when U is absent or $CH_2$, then V is $NR^5$.

In one embodiment U is NH or O and V is $CR^4R^{4'}$, or U is $CH_2$ and V is $NR^5$. In another embodiment U is O and V is $CR^4R^{4'}$ or U is $CH_2$ and V is $NR^5$.

In one embodiment $R^1$ is selected from hydrogen, $C_{1-6}$ alkyl, $C_{3-6}$ alkenyl, $C_{3-6}$ alkynyl, —$(CH_2)_s$—$C_{3-8}$ cycloalkyl and —$(CH_2)_s$—$C_{3-8}$ cycloalkenyl, wherein said $C_{1-6}$ alkyl, $C_{2-6}$ alkenyl, $C_{2-6}$ alkynyl, $C_{3-8}$ cycloalkyl and $C_{3-8}$ cycloalkenyl may be optionally substituted by one or more $R^a$ groups.

In one embodiment $R^1$ is selected from $C_{1-6}$ alkyl, $C_{2-6}$ alkenyl, $C_{2-6}$ alkynyl, —$(CH_2)_s$—$C_{3-8}$ cycloalkyl and —$(CH_2)_s$—$C_{3-8}$ cycloalkenyl, wherein said $C_{1-6}$ alkyl, $C_{2-6}$ alkenyl, $C_{2-6}$ alkynyl, $C_{3-8}$ cycloalkyl and $C_{3-8}$ cycloalkenyl may be optionally substituted by one or more $R^a$ groups.

In another embodiment $R^1$ is hydrogen or $C_{1-6}$ alkyl, wherein said $C_{1-6}$ alkyl group may be optionally substituted by one or more $R^a$ groups. In another embodiment $R^1$ is hydrogen or methyl, wherein said methyl group may be optionally substituted by one or two $R^a$ groups, in particular halogen. In another embodiment $R^1$ is hydrogen or unsubstituted methyl (—$CH_3$ or —$CD_3$).

In another embodiment $R^1$ is $C_{1-6}$ alkyl, wherein said $C_{1-6}$ alkyl group may be optionally substituted by one or more $R^a$ groups.

In another embodiment $R^1$ is methyl optionally substituted with 1 or 2 $R^a$ substitutents.

In another embodiment $R^a$ is selected from halogen.

In one embodiment $R^1$ is unsubstituted methyl. In one embodiment $R^1$ is unsubstituted methyl (i.e. —$CH_3$ or —$CD_3$), in particular —$CH_3$.

In one embodiment $R^2$ is selected from $C_{1-4}$ alkyl and halo$C_{1-4}$ alkyl.

In one embodiment $R^2$ is $C_{1-4}$ alkyl.

In one embodiment $R^2$ is unsubstituted methyl. In one embodiment $R^1$ is unsubstituted methyl (i.e. —$CH_3$ or —$CD_3$), in particular —$CH_3$.

In one embodiment where $R^2$ is unsubstituted $C_{1-4}$ alkyl, unsubstituted $C_{2-4}$ alkenyl and unsubstituted —$(CH_2)_5C_{3-3}$ cycloalkyl, the centre to which the $R^2$ is attached has the (S) stereochemistry.

In one embodiment, the bond connecting $R^2$ to the adjacent carbon has the down orientation when the groups $R^1$—NH— and —C(=O) are orientated as in Formula (I) i.e. $R^1$—NH is to the left of said carbon and C(=O) is to the right of said carbon atom when the formula is a drawn in Formula (I).

In one embodiment, the hydrogen attached to the carbon adjacent to $R^2$ is $^1H$ or $^2H$ (i.e. deuterium, D). In one embodiment, the hydrogen attached to the carbon adjacent to $R^2$ is $^1H$. In one embodiment, the hydrogen attached to the carbon adjacent to $R^2$ is D ($^2H$).

In one embodiment $R^3$ is selected from $C_{1-3}$ alkyl, $C_{2-8}$ alkenyl, $C_{2-8}$ alkynyl, —Y—$C_{3-12}$ carbocyclyl, —Z-(3-12 membered heterocyclyl), —$(CH_2)_s$—CN, —$S(O)_q$—$R^x$, —C(=O)$R^x$, —C(=S)$R^x$, —C(=N)$R^x$, —$(CR^xR^y)_s$—C(=O)O$R^z$, —$(CR^xR^y)_s$—C(=O)N$R^xR^y$, —$(CR^xR^y)_s$—C(=S)N$R^z$, —$(CR^xR^y)_s$—C(=N)N$R^z$, and —$(CH_2)_s$—$SO_2NR^xR^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups;

In one embodiment $R^3$ is selected from hydrogen, $C_{1-8}$ alkyl, $C_{3-8}$ alkenyl, $C_{3-8}$ alkynyl, —Y—$C_{3-12}$ carbocyclyl, —Z-(3-12 membered heterocyclyl), —(CH$_2$)$_s$—CN, —S(O)$_q$—R$^x$, —C(=O)R$^x$, —C(=S)R$^x$, —C(=N)R$^x$, —(CR$^x$R$^y$)$_s$—C(=O)OR$^z$, —(CR$^x$R$^y$)$_s$—C(=O)NR$^x$R$^y$, —(CR$^x$R$^y$)$_s$—C(=S)NR$^z$, —(CR$^x$R$^y$)$_s$—C(=N)NR$^z$, and —(CH$_2$)$_s$—SO$_2$NR$^x$R$^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups.

In one embodiment $R^3$ is selected from hydrogen, $C_{1-8}$ alkyl, —Y—$C_{3-12}$ carbocyclyl, and —Z-(3-12 membered heterocyclyl) groups, wherein said $C_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups. In one embodiment $R^3$ is selected from hydrogen, $C_{1-8}$ alkyl, —Y—$C_{3-12}$ carbocyclyl, and —Z-(3-12 membered heterocyclyl) groups, wherein said $C_{1-8}$ alkyl groups may be optionally substituted by one or more $R^b$ groups, said carbocyclyl and heterocyclyl groups may be optionally substituted by one or more (e.g. 1, 2 or 3) $R^c$ groups, and Y and Z are independently selected from a bond and —(CR$^x$R$^y$)$_m$—.

In one embodiment $R^3$ is selected from $C_{1-8}$ alkyl, —Y—$C_{3-12}$ carbocyclyl, and —Z-(3-12 membered heterocyclyl) groups, wherein said $C_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups. In one embodiment $R^3$ is selected from hydrogen, $C_{1-8}$ alkyl, —Y—$C_{3-12}$ carbocyclyl, and —Z-(3-12 membered heterocyclyl) groups, wherein said $C_{1-8}$ alkyl groups may be optionally substituted by one or more $R^b$ groups, said carbocyclyl and heterocyclyl groups may be optionally substituted by one or more (e.g. 1, 2 or 3) $R^c$ groups, and Y and Z are independently selected from a bond and —(CR$^x$R$^y$)$_m$—.

In one embodiment $R^3$ is —Y—$C_{3-12}$ carbocyclyl, wherein said carbocyclyl group may be optionally substituted by one or more (e.g. 1, 2 or 3) $R^c$ groups and Y is selected from a bond and —(CR$^x$R$^y$)$_m$—. In one embodiment $R^3$ is —Y-phenyl wherein said phenyl group may be optionally substituted by one or more (e.g. 1, 2 or 3) $R^c$ groups and Y is selected from a bond and —(CR$^x$R$^y$)$_m$—. In one embodiment $R^3$ is selected from phenyl, chlorophenyl (e.g. 3-chloro-phenyl or 4-chloro-phenyl) and dichlorophenyl (e.g. 3,5 dichloro-phenyl). In one embodiment phenyl and chlorophenyl (e.g. 3-chloro-phenyl or 4-chloro-phenyl). In a further embodiment, $R^3$ is chlorophenyl (e.g. 4-chloro-phenyl).

In one embodiment $R^3$ is selected from hydrogen, $C_{1-8}$ alkyl, and —Y—$C_{3-12}$ carbocyclyl, wherein said $C_{1-8}$ alkyl groups may be optionally substituted by one or more (e.g. 1, 2 or 3) $R^b$ groups and said carbocyclyl groups may be optionally substituted by one or more (e.g. 1, 2 or 3) $R^c$ groups.

In one embodiment $R^3$ is selected from hydrogen, $C_{1-8}$ alkyl, and —Y—$C_{3-12}$ carbocyclyl, wherein said carbocyclyl groups may be optionally substituted by one or more (e.g. 1, 2 or 3) $R^c$ groups.

In one embodiment $R^3$ is selected from $C_{1-8}$ alkyl, and —Y—$C_{3-12}$ carbocyclyl, wherein said carbocyclyl groups may be optionally substituted by one or more (e.g. 1, 2 or 3) $R^c$ groups.

In one embodiment $R^3$ is selected from hydrogen, $C_{1-4}$ alkyl, and —Y—$C_{3-12}$ carbocyclyl, wherein said $C_{1-4}$ alkyl groups may be optionally substituted by one or more $R^b$ groups, said carbocyclyl groups may be optionally substituted by one or more (e.g. 1, 2 or 3) $R^c$ groups and Y is selected from a bond and —(CR$^x$R$^y$)$_m$—.

In one embodiment $R^3$ is selected from $C_{1-4}$ alkyl, and —Y—$C_{3-12}$ carbocyclyl, wherein said $C_{1-4}$ alkyl groups may be optionally substituted by one or more $R^b$ groups, said carbocyclyl groups may be optionally substituted by one or more (e.g. 1, 2 or 3) $R^c$ groups and Y is selected from a bond and —(CR$^x$R$^y$)$_m$—.

In one embodiment $R^3$ is selected from hydrogen, $C_{1-4}$ alkyl, halo$C_{1-4}$alkyl, and —Y—$C_{3-12}$ carbocyclyl, wherein said carbocyclyl groups may be optionally substituted by one or more (e.g. 1, 2 or 3) $R^c$ groups.

In one embodiment $R^3$ is selected from hydrogen, methyl and phenyl, wherein said methyl groups may be optionally substituted by one or more $R^b$ groups and wherein said phenyl groups may be optionally substituted by one or more (e.g. 1, 2 or 3) $R^c$ groups.

In one embodiment $R^3$ is phenyl, wherein said carbocyclyl groups may be optionally substituted by one or more (e.g. 1, 2 or 3) $R^c$ groups.

In one embodiment $R^3$ is selected from hydrogen, unsubstituted methyl, unsubstituted phenyl, chloro-phenyl (e.g. 3-chloro-phenyl or 4-chloro-phenyl) and dichlorophenyl (e.g. 3,5-dichloro-phenyl).

In one embodiment $R^3$ is other than hydrogen.

In one embodiment $R^3$ is selected from unsubstituted methyl, unsubstituted phenyl, chloro-phenyl (e.g. 3-chloro-phenyl or 4-chloro-phenyl) and dichlorophenyl (e.g. 3,5-dichloro-phenyl).

In one embodiment $R^4$ and $R^{4'}$ are independently selected from hydrogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —(CR$^x$R$^y$)$_s$—O—R$^z$, —O—(CR$^x$R$^y$)$_n$—OR$^z$, —(CH$_2$)$_s$—CN, —S(O)$_q$—R$^x$, —C(=O)R$^x$, —C(=S)R$^x$, —C(=N)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NR$^x$C(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$, —NR$^x$—(CH$_2$)$_s$—R$^z$, —(CR$^x$R$^y$)$_s$—C(=S)NR$^z$, —(CR$^x$R$^y$)$_s$—C(=N)NR$^z$, —(CH$_2$)$_s$—O—C(=O)—$C_{1-4}$alkyl-NR$^x$R$^y$, —(CH$_2$)$_s$—NR$^x$—(CH$_2$)$_n$—O—C(=O)—R$^z$, —(CH$_2$)$_s$—NR$^x$—(CH$_2$)$_s$—SO$_2$—R$^y$, —(CH$_2$)$_s$—NH—SO$_2$—NR$^x$R$^y$ and —(CH$_2$), —SO$_2$NR$^x$R$^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups.

In one embodiment $R^4$ and $R^{4'}$ are independently selected from hydrogen, $C_{1-8}$ alkyl, —Y—$C_{3-12}$ carbocyclyl, and —Z-(3-12 membered heterocyclyl), wherein said $C_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups.

In one embodiment $R^4$ and $R^{4'}$ are independently selected from hydrogen, $C_{1-8}$ alkyl, and —Y—$C_{3-12}$ carbocyclyl, wherein said $C_{1-8}$ alkyl groups may be optionally substituted by one or more $R^b$ groups, said carbocyclyl groups may be optionally substituted by one or more (e.g. 1, 2 or 3) $R^c$ groups and Y is selected from a bond and —(CR$^x$R$^y$)$_m$—.

In one embodiment $R^4$ and $R^{4'}$ are independently selected from hydrogen, $C_{1-6}$ alkyl, and —Y—$C_{3-12}$ carbocyclyl, wherein said $C_{1-6}$ alkyl groups may be optionally substituted by one or more $R^b$ groups, said carbocyclyl groups may be optionally substituted by one or more (e.g. 1, 2 or 3) $R^c$ groups and Y is selected from a bond and —(CR$^x$R$^y$)$_m$—.

In one embodiment $R^4$ and $R^{4'}$ are independently selected from hydrogen, methyl, ethyl, butyl, pentyl, phenyl and —(CH$_2$)-phenyl, wherein said C$_{1-6}$ alkyl groups may be optionally substituted by one or more $R^b$ groups, said phenyl groups may be optionally substituted by one or more (e.g. 1, 2 or 3) $R^c$ groups and Y is selected from a bond and —(CR$^x$R$^y$)$_m$—.

In one embodiment $R^4$ and $R^{4'}$ are independently selected from hydrogen, unsubstituted methyl, unsubstituted ethyl, unsubstituted butyl, unsubstituted pentyl, unsubstituted phenyl and unsubstituted —(CH$_2$)-phenyl.

In one embodiment $R^4$ is hydrogen and $R^{4'}$ is selected from hydrogen, unsubstituted methyl, unsubstituted ethyl, unsubstituted butyl (e.g. isobutyl), unsubstituted pentyl (e.g. isopentyl), unsubstituted phenyl and unsubstituted —(CH$_2$)-phenyl.

In one embodiment $R^4$ and $R^{4'}$ are both C$_{1-6}$ alkyl (e.g. methyl, ethyl, butyl, or pentyl), wherein said C$_{1-6}$ alkyl groups may be optionally substituted by one or more $R^b$ groups. In one embodiment $R^4$ and $R^{4'}$ are both unsubstituted methyl or ethyl, in particular ethyl.

In one embodiment $R^4$ and $R^{4'}$ together with the carbon atom to which they are attached, join to form a 3-10 membered carbocyclyl group or heterocyclyl group, wherein said carbocyclyl and heterocyclyl groups may be optionally substituted by one or more (e.g. 1, 2 or 3) $R^c$ groups.

In one embodiment $R^4$ and $R^{4'}$ together with the carbon atom to which they are attached, join to form a 3-10 membered aromatic carbocyclyl group or heterocyclyl group containing one or two heteroatoms selected from N, O, S and oxidised forms of N or S (e.g. where a 3-7 membered partially or fully saturated carbocyclyl or heterocyclyl group is fused to a 5-6 membered aromatic carbocyclyl or heterocyclyl group); wherein said carbocyclyl and heterocyclyl groups may be optionally substituted by one or more (e.g. 1, 2 or 3) $R^c$ groups. As defined herein aromatic (heteroaryl and aryl) groups can contain an aromatic and a non-aromatic ring.

In one embodiment $R^4$ and $R^{4'}$ together with the carbon atom to which they are attached, join to form a 3-10 membered carbocyclyl group or heterocyclyl group containing one or two heteroatoms selected from N, O, S and oxidised forms of N or S, wherein said carbocyclyl and heterocyclyl groups may be optionally substituted by one or more (e.g. 1, 2 or 3) $R^c$ groups.

In one embodiment $R^4$ and $R^{4'}$ together with the carbon atom to which they are attached, join to form a 3-10 membered carbocyclyl group, wherein said carbocyclyl group may be optionally substituted by one or more (e.g. 1, 2 or 3) $R^c$ groups.

In one embodiment $R^4$ and $R^{4'}$ together with the carbon atom to which they are attached, join to form a 3-10 membered fully saturated carbocyclyl group or heterocyclyl group containing one or two heteroatoms selected from N, O, S and oxidised forms of N or S, wherein said carbocyclyl and heterocyclyl groups may be optionally substituted by one or more (e.g. 1, 2 or 3) $R^c$ groups.

In one embodiment $R^4$ and $R^{4'}$ together with the carbon atom to which they are attached, join to form a 3-6 membered non-aromatic (i.e. partially or fully saturated) carbocyclyl or join to form a 8-10 membered aromatic carbocyclyl group group, wherein said carbocyclyl group may be optionally substituted by one or more (e.g. 1, 2 or 3) $R^c$ groups.

In one embodiment $R^4$ and $R^{4'}$ together with the carbon atom to which they are attached, join to form a 3-10 membered non-aromatic carbocyclyl group, wherein said carbocyclyl group may be optionally substituted by one or more (e.g. 1, 2 or 3) $R^c$ groups. In one embodiment $R^4$ and $R^{4'}$ together with the carbon atom to which they are attached, join to form an unsubstituted 3-6 membered non-aromatic carbocyclyl group. In one embodiment $R^4$ and $R^{4'}$ together with the carbon atom to which they are attached, join to form a 5 or 6 membered non-aromatic (e.g. fully saturated) carbocyclyl group, substituted by one or two C$_{1-6}$ alkyl groups (e.g. methyl). In one embodiment $R^4$ and $R^{4'}$ together with the carbon atom to which they are attached, can join to form cyclopentyl or cyclohexyl.

In one embodiment $R^4$ and $R^{4'}$ together with the carbon atom to which they are attached, join to form a 8-10 membered aromatic carbocyclyl or heterocyclyl group, wherein said carbocyclyl and heterocyclyl groups may be optionally substituted by one or more (e.g. 1, 2 or 3) $R^c$ groups.

In one embodiment $R^4$ and $R^{4'}$ together with the carbon atom to which they are attached, join to form a 8-10 membered aromatic carbocyclyl group (e.g. where a 3-6 membered partially or fully saturated carbocyclyl group is fused to a 6 membered aromatic carbocyclyl group), wherein said carbocyclyl group may be optionally substituted by one or more (e.g. 1, 2 or 3) $R^c$ groups. In one embodiment $R^4$ and $R^{4'}$ together with the carbon atom to which they are attached, join to form an unsubstituted 8-10 membered aromatic carbocyclyl group. In one embodiment $R^4$ and $R^{4'}$ together with the carbon atom to which they are attached, join to form indanyl.

In one embodiment $R^4$ and $R^{4'}$ together with the carbon atom to which they are attached, can join to form cyclopentyl, cyclohexyl or indanyl.

In one embodiment $R^5$ is selected from hydrogen, C$_{1-8}$ alkyl, C$_{3-8}$ alkenyl, C$_{3-8}$ alkynyl, —Y—C$_{3-12}$carbocyclyl, —Z-(3-12 membered heterocyclyl), —(CH$_2$)$_s$—CN, —S(O)$_q$—R$^x$, —C(=O)R$^x$, —C(=S)R$^x$, —C(=N)R$^x$, —(CR$^x$R$^y$)$_s$—C(=O)OR$^z$, —(CR$^x$R$^y$)$_s$—C(=O)NR$^x$R$^y$, —(CR$^x$R$^y$)$_s$—C(=S)NR$^z$, —(CR$^x$R$^y$)$_s$—C(=N)NR$^z$, and —(CH$_2$)$_s$—SO$_2$NR$^x$R$^y$ groups, wherein said C$_{1-8}$ alkyl, C$_{2-8}$ alkenyl and C$_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups.

In one embodiment, $R^5$ is selected from hydrogen, C$_{1-8}$ alkyl, —Y—C$_{3-12}$carbocyclyl, —Z-(3-12 membered heterocyclyl), wherein said C$_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups.

In one embodiment, $R^5$ is selected from hydrogen, C$_{1-8}$ alkyl, —Y—C$_{3-6}$carbocyclyl, —Z-(3-6 membered heterocyclyl), wherein said C$_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups.

In one embodiment, $R^5$ is selected from hydrogen, C$_{1-8}$ alkyl, —C$_{3-6}$carbocyclyl, —(CR$^x$R$^y$)$_m$—C$_{3-6}$carbocyclyl, 3-6 membered heterocyclyl, —(CR$^x$R$^y$)$_m$-(3-6 membered heterocyclyl), wherein said C$_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups.

In one embodiment, $R^5$ is selected from hydrogen, C$_{1-8}$ alkyl, —C$_{3-6}$carbocyclyl, —CH$_2$—C$_{3-6}$carbocyclyl, —CH(CH$_3$)—C$_{3-6}$carbocyclyl, 3-6 membered heterocyclyl, —CH$_2$-(3-6 membered heterocyclyl), wherein said C$_{1-8}$ alkyl groups may be optionally substituted by one or more $R^b$ groups and wherein said carbocyclyl and heterocyclyl groups may be optionally substituted by one or more (e.g. 1, 2 or 3) $R^c$ groups.

In one embodiment, $R^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, —CH$_2$-cyclopentyl, cyclohexyl, phenyl, —CH$_2$-phenyl, —CH$_2$CH$_2$-phenyl, piperidine, and —CH$_2$-thiazole, wherein said C$_{1-8}$ alkyl groups may be optionally substituted by one or more R$^b$ groups and wherein said carbocyclyl and heterocyclyl groups may be optionally substituted by one or more (e.g. 1, 2 or 3) R$^c$ groups.

In one embodiment, $R^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, —CH$_2$-cyclopentyl, cyclohexyl, 4,4-dimethyl-cyclohexyl, phenyl, chlorophenyl, dichlorophenyl, chlorofluorophenyl, —CH$_2$-phenyl, —CH$_2$-chlorophenyl, —CH$_2$CH$_2$-phenyl, piperidine-C(=O)CH$_3$, and —CH$_2$-thiazole.

In one embodiment, $R^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, cyclohexyl, phenyl, chlorophenyl, dichlorophenyl, chlorofluorophenyl, —CH$_2$-phenyl, —CH$_2$-chlorophenyl, —CH$_2$CH$_2$-phenyl, piperidine-C(=O)CH$_3$, and —CH$_2$-thiazole.

In one embodiment $R^6$ is selected from hydrogen and halogen. In another embodiment $R^6$ is hydrogen.

In one embodiment Y and Z are independently selected from a bond, —(CR$^x$R$^y$)$_m$—, —NR$^x$, —O—, and —S(O)$_q$—.

In one embodiment Y and Z are independently selected from a bond and —(CR$^x$R$^y$)$_m$—. In one embodiment m is 1. In another embodiment Y and Z are independently selected from a bond, —CH(CH$_3$)—, —CH$_2$CH$_2$—, —CF$_2$— and —CH$_2$—.

In another embodiment Y and Z are independently selected from a bond, —CH(CH$_3$), —CH$_2$CH$_2$ and —CH$_2$—. In another embodiment Y and Z are independently selected from a bond and —CH$_2$—.

Substituents on $R^3$, $R^4$ and $R^5$

In one embodiment, $R^3$, $R^4$ or $R^5$ are optionally substituted by R$^b$ or R$^c$ which are independently selected from halogen, C$_{1-6}$ alkyl, —(CH$_2$)$_s$—C$_{3-8}$ cycloalkyl, —(CH$_2$)$_s$—C$_{3-8}$ cycloalkenyl, —(CH$_2$)$_s$-phenyl, —(CH$_2$)$_s$-(4-7 membered saturated heterocyclyl), —(CR$^x$R$^y$)$_s$—O—R$^z$, —O—(CR$^x$R$^y$)$_n$—OR$^z$, haloC$_{1-6}$ alkyl, haloC$_{1-6}$ alkoxy, C$_{1-6}$ alkanol, —(CH$_2$)$_s$—CN, —S(O)$_q$—R$^x$, —C(=O)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NR$^x$C(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$, —(CH$_2$)$_s$—NH—SO$_2$—NR$^x$R$^y$, —(CH$_2$)$_s$—SO$_2$NR$^x$R$^y$ groups, wherein said C$_{1-6}$ alkyl, C$_{3-8}$ cycloalkyl, C$_{3-8}$ cycloalkenyl and heterocyclyl groups may be optionally substituted by one or more R$^x$ groups.

In one embodiment, $R^3$, $R^4$ or $R^5$ are optionally substituted by R$^b$ or R$^c$ which are independently selected from halogen, C$_{1-6}$ alkyl, —(CR$^x$R$^y$)$_s$—O—R$^z$, —(CH$_2$)$_s$—CN, C$_{1-6}$ alkyl-N(H)$_{2-q}$(C$_{1-6}$alkyl)$_q$, —N(H)$_{2-q}$(C$_{1-6}$alkyl)$_q$, —(CH$_2$)$_s$—C$_{3-8}$ cycloalkyl, —(CH$_2$)$_s$—C$_{3-8}$ cycloalkenyl, —(CH$_2$)$_s$-phenyl, —(CH$_2$)$_s$-(4-7 membered saturated heterocyclyl), —S(O)$_q$—R$^x$, —C(=O)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NR$^x$C(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$; wherein said C$_{1-6}$ alkyl, C$_{3-8}$ cycloalkyl, C$_{3-8}$ cycloalkenyl, phenyl and heterocyclyl groups may be optionally substituted by one or more R$^x$ groups;

R$^x$, R$^y$ and R$^z$ independently represent hydrogen, C$_{1-6}$ alkyl, —(CH$_2$)$_s$—C$_{3-8}$ cycloalkyl, —(CH$_2$)$_s$—C$_{3-8}$ cycloalkenyl, —(CH$_2$)$_s$-(4-7 membered saturated heterocyclyl), C$_{1-6}$ alkanol, —C(=O)OC$_{1-6}$ alkyl, hydroxy, C$_{1-6}$ alkoxy, haloC$_{1-6}$ alkyl, —(CH$_2$)$_n$—O—C$_{1-6}$alkyl, —C(=O)—C$_{1-6}$alkyl, —(CH$_2$)$_s$—CN, C$_{1-6}$ alkyl-N(H)$_{2-q}$(C$_{1-6}$alkyl)$_q$, —N(H)$_{2-q}$(C$_{1-6}$alkyl)$_q$, —C(=O)—N(H)$_{2-q}$(C$_{1-6}$alkyl)$_q$, and when attached to nitrogen or carbon or atom R$^x$ and R$^y$ may join to form a 3-7 membered ring optionally containing a one or two additional heteroatoms selected from O, N, S and oxidised forms of N or S.

In one embodiment, $R^3$, $R^4$ or $R^5$ are optionally substituted by R$^b$ or R$^c$ which are independently selected from halogen, C$_{1-6}$ alkyl, —(CR$^x$R$^y$), —O—R$^x$, —(CH$_2$)$_s$—CN, C$_{1-6}$ alkyl-N(H)$_{2-q}$(C$_{1-6}$alkyl)$_q$, —N(H)$_{2-q}$(C$_{1-6}$alkyl)$_q$, —(CH$_2$)$_s$—C$_{3-8}$ cycloalkyl, —(CH$_2$)$_s$—C$_{3-8}$ cycloalkenyl, —(CH$_2$)$_s$-phenyl, —(CH$_2$)$_s$-(4-7 membered saturated heterocyclyl), —S(O)$_q$—R$^x$, —C(=O)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NR$^x$C(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$; wherein said C$_{1-6}$ alkyl, C$_{3-8}$ cycloalkyl, C$_{3-8}$ cycloalkenyl, phenyl and heterocyclyl groups may be optionally substituted by one or more R$^x$ groups;

R$^x$, R$^y$ and R$^z$ independently represent hydrogen, C$_{1-6}$ alkyl, C$_{1-6}$ alkanol, —C(=O)OC$_{1-6}$ alkyl, hydroxy, C$_{1-6}$ alkoxy, haloC$_{1-6}$ alkyl, —(CH$_2$)$_n$—O—C$_{1-6}$alkyl, —C(=O)—C$_{1-6}$alkyl, —(CH$_2$)$_s$—CN, C$_{1-6}$ alkyl-N(H)$_{2-q}$(C$_{1-6}$alkyl)$_q$, —N(H)$_{2-q}$(C$_{1-6}$alkyl)$_q$, —C(=O)—N(H)$_{2-q}$(C$_{1-6}$alkyl)$_q$, and when attached to nitrogen or carbon or atom R$^x$ and R$^y$ may join to form a 3-7 membered ring optionally containing a one or two additional heteroatoms selected from O, N, S and oxidised forms of N or S.

In one embodiment, $R^3$, $R^4$ or $R^5$ are optionally substituted by R$^b$ or R$^c$ which are independently selected from halogen, C$_{1-6}$ alkyl, —(CH$_2$)$_s$—C$_{3-8}$ cycloalkyl, —(CH$_2$), —C$_{3-8}$ cycloalkenyl, —(CH$_2$)$_s$-phenyl, —(CH$_2$)$_s$-(4-7 membered saturated heterocyclyl), —(CR$^x$R$^y$)$_s$—O—R$^z$, —O—(CR$^x$R$^y$)$_n$—OR$^z$, —(CH$_2$)$_s$—CN, C$_{1-6}$ alkyl-N(H)$_{2-q}$(R$^x$)$_q$, —N(H)$_{2-q}$(R$^x$)$_q$, —S(O)$_q$—R$^x$, —C(=O)R$^x$, and —(CH$_2$)$_s$—N(H)$_{2-q}$(R$^x$)$_q$, wherein said C$_{1-6}$ alkyl, C$_{3-8}$ cycloalkyl, C$_{3-8}$ cycloalkenyl, phenyl and heterocyclyl groups may be optionally substituted by one or more R$^x$ groups and wherein R$^x$ is independently selected from hydrogen, halogen, C$_{1-6}$ alkyl, C$_{1-6}$ alkanol, hydroxy, C$_{1-6}$ alkoxy, and haloC$_{1-6}$ alkyl.

In one embodiment, $R^3$, $R^4$ or $R^5$ are optionally substituted by R$^b$ or R$^c$ which are independently selected from halogen, C$_{1-6}$ alkyl, —(CH$_2$)$_s$—O—R$^z$, —(CH$_2$)$_s$—CN, C$_{1-6}$ alkyl-N(H)$_{2-q}$(R$^x$)$_q$, —N(H)$_{2-q}$(R$^x$)$_q$, —S(O)$_q$—R$^x$, —C(=O)R$^x$, —(CH$_2$)$_s$—N(H)$_{2-q}$(R$^x$)$_q$ where R$^x$ is independently selected from hydrogen, C$_{1-6}$ alkyl, C$_{1-6}$ alkanol, hydroxy, C$_{1-6}$ alkoxy, and haloC$_{1-6}$ alkyl.

In one embodiment, $R^3$, $R^4$ or $R^5$ are optionally substituted by R$^b$ or R$^c$ which are independently selected from halogen, C$_{1-6}$ alkyl, C$_{1-6}$alkoxy, —(CH$_2$)$_s$—CN, C$_{1-6}$ alkyl-N(H)$_{2-q}$(C$_{1-6}$alkyl)$_q$, —N(H)$_{2-q}$(C$_{1-6}$alkyl)$_q$, —S(O)$_q$—C$_{1-6}$alkyl, —C(=O)C$_{1-6}$alkyl, —(CH$_2$)$_s$—N(H)$_{2-q}$(C$_{1-6}$alkyl)$_q$.

In one embodiment, $R^3$, $R^4$ or $R^5$ are optionally substituted by R$^b$ or R$^c$ which are independently selected from halogen, C$_{1-6}$ alkyl, haloC$_{1-6}$ alkyl, haloC$_{1-6}$alkoxy, C$_{1-6}$ alkanol, —(CH$_2$)$_s$—O—C$_{1-6}$ alkyl, —C(=O)C$_{1-6}$alkyl, —(CH$_2$)$_s$—C$_{3-8}$ cycloalkyl, —(CH$_2$)$_s$—C$_{3-8}$ cycloalkenyl, and —(CH$_2$)$_s$-(4-7 membered saturated heterocyclyl).

In one embodiment, $R^3$, $R^4$ or $R^5$ are optionally substituted by R$^b$ or R$^c$ which are independently selected from fluorine, chlorine, methoxy, ethoxy, difluoromethoxy, methyl, ethyl, isopropyl, tert-butyl, trifluoromethyl, —C(=O)methyl, —N(H)$_{2-q}$(C$_{1-6}$alkyl)$_q$, morpholino, trifluoromethyl, N-methylpiperazinyl, piperazinyl, piperidinyl, pyrrolidinyl, pyrrolidinylmethyl, and morpholinomethyl.

In one embodiment, $R^3$, $R^4$ or $R^5$ are optionally substituted by $R^b$ or $R^c$ which are independently selected from fluorine, chlorine, and —C(=O)methyl.

The groups $R^3$, $R^4$ or $R^5$ may be optionally substituted by more than one substituent. Thus, for example, there may be 1 or 2 or 3 or 4 substituents, more typically 1, 2 or 3 substituents. In one embodiment, where $R^3$, $R^4$ or $R^5$ contains a six membered ring (such as a phenyl ring), there may be a single substituent which may be located at any one of the 2-, 3- and 4-positions on the ring. In another embodiment, there may be two or three substituents and these may be located at the 2-, 3-, 4- or 6-positions around the ring. By way of example, $R^3$, $R^4$ or $R^5$ phenyl ring may be 2,6-disubstituted, 2,3-disubstituted, 2,4-disubstituted 2,5-disubstituted, 2,3,6-trisubstituted or 2,4,6-trisubstituted.

In one embodiment, where $R^3$, $R^4$ or $R^5$ are a phenyl or benzyl group it may be mono substituted at the 2-, 3- or 4-position or disubstituted at positions 2- and 6- with substituents independently selected from fluorine and chlorine.

In one embodiment, $R^x$, $R^y$ and $R^z$ independently represent hydrogen or $C_{1-6}$ alkyl. In one embodiment, $R^x$, $R^y$ and $R^z$ independently represent hydrogen or methyl.

Sub-Formulae

In one embodiment, the compound of formula (I) is a compound of formula (Ia):

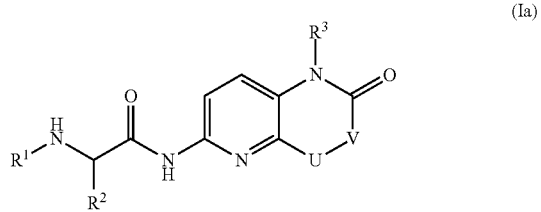

(Ia)

or tautomeric or stereochemically isomeric forms, N-oxides, pharmaceutically acceptable salts or the solvates thereof; wherein $R^1$, $R^2$, $R^3$, A, U, and V are as defined herein or in any of the embodiments.

In one embodiment, the compound of formula (I) is a compound of formula (Ia) wherein:
U is absent or is selected from $CH_2$, NH or O;
V is selected from $CR^4R^{4'}$ and $NR^5$ wherein when U is NH or O, V is $CR^4R^{4'}$ and when U is absent or $CH_2$, V is $NR^5$;
$R^1$ is $C_{1-6}$ alkyl, wherein said $C_{1-6}$ alkyl group may be optionally substituted by one or more $R^a$ groups;
$R^a$ is selected from halogen, —OH and —O—$C_{1-6}$alkyl;
$R^2$ is $C_{1-4}$ alkyl;
$R^3$ is selected from hydrogen, $C_{1-8}$ alkyl, and —Y—$C_{3-12}$ carbocyclyl, wherein said $C_{1-8}$ alkyl group may be optionally substituted by one or more $R^b$ groups and wherein said carbocyclyl groups may be optionally substituted by one or more (e.g. 1, 2 or 3) $R^c$ groups;
$R^4$ and $R^{4'}$ are independently selected from hydrogen, $C_{1-8}$ alkyl, and —Y—$C_{3-12}$ carbocyclyl, or $R^4$ and $R^{4'}$ together with the carbon atom to which they are attached, can join to form a 3-10 membered carbocyclyl group optionally containing one or two heteroatoms selected from N, O, S and oxidised forms of N or S,
wherein said $C_{1-6}$ alkyl group may be optionally substituted by one or more $R^b$ groups and wherein said carbocyclyl may be optionally substituted by one or more (e.g. 1, 2 or 3) $R^c$ groups;
$R^5$ is selected from hydrogen, $C_{1-8}$ alkyl, —Y—$C_{3-12}$carbocyclyl, —Z-(3-12 membered heterocyclyl), wherein said $C_{1-8}$ alkyl group may be optionally substituted by one or more $R^b$ groups and wherein said carbocyclyl and heterocyclyl groups may be optionally substituted by one or more (e.g. 1, 2 or 3) $R^c$ groups;
$R^b$ is independently selected from halogen, $C_{1-6}$ alkyl, —($CH_2$)$_s$—$C_{3-8}$ cycloalkyl, —($CH_2$)$_s$—$C_{3-8}$ cycloalkenyl, —($CH_2$)$_s$-phenyl, —($CH_2$)$_s$-(4-7 membered saturated heterocyclyl), —($CR^xR^y$)$_s$—O—$R^z$, —O—($CR^xR^y$)$_n$—$OR^z$, halo$C_{1-6}$ alkyl, halo$C_{1-6}$ alkoxy, $C_{1-6}$ alkanol;
$R^c$ is independently selected from halogen, $C_{1-6}$ alkyl, —($CH_2$)$_s$—$C_{3-8}$ cycloalkyl, —($CH_2$)$_s$—$C_{3-8}$ cycloalkenyl, —($CH_2$)$_s$-phenyl, —($CH_2$)$_s$-(4-7 membered saturated heterocyclyl), —($CR^xR^y$)$_s$—O—$R^z$, —O—($CR^xR^y$)$_n$—$OR^z$, halo$C_{1-6}$ alkyl, halo$C_{1-6}$ alkoxy, $C_{1-6}$ alkanol and —C(=O)$R^x$;
Y and Z are independently selected from a bond and —($CR^xR^y$)$_m$—;
$R^x$, $R^y$ and $R^z$ independently represent hydrogen, $C_{1-6}$ alkyl, —($CH_2$)$_s$$C_{3-8}$ cycloalkyl, —($CH_2$)$_s$—$C_{3-8}$ cycloalkenyl, —($CH_2$)$_s$-(4-7 membered saturated heterocyclyl), $C_{1-6}$ alkanol optionally substituted with one or more halo, —C(=O)O$C_{1-6}$ alkyl, hydroxy, $C_{1-6}$ alkoxy, halo$C_{1-6}$ alkyl, —($CH_2$)$_n$—O—$C_{1-6}$alkyl, —C(=O)—$C_{1-6}$alkyl, —($CH_2$)$_s$—CN, $C_{1-6}$ alkyl-N(H)$_{2-q}$($C_{1-6}$alkyl)$_q$, —N(H)$_{2-q}$($C_{1-6}$alkyl)$_q$, —C(=O)—N(H)$_{2-q}$($C_{1-6}$alkyl)$_q$, —($CH_2$), —NH—SO$_2$—N(H)$_{2-q}$ ($C_{1-6}$alkyl)$_q$, —($CH_2$)$_s$—N($C_{1-4}$ alkyl)-SO$_2$—N(H)$_{2-q}$($C_{1-6}$alkyl)$_c$, and —($CH_2$)$_s$—O—C(=O)—$C_{1-4}$alkyl-N(H)$_{2-q}$($C_{1-6}$alkyl)$_q$, and when attached to nitrogen or carbon atom $R^x$ and $R^y$ may join to form a 3-7 membered ring optionally containing a one or two additional heteroatoms selected from O, N, S and oxidised forms of N or S;
s independently represents an integer from 0-4;
n independently represents an integer from 1-4;
q represents an integer from 0-2;
m represents an integer from 1-2;

In one embodiment, the compound of formula (I) is a compound of formula (Ia) or tautomeric or stereochemically isomeric forms, N-oxides, pharmaceutically acceptable salts or the solvates thereof; wherein
U is absent or is selected from $CH_2$, NH or O;
V is selected from $CR^4R^{4'}$ and $NR^5$ wherein when U is NH or O, V is $CR^4R^{4'}$ and when U is absent or $CH_2$, V is $NR^5$;
$R^1$ is $C_{1-6}$ alkyl, wherein said $C_{1-6}$ alkyl group may be optionally substituted by one or more $R^a$ groups;
$R^a$ is selected from halogen, —OH and —O—$C_{1-8}$alkyl;
$R^2$ is $C_{1-4}$ alkyl;
$R^3$ is selected from hydrogen, $C_{1-8}$ alkyl, and —Y—$C_{3-12}$ carbocyclyl, wherein said carbocyclyl groups may be optionally substituted by one or more (e.g. 1, 2 or 3) $R^c$ groups;
$R^4$ and $R^{4'}$ are independently selected from hydrogen, $C_{1-8}$ alkyl, and —Y—$C_{3-12}$ carbocyclyl, or $R^4$ and $R^{4'}$ together with the carbon atom to which they are attached, can join to form a 3-10 membered carbocyclyl group optionally containing one or two heteroatoms selected from N, O, S and oxidised forms of N or S,
wherein said carbocyclyl may be optionally substituted by one or more (e.g. 1, 2 or 3) $R^c$ groups;
$R^5$ is selected from hydrogen, $C_{1-8}$ alkyl, —Y—$C_{3-12}$carbocyclyl, —Z-(3-12 membered heterocyclyl), wherein said $C_{1-8}$ alkyl group may be optionally substituted by one or more $R^b$ groups and wherein said carbocyclyl and heterocyclyl groups may be optionally substituted by one or more (e.g. 1, 2 or 3) $R^c$ groups;
$R^b$ is independently selected from halogen, $C_{1-8}$ alkyl, —($CH_2$), —$C_{3-8}$ cycloalkyl, —($CH_2$)$_s$—$C_{3-8}$ cycloalkenyl, —($CH_2$)$_s$-phenyl, —($CH_2$)$_s$-(4-7 membered saturated heterocyclyl), —(CR$^x$R$^y$)$_s$—O—R$^z$, —O—(CR$^x$R$^y$)$_n$—OR$^z$, haloC$_{1-6}$ alkyl, haloC$_{1-6}$ alkoxy, C$_{1-6}$ alkanol;

R$^c$ is independently selected from halogen, C$_{1-6}$ alkyl, —(CH$_2$)$_s$—C$_{3-8}$ cycloalkyl, —(CH$_2$)$_s$—C$_{3-8}$ cycloalkenyl, —(CH$_2$)$_s$-phenyl, —(CH$_2$)$_s$-(4-7 membered saturated heterocyclyl), —(CH$_2$)$_s$—O—C$_{1-6}$alkyl, O—(CH$_2$)$_n$—O—C$_{1-6}$alkyl, haloC$_{1-6}$ alkyl, haloC$_{1-6}$ alkoxy, C$_{1-6}$ alkanol and —C(=O)—C$_{1-6}$alkyl;

Y and Z are independently selected from a bond, CH$_2$, CH$_2$CH$_2$ and —CH(CH$_3$)—;

s independently represents an integer from 0-4;

n independently represents an integer from 1-4;

q represents an integer from 0-2;

In one embodiment, the compound of formula (I) is a compound of formula (Ib)

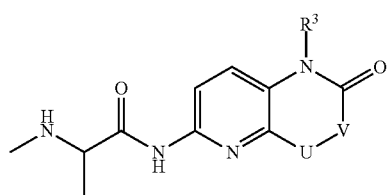

(Ib)

or tautomeric or stereochemically isomeric forms, N-oxides, pharmaceutically acceptable salts or the solvates thereof; wherein R$^3$, A, U, and V are as defined herein or in any of the embodiments.

In one embodiment, the compound of formula (I) is a compound of formula (Ib) wherein U is NH or O and V is CR$^4$R$^{4'}$, or U is absent or CH$_2$ and V is NR$^5$;

R$^3$ is selected from hydrogen, methyl, phenyl, chlorophenyl (e.g. 3-chloro-phenyl or 4-chloro-phenyl) and dichlorophenyl (e.g. 3,5-dichloro-phenyl);

R$^4$ and R$^{4'}$ are independently selected from hydrogen, methyl, ethyl, butyl, pentyl, cyclopentyl, phenyl, and benzyl;

or R$^4$ and R$^{4'}$ together with the carbon atom to which they are attached, can join to form cyclopenyl, cyclohexyl, or indanyl;

R$^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, —CH$_2$-cyclopentyl, cyclohexyl, dimethylcyclohexyl, phenyl, chlorophenyl, dichlorophenyl, chlorofluorophenyl, —CH$_2$-phenyl, —CH$_2$-chlorophenyl, —CH$_2$CH$_2$-phenyl, piperidine-C(=O)CH$_3$, and —CH$_2$-thiazole.

In one embodiment, the compound of formula (I) is a compound of formula (Ic)

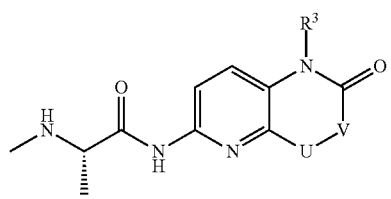

(Ic)

or tautomeric or stereochemically isomeric forms, N-oxides, pharmaceutically acceptable salts or the solvates thereof; wherein R$^3$, A, U, and V are as defined herein or in any of the embodiments.

In one embodiment, the compound of formula (I) is a compound of formula (Ic) wherein U is NH or O and V is CR$^4$R$^{4'}$, or U is absent or CH$_2$ and V is NR$^5$;

R$^3$ is selected from hydrogen, methyl, phenyl chloro-phenyl (e.g. 3-chloro-phenyl or 4-chloro-phenyl) and dichlorophenyl (e.g. 3,5 dichloro-phenyl);

R$^4$ and R$^{4'}$ are independently selected from hydrogen, methyl, ethyl, butyl, pentyl, cyclopentyl, phenyl, and benzyl;

or R$^4$ and R$^{4'}$ together with the carbon atom to which they are attached, can join to form cyclopenyl, cyclohexyl, or indanyl;

R$^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, —CH$_2$-cyclopentyl, cyclohexyl, dimethylcyclohexyl, phenyl, chlorophenyl, dichlorophenyl, chlorofluorophenyl, —CH$_2$-phenyl, —CH$_2$-chlorophenyl, —CH$_2$CH$_2$-phenyl, piperidine-C(=O)CH$_3$, and —CH$_2$-thiazole.

In one embodiment, the compound of formula (I) is a compound of formula (Ib) or (Ic) wherein:

U is NH or O and V is CR$^4$R$^{4'}$, or U is CH$_2$ and V is NR$^5$;

R$^3$ is selected from hydrogen, methyl, phenyl, chlorophenyl (e.g. 3-chloro-phenyl or 4-chloro-phenyl) and dichlorophenyl (e.g. 3,5 dichloro-phenyl);

R$^4$ and R$^{4'}$ are independently selected from hydrogen, methyl, ethyl, butyl, pentyl, cyclopentyl, phenyl, and benzyl;

or R$^4$ and R$^{4'}$ together with the carbon atom to which they are attached, can join to form cyclopenyl, cyclohexyl, or indanyl;

R$^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, —CH$_2$-cyclopentyl, cyclohexyl, dimethylcyclohexyl, phenyl, chlorophenyl, dichlorophenyl, chlorofluorophenyl, —CH$_2$-phenyl, —CH$_2$-chlorophenyl, —CH$_2$CH$_2$-phenyl, piperidine-C(=O)CH$_3$, and —CH$_2$-thiazole.

In one embodiment, the compound of formula (I) is a compound of formula (Ib) or (Ic) wherein:

U is O and V is CR$^4$R$^{4'}$ or U is CH$_2$ and V is NR$^5$;

R$^3$ is selected from phenyl and chlorophenyl (e.g. 3-chloro-phenyl or 4-chloro-phenyl);

R$^4$ and R$^{4'}$ are independently selected from hydrogen, methyl, ethyl, butyl, pentyl, cyclopentyl, phenyl, and benzyl;

or R$^4$ and R$^{4'}$ together with the carbon atom to which they are attached, can join to form cyclopenyl, cyclohexyl, or indanyl;

R$^5$ is selected from hydrogen, methyl, propyl (e.g. i-propyl or n-propyl), butyl (e.g. i-butyl), pentyl, hexyl, heptyl, —CH(CH$_3$)-cyclobutyl, cyclopentyl, cyclohexyl, dimethylcyclohexyl, phenyl, chlorophenyl, dichlorophenyl, chlorofluorophenyl, —CH$_2$-phenyl, —CH$_2$-chlorophenyl, —CH$_2$CH$_2$-phenyl, piperidine-C(=O)CH$_3$, and —CH$_2$-thiazole.

In one embodiment, the invention provides a compound of formula (I) which is selected from the following compounds or is one of the following compounds:

N-[3-(4-Chloro-benzyl)-2-oxo-2,3-dihydro-1H-imidazo[4,5-b]pyridin-5-yl]-2-methylamino-propionamide;

(S)—N-[1-(4-Chloro-phenyl)-2-oxo-2,3-dihydro-1H-pyrido[2,3-b][1,4]oxazin-6-yl]-2-methylamino-propionamide;

(S)—N—[(S)-1-(4-Chloro-phenyl)-3-methyl-2-oxo-3-phenyl-2,3-dihydro-1H-pyrido[2,3-b][1,4]oxazin-6-yl]-2-methylamino-propionamide;

(S)—N—((S)-3-Benzyl-2-oxo-2,3-dihydro-1H-pyrido[2,3-b][1,4]oxazin-6-yl)-2-methylamino-propionamide;

(S)—N-[1-(4-Chloro-phenyl)-3,3-diethyl-2-oxo-2,3-dihydro-1H-pyrido[2,3-b][1,4]oxazin-6-yl]-2-methylamino-propionamide;

(S)—N-[1-(4-Chloro-phenyl)-3,3-dimethyl-2-oxo-2,3-dihydro-1H-pyrido[2,3-b][1,4]oxazin-6-yl]-2-methylamino-propionamide;

(2S)—N-[4'-(4-Chlorophenyl)-3'-oxo-3',4'-dihydrospiro[cyclohexane-1,2'-pyrido[2,3-b][1,4]oxazine]-7'-yl]-2-(methylamino)propanamide;

(2S)—N-[4'-(4-Chlorophenyl)-3'-oxo-3',4'-dihydrospiro[cyclopentane-1,2'-pyrido[2,3-b][1,4]oxazine]-7'-yl]-2-(methylamino)propanamide;

(2S)—N-[4'-(4-Chlorophenyl)-3'-oxo-1,3,3',4'-tetrahydrospiro[indene-2,2'-pyrido[2,3-b][1,4]oxazine]-7'-yl]-2-(methylamino)propanamide;

(S)—N-[1-(3-Chloro-phenyl)-3,3-dimethyl-2-oxo-2,3-dihydro-1H-pyrido[2,3-b][1,4]oxazin-6-yl]-2-methylamino-propionamide;

(S)—N-[3-Benzyl-1-(3-chloro-phenyl)-3-methyl-2-oxo-2,3-dihydro-1H-pyrido[2,3-b][1,4]oxazin-6-yl]-2-methylamino-propionamide;

(S)—N-[1-(3-Chloro-phenyl)-3-isobutyl-3-methyl-2-oxo-2,3-dihydro-1H-pyrido[2,3-b][1,4]oxazin-6-yl]-2-methylamino-propionamide;

(S)—N-[1-(3-Chloro-phenyl)-3-cyclopentyl-3-methyl-2-oxo-2,3-dihydro-1H-pyrido[2,3-b][1,4]oxazin-6-yl]-2-methylamino-propionamide;

(S)-2-Methylamino-N-[3-methyl-3-(3-methyl-butyl)-2-oxo-1-phenyl-2,3-dihydro-1H-pyrido[2,3-b][1,4]oxazin-6-yl]-propionamide;

(S)-2-Methylamino-N—((S)-3-methyl-2-oxo-1,2,3,4-tetrahydro-pyrido[2,3-b]pyrazin-6-yl)-propionamide;

(S)-2-Methylamino-N-(2-oxo-1,2,3,4-tetrahydro-pyrido[2,3-b]pyrazin-6-yl)-propionamide;

(S)—N-(1,3-Dimethyl-2-oxo-2,3-dihydro-1H-imidazo[4,5-b]pyridin-5-yl)-2-methylamino-propionamide;

(S)—N-(3-Benzyl-2-oxo-1-phenyl-1,2,3,4-tetrahydro-pyrido[3,2-d]pyrimidin-6-yl)-2-methylamino-propionamide;

(S)-2-Methylamino-N-(2-oxo-1-phenyl-1,2,3,4-tetrahydro-pyrido[3,2-d]pyrimidin-6-yl)-propionamide;

(S)—N-(1,3-Dimethyl-2-oxo-1,2,3,4-tetrahydro-pyrido[3,2-d]pyrimidin-6-yl)-2-methylamino-propionamide;

(S)—N-[1,3-Bis-(4-chloro-phenyl)-2-oxo-1,2,3,4-tetrahydro-pyrido[3,2-d]pyrimidin-6-yl]-2-methylamino-propionamide;

(S)—N-[1-(4-Chloro-phenyl)-2-oxo-1,2,3,4-tetrahydro-pyrido[3,2-d]pyrimidin-6-yl]-2-methylamino-propionamide;

(S)-2-Methylamino-N-(2-oxo-1,3-diphenyl-1,2,3,4-tetrahydro-pyrido[3,2-d]pyrimidin-6-yl)-propionamide;

(S)—N-[1,3-Bis-(3-chloro-phenyl)-2-oxo-1,2,3,4-tetrahydro-pyrido[3,2-d]pyrimidin-6-yl]-2-methylamino-propionamide;

(S)—N-[1,3-Bis-(3,5-dichloro-phenyl)-2-oxo-1,2,3,4-tetrahydro-pyrido[3,2-d]pyrimidin-6-yl]-2-methylamino-propionamide;

(S)—N-[1-(4-Chloro-phenyl)-3-methyl-2-oxo-1,2,3,4-tetrahydro-pyrido[3,2-d]pyrimidin-6-yl]-2-methylamino-propionamide;

(S)—N-[3-(5-Chloro-2-fluoro-phenyl)-2-oxo-1-phenyl-1,2,3,4-tetrahydro-pyrido[3,2-d]pyrimidin-6-yl]-2-methylamino-propionamide;

(S)-2-Methylamino-N-(2-oxo-1-phenyl-3-propyl-1,2,3,4-tetrahydro-pyrido[3,2-d]pyrimidin-6-yl)-propionamide;

(S)—N-[1-(4-Chloro-phenyl)-3-cyclohexyl-2-oxo-1,2,3,4-tetrahydro-pyrido[3,2-d]pyrimidin-6-yl]-2-methylamino-propionamide;

(S)—N-[1-(4-Chloro-phenyl)-3-cyclopentyl-2-oxo-1,2,3,4-tetrahydro-pyrido[3,2-d]pyrimidin-6-yl]-2-methylamino-propionamide;

(S)—N-[1-(4-Chloro-phenyl)-3-isopropyl-2-oxo-1,2,3,4-tetrahydro-pyrido[3,2-d]pyrimidin-6-yl]-2-methylamino-propionamide;

(S)—N-[1-(3-Chloro-phenyl)-3-isopropyl-2-oxo-1,2,3,4-tetrahydro-pyrido[3,2-d]pyrimidin-6-yl]-2-methylamino-propionamide;

(S)—N-(3-isopropyl-2-oxo-1,2,3,4-tetrahydro-pyrido[3,2-d]pyrimidin-6-yl)-2-methylamino-propionamide;

(S)—N-[1-(4-Chloro-phenyl)-3-(1,3-dimethyl-butyl)-2-oxo-1,2,3,4-tetrahydro-pyrido[3,2-d]pyrimidin-6-yl]-2-methylamino-propionamide;

(S)—N-[1-(3-Chloro-phenyl)-3-(4,4-dimethyl-cyclohexyl)-2-oxo-1,2,3,4-tetrahydro-pyrido[3,2-d]pyrimidin-6-yl]-2-methylamino-propionamide;

(S)—N-[1-(3-Chloro-phenyl)-3-(1,2-dimethyl-propyl)-2-oxo-1,2,3,4-tetrahydro-pyrido[3,2-d]pyrimidin-6-yl]-2-methylamino-propionamide;

(S)—N-[1-(3-Chloro-phenyl)-3-(1-cyclobutyl-ethyl)-2-oxo-1,2,3,4-tetrahydro-pyrido[3,2-d]pyrimidin-6-yl]-2-methylamino-propionamide;

(S)—N-[3-(1-Acetyl-piperidin-4-yl)-1-(3-chloro-phenyl)-2-oxo-1,2,3,4-tetrahydro-pyrido[3,2-d]pyrimidin-6-yl]-2-methylamino-propionamide;

(S)—N-[1-(3-Chloro-phenyl)-2-oxo-3-(1,3,3-trimethyl-butyl)-1,2,3,4-tetrahydro-pyrido[3,2-d]pyrimidin-6-yl]-2-methylamino-propionamide;

(S)—N-[1-(4-Chloro-phenyl)-2-oxo-3-thiazol-4-ylmethyl-1,2,3,4-tetrahydro-pyrido[3,2-d]pyrimidin-6-yl]-2-methylamino-propionamide;

(S)—N-[1-(4-Chloro-phenyl)-2-oxo-3-phenethyl-1,2,3,4-tetrahydro-pyrido[3,2-d]pyrimidin-6-yl]-2-methylamino-propionamide;

(S)—N-[1-(3-Chloro-phenyl)-3-cyclopentylmethyl-2-oxo-1,2,3,4-tetrahydro-pyrido[3,2-d]pyrimidin-6-yl]-2-methylamino-propionamide;

N-(3-Benzyl-2-oxo-2,3-dihydro-1H-imidazo[4,5-b]pyridin-5-yl)-2-methylamino-propionamide hydrochloride;

(S)-2-Methylamino-N-(2-oxo-1,2,3,4-tetrahydro-pyrido[3,2-d]pyrimidin-6-yl)-propionamide hydrochloride;

(S)-2-Amino-N-[1-(4-chloro-phenyl)-3,3-diethyl-2-oxo-2,3-dihydro-1H-pyrido[2,3-b][1,4]oxazin-6-yl]-propionamide hydrochloride; and (S)-2-Amino-N-[1-(4-chloro-phenyl)-3,3-diethyl-2-oxo-2,3-dihydro-1H-pyrido[2,3-b][1,4]oxazin-6-yl]-propionamide (2,3,3,3-$d_4$) hydrochloride;

or tautomeric or stereochemically isomeric forms, N-oxides, pharmaceutically acceptable salts or the solvates thereof.

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

Salts, Solvates, Tautomers, Isomers, N-Oxides, Esters, Prodrugs and Isotopes

A reference to a compound of the formula (I) and sub-groups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-aminosalicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

If the compound is anionic, or has a functional group which may be anionic (e.g., —COON may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and preferably greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, certain heteroaryl rings can exist in the two tautomeric forms such as A and B shown below. For simplicity, a formula may illustrate one form but the formula is to be taken as embracing both tautomeric forms.

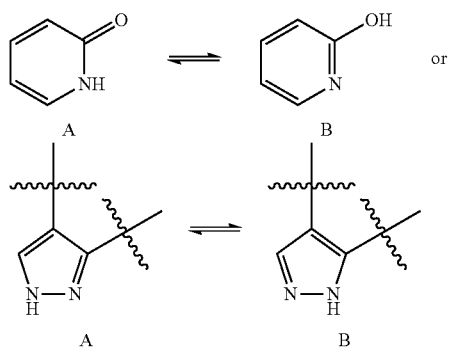

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

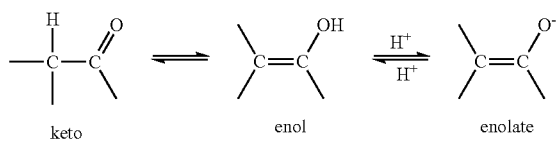

Stereoisomers

Unless otherwise mentioned or indicated, the chemical designation of compounds denotes the mixture of all possible stereochemically isomeric forms.

Stereocentres are illustrated in the usual fashion, using 'hashed' or 'wedged' lines. e.g.

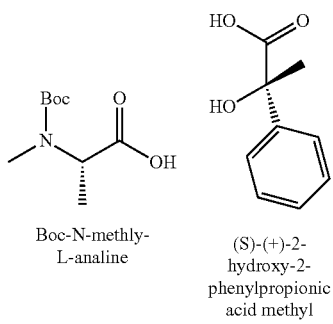

Where a compound is described as a mixture of two diastereoisomers/epimers, the configuration of the stereocentre is not specified and is represented by straight lines.

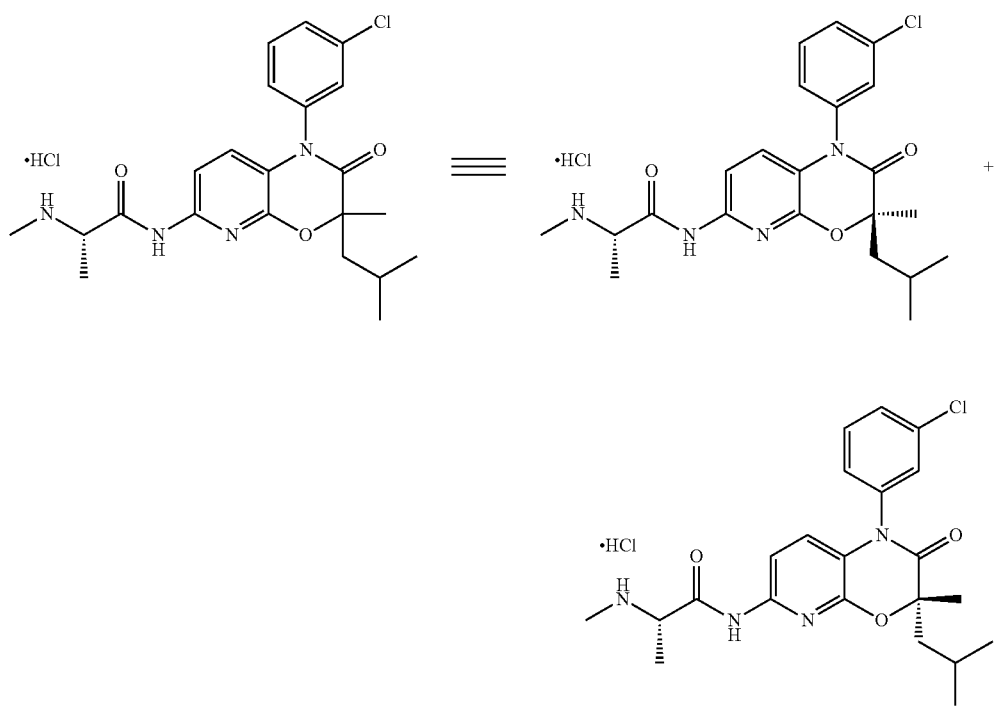

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(═O)OR, wherein R is an ester substituent, for example, a $C_{1-7}$alkyl group, a $C_{3-12}$ heterocyclyl group, or a $C_{5-12}$ aryl group, preferably a $C_{1-6}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-6}$ alkyl group, a $C_{3-12}$ heterocyclyl group, or a $C_{5-12}$ aryl group, preferably a $C_{1-6}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates had formed. Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I). For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu);
$C_{1-7}$aminoalkyl (e.g., aminoethyl; 2-(N,N-diethylamino)ethyl; 2-(4-morpholino)ethyl); and
acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Methods for the Preparation of Compounds of Formula (I)

In this section, as in all other sections of this application unless the context indicates otherwise, references to formula (I) also include all other sub-groups and examples thereof as defined herein.

Compounds of the formula (I) can be prepared in accordance with synthetic methods well known to the skilled person.

According to a further aspect of the invention there is provided a process for preparing a compound of formula (I) as hereinbefore defined which comprises:

(a)
(i) reacting a compound of formula (II):

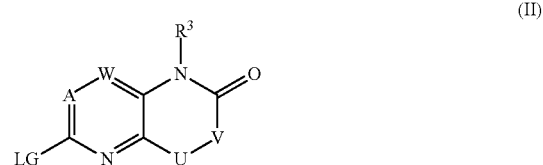

(II)

wherein A, U, V, W and $R^3$ are as defined hereinbefore for compounds of formula (I) and LG represents a suitable leaving group such as a triflate group or halogen atom e.g. Cl, Br, I, with a compound of formula (III), for example using transition metal (e.g. Pd or Cu) couplings:

(III)

wherein $R^1$ and $R^2$ are as defined hereinbefore for compounds of formula (I) and PG represents a suitable protecting group such as a tert-butyloxycarbonyl (tBoc), followed by a deprotection reaction suitable to remove the PG protecting group; or (ii) reacting a compound of formula (IV):

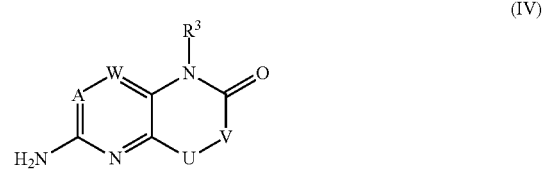

(IV)

wherein A, U, V, W and R³ are as defined hereinbefore for compounds of formula (I), with a compound of formula (V), for example using standard amide couplings:

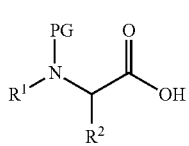
(V)

wherein R¹ and R² are as defined hereinbefore for compounds of formula (I) and PG represents a suitable protecting group such as a tert-butyloxycarbonyl (tBoc), followed by a deprotection reaction suitable to remove the PG protecting group; or (iii) compounds of formula (I) where at least one of U or V is not carbon can be synthesised by reacting a compound of formula (VI):

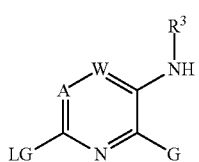
(VI)

wherein A, W and R³ are as defined hereinbefore for compounds of formula (I), G is $NH_2$, SH, OH, or $-CH_2NH_2$ and LG represents a suitable leaving group such as a triflate group or halogen atom e.g. Cl, Br, I, with a compound of formula (III), for example using transition metal (Pd or Cu) metal couplings:

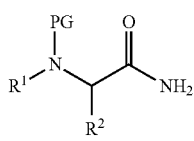
(III)

wherein R¹ and R² are as defined hereinbefore for compounds of formula (I) and PG represents a suitable protecting group such as a tert-butyloxycarbonyl (tBoc), followed by a deprotection reaction suitable to remove the PG protecting group, and then synthesising the second ring, for example using analogous methods to those described in Schemes 1, 2, 3, 5, 6 or 7; or (iv) compounds of formula (I) where at least one of U or V is not carbon can be synthesised by reacting a compound of formula (VII):

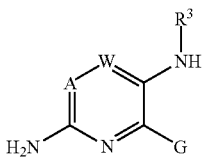
(VII)

wherein A, W, R³ are as defined hereinbefore for compounds of formula (I) and G is $NH_2$, SH, OH, or $-CH_2NH_2$, with a compound of formula (V), for example using standard amide couplings:

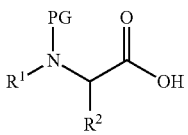
(V)

wherein R¹ and R² are as defined hereinbefore for compounds of formula (I) and PG represents a suitable protecting group such as a tert-butyloxycarbonyl (tBoc), followed by a deprotection reaction suitable to remove the PG protecting group, and then synthesising the second ring, for example using analogous methods to those described in Schemes 1, 2, 3, 5, 6 or 7; and/or (b) deprotection of a protected derivative of a compound of formula (I); and/or (c) interconversion of a compound of formula (I) or protected derivative thereof to a further compound of formula (I) or protected derivative thereof; and (d) optional formation of a pharmaceutically acceptable salt of a compound of formula (I).

The steps (a) (iii) and (a)(iv) the synthesis of the second ring can be carried out using methods well know in the art and the schemes below are illustrative of these techniques in particular Schemes 3 and 5. According to a further aspect, there is provided process for preparation of certain compounds of formula (I) according to the following schemes. Compounds where U is absent, V is NR⁵ and both a and W are CH can be prepared as outlined in Scheme 1:

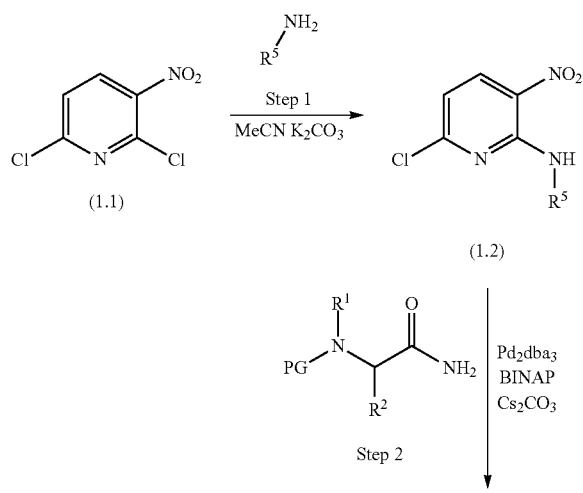

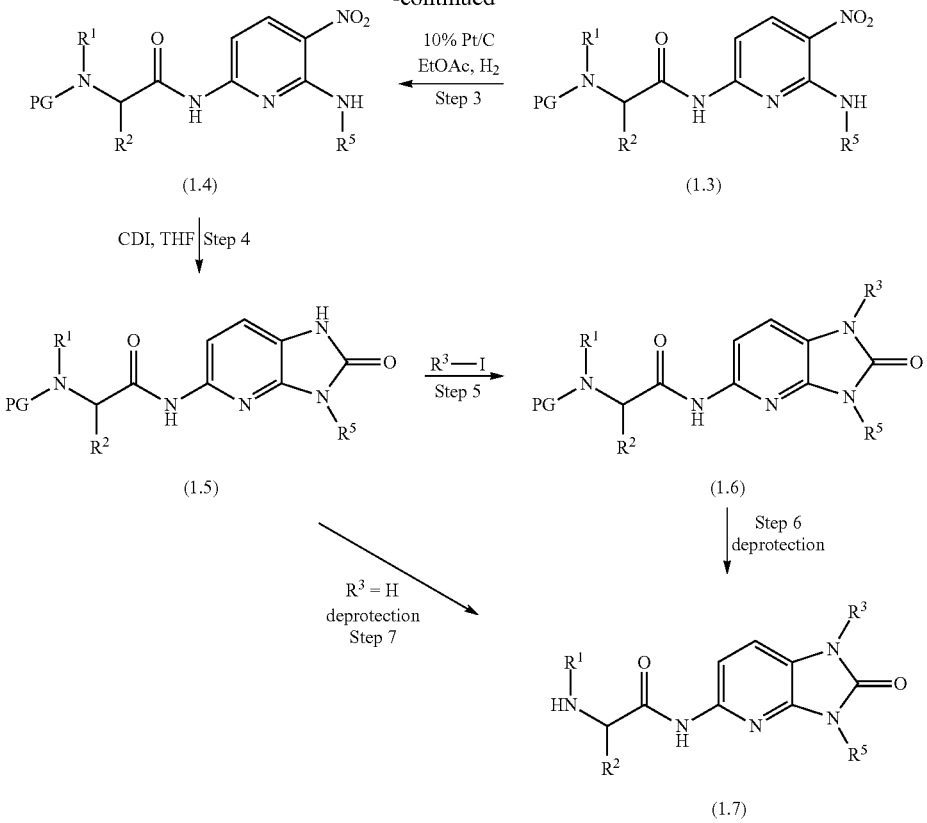

The appropriate amine R⁵NH₂ is added dropwise to a stirred, cooled (e.g. ~0° C.), solution of 2,6-dichloro-3-nitropyridine (1.1) with base (e.g. K₂CO₃) in solvent (e.g. acetonitrile) and then stirred for an appropriate time (e.g. 5 hours) at ambient temperature.

Step 2 can be performed using palladium-mediated amination procedures by following methods analagous to those described in the literature (S. Buchwald, J. Am. Chem. Soc., 2002, 6043). The compound (1.2) and an amide of formula R¹(PG)N—CHR²—C(=O)NH₂ [wherein PG represents a suitable protecting group such as CO—OC(CH₃)₃ (Boc), 2,4-dimethoxybenzyl (DMB), 4-methoxybenzyl (PMB), CO—OCH₂C₆H₅ (Cbz), CO—OC(CH₃)₂C₆H₄C₆H₅ (Bpoc), CO—OCH₂CH₂SiMe₃ (Teoc), CO—OCH₂CCl₃ (Troc), CO—OCH₂CHCH₂ (Alloc)] are treated with a palladium source [e.g. Pd₂dba₃ or Pd(OAc)₂] in the presence of a suitable ligand (e.g. Xantphos or BINAP) and base (Cs₂CO₃ or KOtBu) in a solvent (e.g. 1,4-dioxane, THF or toluene). The mixture is then heated (at e.g. 90° C.) in an inert atmosphere for an appropriate time (2-16 hours).

Compound (1.3) is then reduced to form the amine using, for example, 10% Pt/C under an atmosphere of hydrogen for 2 hours. Step 4 can then be performed by treatment of compound (1.4) with a suitable reagent [e.g. N,N'-carbonyldiimidazole (CDI) in a solvent (e.g. THF) and heating for an appropriate time (e.g. 70° C. for 3 hours). Alternative reagents to effect Step 4 may include triphosgene (bis(trichloromethyl)carbonate), or phosgene, in the presence of a non-interfering base (e.g. triethylamine) in a solvent such as dichloromethane at, or below, ambient temperature.

The required R³ group can be introduced in Step 5 by arylation of the amide nitrogen using, for example, an appropriate aryl iodide in the presence a copper salt (e.g. CuI), a suitable ligand (e.g. N,N'-dimethylethylenediamine) and a base (e.g. CsF) in a polar aprotic solvent such as MeCN. Alternatively, the required R³ group can be introduced by alkylation of the amide nitrogen using an appropriate alkylating agent [R³-LG, where LG represents a leaving group such as halogen, methanesulfonyloxy (OMs), p-toluenesulfonyloxy (OTs) or trifluoromethanesulfonyloxy (OTf)] in the presence of base (e.g. NaH) in a polar aprotic solvent such as MeCN.

The protecting group (PG) in compound (1.5) and (1.6) can then be removed. For example, the tert-butoxycarbonyl (Boc) protecting group can be removed in the presence of an acid [e.g. HCl (as a solution in EtOAc) or TFA]

Where A and/or W are other than CH, an analagous process to that shown in Scheme 1 can be followed using a compound of formula (1.8) shown below. Compounds of formula (1.8) can be prepared by following methods analagous to those described in the literature.

(1.8)

Alternatively, compounds where U is absent, V is NR⁵ and both A and W are CH can be prepared as outlined in Scheme 2.

Scheme 2

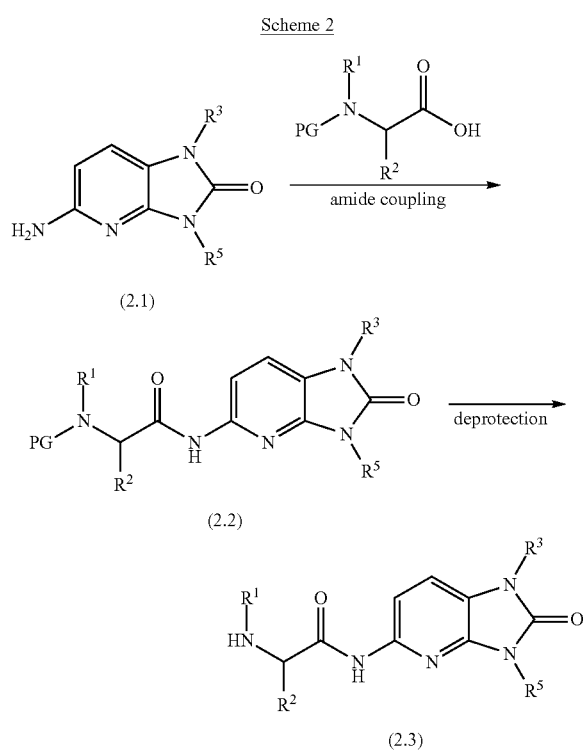

An amine of formula (2.1) can be coupled with $R^1(PG)N$—$CHR^2$—$C(=O)OH$ (where PG is defined previously) (e.g. Boc-N-methyl-L-alanine) using an amide coupling procedure (e.g. as described below). Subsequent removal of the protecting group (e.g. Boc) affords the product (2.3). Compounds of formula (2.1) can be prepared by following methods analagous to those described in the literature. One such example includes 5-amino-1,3-dimethyl-1,3-dihydro-imidazo[4,5-b]pyridin-2-one (Russian Journal of Organic Chemistry, 2007, 43, 11, 1706-1709), in which $R^3$ and $R^5$ are methyl.

The coupling reaction between the carboxylic acid $R^1(PG)N$—$CHR^2$—$C(=O)OH$ and the amine is preferably carried out in the presence of a reagent of the type commonly used in the formation of peptide linkages. Examples of such reagents include phosphonium-based coupling agents such as 1-benzo-triazolyloxytris-(pyrrolidino)phosphonium hexafluorophosphate (PyBop) and bromo-tris-pyrrolidino phosphoniumhexafluorophosphate (PyBrop) (Castro et al, Tetrahedron Letters, 1990, 31, 205), 1,3-dicyclohexylcarbodiimide (DCC) (Sheehan et al, J. Amer. Chem Soc. 1955, 77, 1067), 1-ethyl-3-(3'-dimethylaminopropyl)-carbodiimide (referred to herein either as EDC or EDAC but also known in the art as EDCI and WSCDI) (Sheehan et al, J. Org. Chem., 1961, 26, 2525), and uronium-based coupling agents such as 0-(7-azabenzotriazol-1-yl)-N,N,N',N'-tetramethyluronium hexafluorophosphate (HATU). Carbodiimide-based coupling agents are advantageously used in combination with 1-hydroxy-7-azabenzotriazole (HOAt) (L. A. Carpino, J. Amer. Chem. Soc., 1993, 115, 4397) or 1-hydroxybenzotriazole (HOBt) (Konig et al, Chem. Ber., 103, 708, 2024-2034). The coupling reaction is typically carried out in a non-aqueous, non-protic solvent such as acetonitrile, 1,4-dioxane, dimethylsulfoxide, dichloromethane, dimethylformamide or N-methyl-2-pyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulfonamide groups) at an appropriately elevated temperature. The reaction may be carried out in the presence of a non-interfering base, for example a tertiary amine such as triethylamine or N,N-diisopropylethylamine. For example the appropriate carboxylic acid and amine (free base or TFA-salt) can be coupled using PyBop (1.5 mol. eq.) in the presence of N,N-diisopropylethylamine at ambient temperature. Alternatively, the appropriate carboxylic acid and amine (free base or TFA-salt) can be coupled using HATU (3 mol. eq.) in the presence of N,N-diisopropylethylamine at ambient temperature for between 24-36 hours and then concentrated in vacuo. As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine and a solvent (e.g. dichloromethane).

Where A and/or W are other than CH, an analagous process to that shown in Scheme 2 can be followed using a compound of formula (2.4) shown below. Compounds of formula (2.4) can be prepared by following methods analagous to those described in the literature.

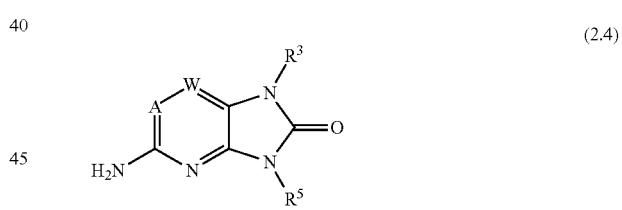

Compounds where U is O, V is $CR^4{}'R^4$ and both A and W are CH can be synthesised as outlined in Scheme 3.

Scheme 3

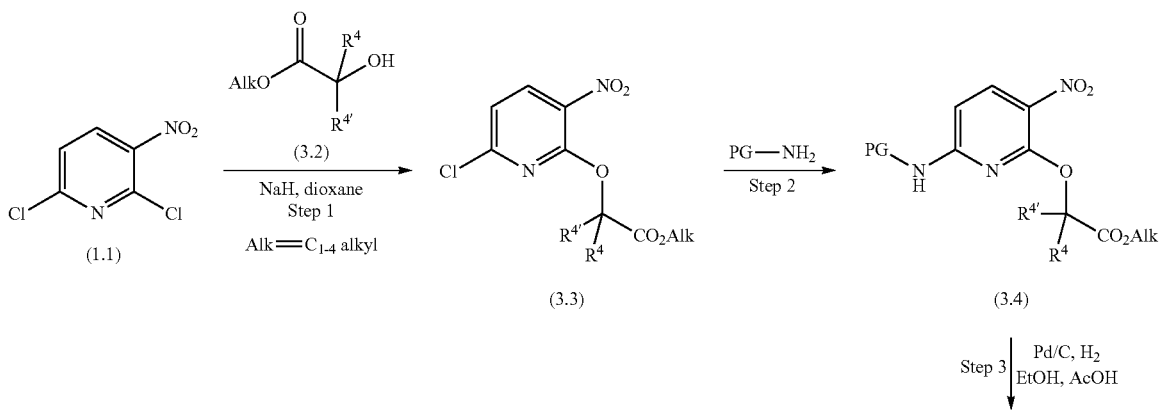

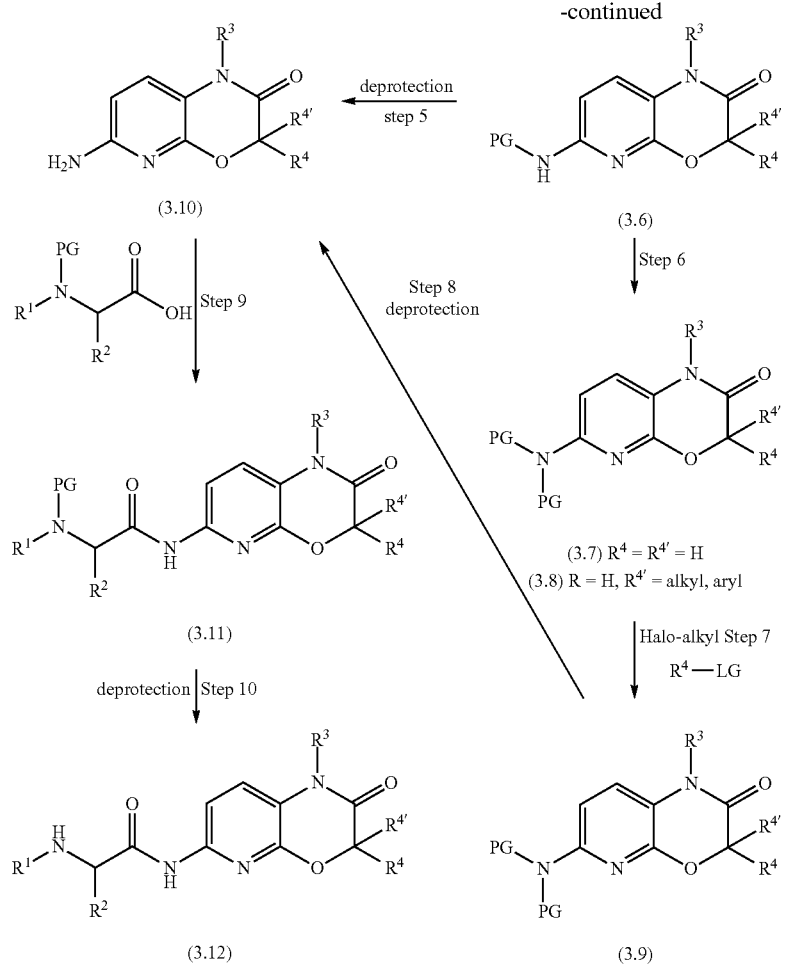
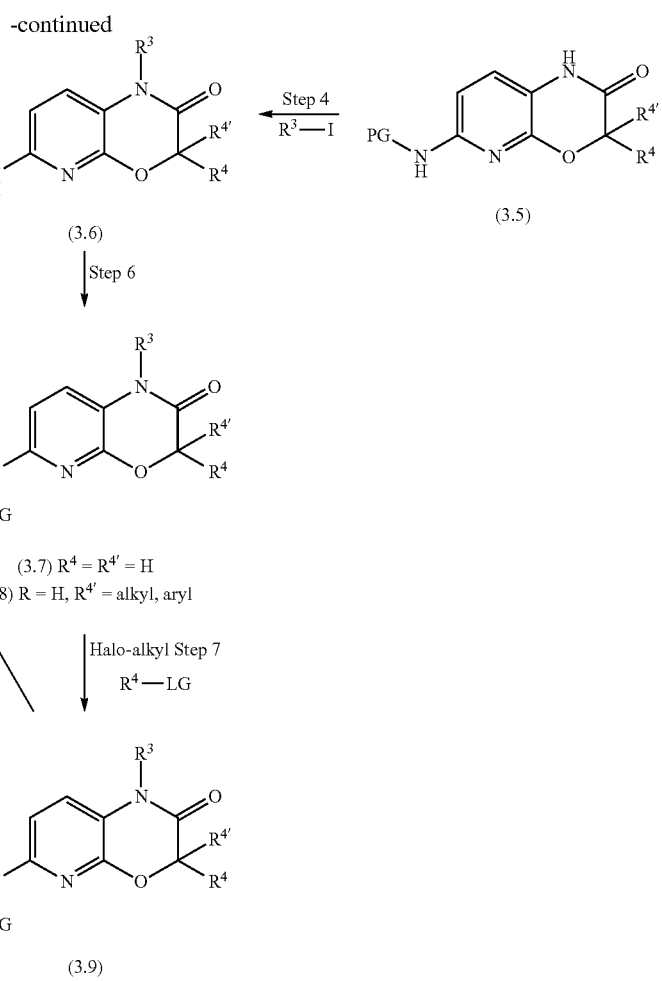

Step 1 can be performed by treating the appropriate hydroxyl ester (3.2), together with a base [e.g. NaH (60% dispersion in oil)] and a suitable solvent (e.g. 1,4-dioxane), with compound (3.1). Step 2 is then performed by treating compound (3.3) with an appropriate amine PG-NH$_2$(wherein PG is defined as above) (such as 2,4-dimethoxybenzylamine) in the presence of base (e.g. triethylamine). Step 3 (reduction of the nitro group, and successive cyclisation to afford the oxazinone) can then be achieved under appropriate reducing conditions. Such conditions could include catalytic hydrogenation using a suitable catalyst (e.g. 10% Pd/C) in a solvent (e.g. EtOH or MeOH) and, optionally, in the presence of an acid (e.g. AcOH). Alternative conditions could include heating in the presence of a metal (e.g. iron powder) in an acid (e.g. AcOH).

The required R$^3$ group can be introduced by arylation of the amide nitrogen using, for example, an appropriate aryl halide (e.g. 4-iodo-chlorobenzene) in the presence a copper salt (e.g. CuI), a suitable ligand (e.g. N,N'-dimethylethylenediamine) and a base (e.g. CsF) in a polar aprotic solvent such as MeCN.

Alternatively, the required R$^3$ group can be introduced by alkylation of the amide nitrogen using an appropriate alkylating agent (R$^3$-LG; where R$^3$ and LG are defined above) in the presence of base (e.g. NaH) in a polar aprotic solvent such as MeCN.

The desired functionality at R$^4$ and R$^{4'}$ can be introduced by use of an appropriately functionalised α-hydroxy-ecetate ester (glycolate) (3.2) in Step 1 such as (R)-2-hydroxy-propionic acid methyl ester, (S)-2-hydroxy-3-phenyl-propionic acid or (S)-(+)-2-hydroxy-2-phenylpropionic acid methyl ester.

Alternatively R$^4$ and/or R$^{4'}$ can be introduced in Step 7 to give compounds of formula (3.9).

Compound (3.9), where R$^4$=alkyl or aryl and R$^{4'}$=H, can be prepared by derivatisation of compound (3.7) which, itself, can be prepared by using ethyl glycolate in Step 1 and introduction of a suitable protecting group (e.g. Boc) in Step 6. Compound (3.7) is treated with a strong base (e.g. LiHMDS or LiO$^t$Bu or KO$^t$Bu) in an aprotic solvent (e.g. THF) at a suitable temperature (e.g. −78° C.) for an appropriate time (e.g. 15 minutes), in order to form the corresponding enolate. A compound of formula R$^4$-LG (where LG is defined above) can then be added and the mixture allowed to warm to an appropriate temperature (e.g. ambient temperature) over a suitable period of time (e.g. 15 minutes).

Compounds where R$^4$=aryl could be prepared by adding a diaryliodonium salt (e.g. diphenyliodonium bromide) to the enolate, instead of R$^4$-LG. Alternatively, compounds where R$^4$=aryl could also be prepared by adding a compound of formula R$^4$-LG (e.g. bromobenzene) to the enolate, together with a suitable palladium source [e.g. Pd(OAc)$_2$] and ligand (e.g. Q-Phos) and stirring in an appropriate solvent (e.g. toluene) at a suitable temperature (e.g. ambient temperature −80° C.). (C. Johansson, *Angew Chem, In Ed.* 2010, 49, 676).

Compounds where both $R^4$ and $R^{4'}$ are alkyl and/or aryl can be prepared by following the procedures above, using stoichiometric amounts of $R^4$-LG, isolating the product, and then repeating the procedures using a stoichiometric amount of base and $R^{4'}$-LG.

Compounds where $R^4$=$R^{4'}$=alkyl can be prepared by using ≥2 mol. equivalents of both base and $R^4$-LG.

In an analogous manner, compounds where $R^4$ and $R^{4'}$ group join to form a ring can be synthesised by reacting compound (3.7) with dihalo compounds such as 1,5-diiodopentane, 1,4-diiodobutane or 1,2-bis-bromomethyl-benzene.

In addition, compounds where $R^4$ and $R^{4'}$ are different can also be prepared by derivatisation of compound (3.8). Compound (3.8) can be prepared by using an appropriately functionalised α-hydroxy-ecetate ester (glycolate) (3.2) [e.g. (R)-2-hydroxy-propionic acid methyl ester ($R^{4'}$=Me)] in Step 1, followed by introduction of a suitable protecting group (e.g. Boc) in Step 6.

Compound (3.8) is treated with a strong base (e.g. LiHMDS or LiO$^t$Bu or KO$^t$Bu) followed by addition of a suitable electrophile $R^4$-LG using methods analogous to those described above.

The conditions for deprotection of compounds (3.6) and (3.9) (Steps 5 and 8 respectively) will depend upon the nature of the protecting group. For example, when the protecting group represents Boc or 2,4-dimethoxybenzyl, such a deprotection reaction will typically comprise the use of a suitable acid in a suitable solvent. For example, the acid may suitably comprise trifluoroacetic acid or hydrogen chloride and the solvent may suitably comprise dichloromethane ethyl acetate, 1,4-dioxane, methanol or water.

Compounds of formula (3.10) may then be coupled with compounds of formula $R^1$(PG)N—CHR$^2$—C(=O)OH (e.g. Boc-N-methyl-L-alanine) using standard amide coupling procedures described in Scheme 2.

Final deprotection of compound (3.11) can be performed using methods analagous to those described for compounds (3.6) and (3.9)

Where A and/or W are other than CH, an analagous process to that shown in the Schemes above can be followed, starting with a compound of formula (1.8) as defined above.

Compounds where either U=CH$_2$ or absent, and V=CR$_4$R$_{4'}$ can be prepared as outlined in Scheme 4

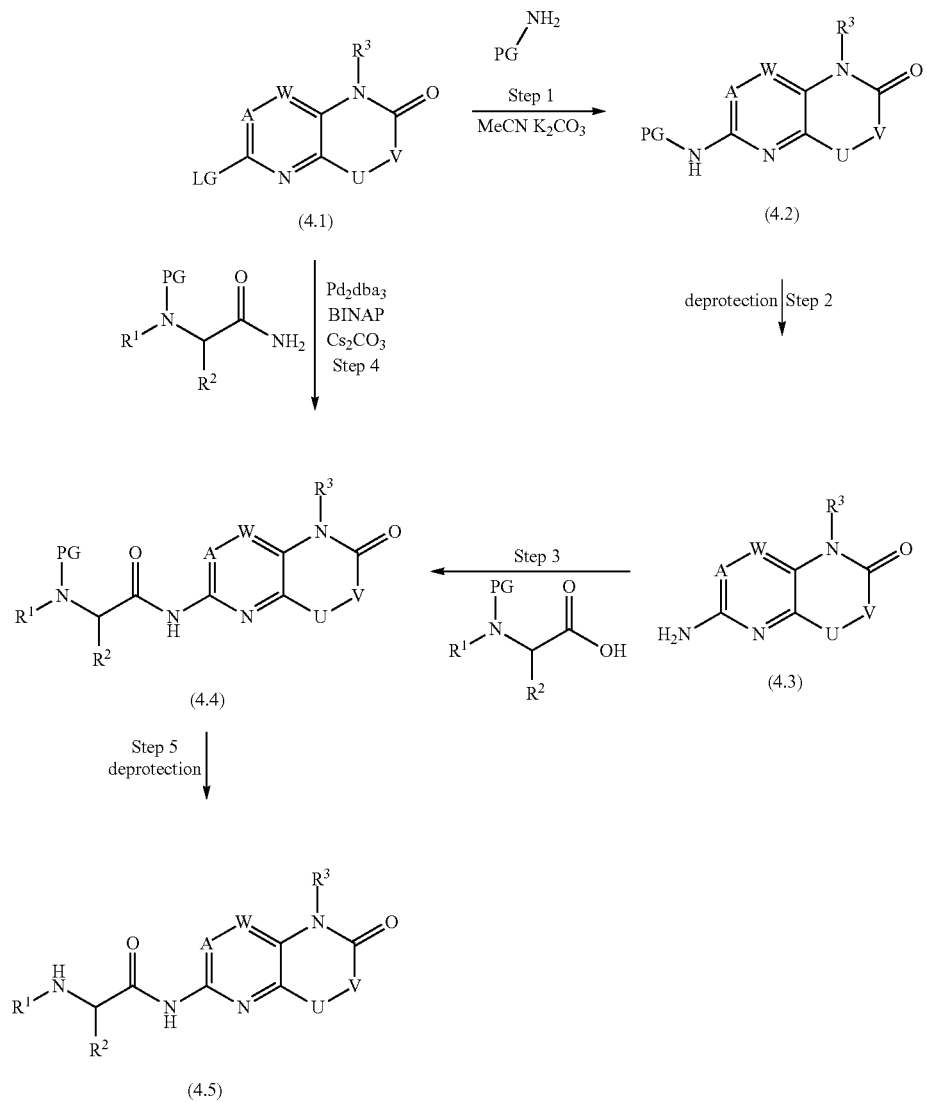

The appropriate amine PG-NH$_2$ (wherein PG is as defined above) (e.g. 2,4-dimethoxybenzylamine) is added dropwise to a stirred, cooled (e.g. ~0° C.), solution of compound (4.1) in the presence of base (e.g. K$_2$CO$_3$) in solvent such as acetonitrile and then stirred for an appropriate time (e.g. 5 hours) at a suitable temperature (ambient temperature-reflux). Compounds of formula (4.1) are commercially available or can be prepared by following methods analogous to those described in the literature.

Alternatively, the appropriate compound of formula R$^1$(PG)N—CHR$^2$—C(O═)NH$_2$ can be introduced using a palladium mediated coupling reaction (amination) (Step 4) in an analogous fashion to that described in Scheme 1.

The deprotection and coupling (Step 2 and 3 respectively) can be performed by following methods analogous to those described in Scheme 3.

The protecting group (PG) in compound (4.4) can be can then be removed by following methods similar to those described in Scheme 3.

Compounds where U is NH and V is CR$^{4'}$R$^4$ and both A and W are CH can be synthesised as described in Scheme 5.

The appropriate α-amino acid derivative and base (e.g. triethylamine) are added to 2,6-dichloro-3-nitro-pyridine (5.1) in an aprotic solvent and the reaction mixture stirred at ambient temperature. The α-amino acid derivative may be, for example, glycine ethyl ester hydrochloride (where R$^4$═R$^{4'}$═H) or L-alanine methyl ester hydrochloride (where R$^4$═Me, R$^{4'}$═H).

Step 2 can be performed by treatment of compound (5.2) with an appropriate amine PG-NH2 (wherein PG is as defined above; e.g. 4-methoxybenzylamine) at a suitable temperature (e.g. ambient temperature). Step 3 and Step 4 can then be performed as described in Scheme 3. Reduction of the nitro group, and in situ cyclisation, (Step 5) can then be performed, for example, by hydrogenation in the presence of Pd—C in a suitable solvent (e.g. MeOH/THF mixture).

The required R$^3$ group can be introduced by arylation or alkylation, following methods analogous to those described in Scheme 1. Step 7 and Step 8 (removal of protecting groups) can then be performed by following similar methods to those described in Scheme 3.

Where A and/or W are other than CH, an analagous process to that shown in the Schemes above can be followed, starting with a compound of formula (1.8) as defined above.

Compounds where U is CH$_2$ and V is NR$^5$ and both A and W are CH can be synthesised as described in Scheme 6.

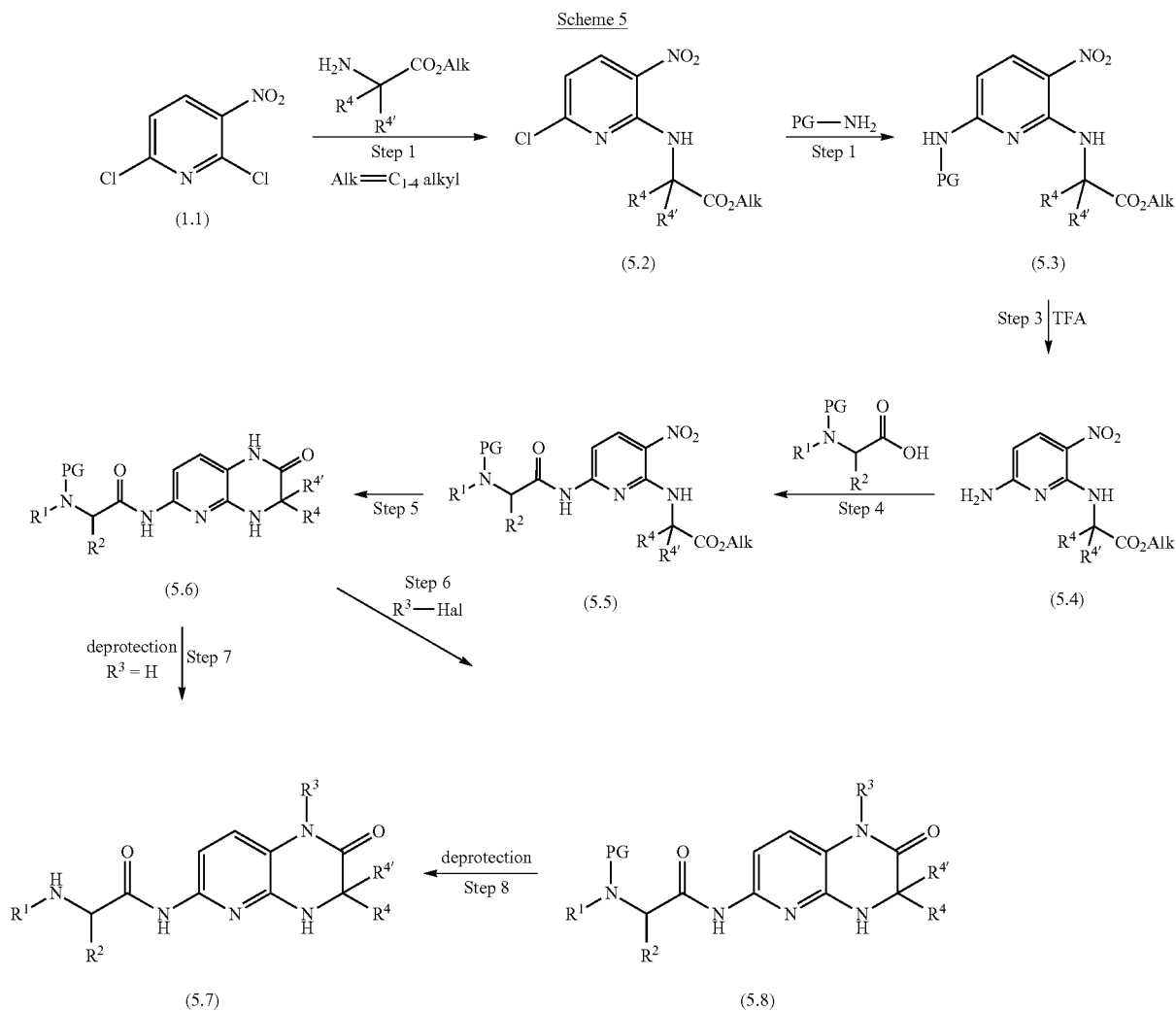

Scheme 6

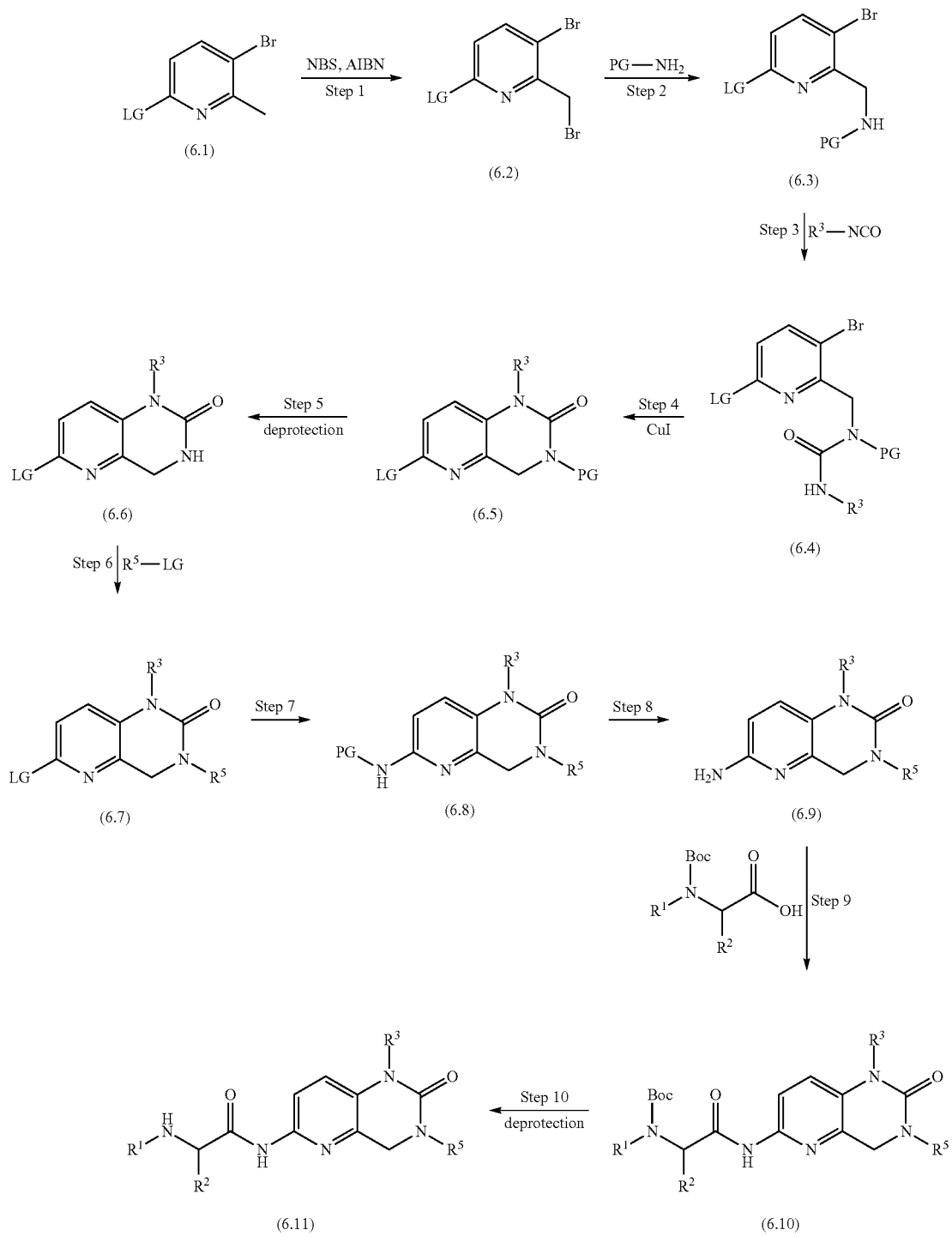

Compound (6.1) can be halogenated (e.g. using N-bromosuccinimide/2,2'-azobis(2-methylpropionitrile in CCl₄ at reflux). The halide (6.2) can then be substituted with an appropriate amine PG-NH₂ (wherein PG is defined above; e.g. 4-methoxybenzylamine). Preparation of the urea (6.4) (Step 3) can be performed using standard methods well described in the literature. For example, such compounds can be prepared by reacting the amine with a suitably substituted isocyanate, of the formula $R^3$—N=C=O, in a solvent (e.g. DMF or DCM) at ambient temperature. In one example, the amine and a base (e.g. N,N-diisopropylethylamine) in dichloromethane are treated with phenyl-isocyanate ($R^3$=Ph) and the mixture stirred at ambient temperature.

Cyclisation to afford compound (6.5) (Step 4) can be performed in the presence of a suitable metal catalyst [e.g. CuI or Pd(OAc)₂ (in the presence of a ligand such as BINAP)]

together with a base (e.g. N,N-diisopropylethylamine) in an aprotic solvent (e.g. DMF). The protecting group is then removed (Step 5) under acidic conditions (e.g. TFA) to unmask the cyclic urea (6.6) which can then be further derivatised to allow introduction of the $R^5$ group. The appropriate $R^5$ group can be introduced in Step 6 by using arylation and alkylation methods similar to those described in Scheme 1.

Step 7 can be performed by treatment of compound (6.7) with an appropriate amine $PG-NH_2$ (wherein PG is described as above; e.g. 2,4-dimethoxybenzylamine or 4-methoxybenzylamine). Deprotection (Step 8), amide coupling (Step 9) and final deprotection (Step 10) can then be performed as described in Scheme 3, to give compounds of formula I.

Where A and/or W are other than CH, an analagous process to that shown in Schemes above can be followed using a compound of formula (6.12) shown below. Compounds of formula (6.12) can be prepared by following methods analagous to those described in the literature.

Alternatively, compounds where U is $CH_2$, V is $NR^5$ and both A and W are CH can be synthesised as described in Scheme 7.

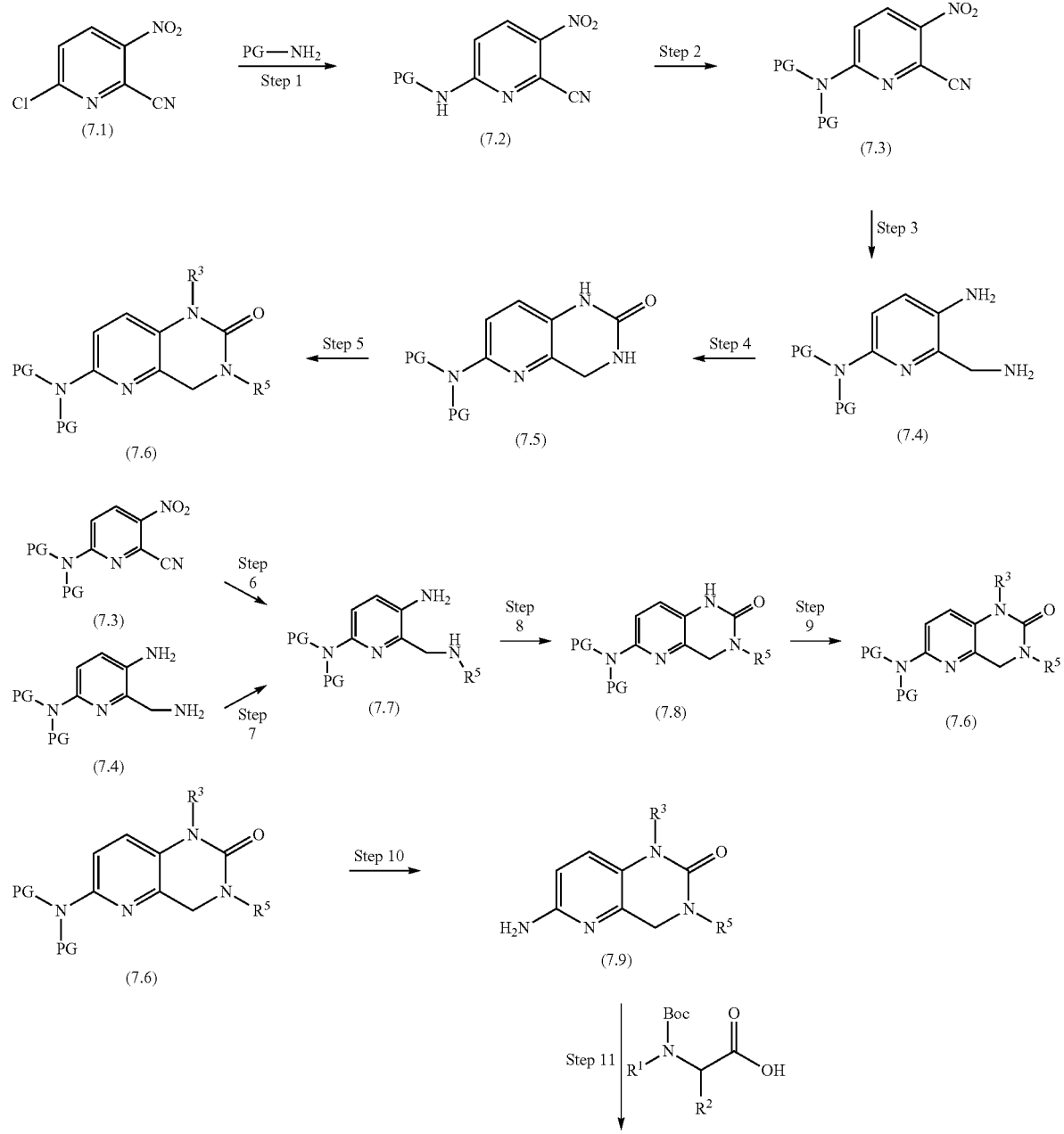

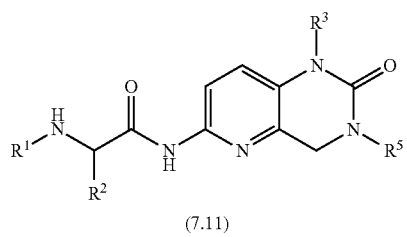 (7.11)

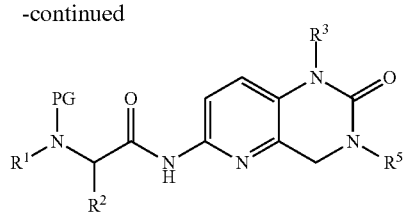 (7.10)

To compound (7.1) and base (e.g. triethylamine) in protic solvent (e.g. ethanol) is added dropwise the appropriate amine PG-NH$_2$ (wherein PG is as defined above; e.g. 2,4-dimethoxybenzylamine). The product (7.2) is then further protected (e.g. with Boc or DMB). Compound (7.3) can then be reduced by, for example, hydrogenation in the presence of a suitable catalyst (e.g. Pd—C) to give the diamine (7.4). Subsequent cyclisation to afford the cyclic urea (7.5) can be achieved by using standard methods which are well described in the literature (e.g. using N,N'-carbonyldiimidazole in THF). Alternative reagents to effect Step 4 include triphosgene (bis(trichloromethyl)carbonate), or phosgene, in the presence of a non-interfering base (e.g. triethylamine) in a solvent such as dichloromethane at, or below, ambient temperature.

The appropriate R$^3$ and R$^5$ groups can be introduced in Step 5 by arylation or alkylation using methods similar to those described in Scheme 1. Where R$^3$ and R$^5$ are the same, the groups may be introduced in a single Step. Where R$^3$ and R$^5$ are different, the groups may be introduced successive arylation and/or alkylation steps.

For compounds where R$^3$ and R$^5$ are both hydrogen, Step 5 is omitted.

Alternatively R$^5$ can be introduced in Step 6 by treatment of compound (7.3) with an appropriate aldehyde or ketone under reducing conditions (e.g. catalytic hydrogenation conditions using Pd—C). The resulting product from this reaction is then treated with a suitable reducing agent [e.g. NaB(OAc)$_3$H, or NaB(CN)H$_3$] in a solvent such as 1,2-dichloroethane. Further aldehyde or ketone can be added as necessary to ensure completion of the reaction Alternatively R$^5$ can be introduced in Step 7 by treatment of the diamine (7.4) with an appropriate aldehyde or ketone together with a suitable reducing agent [e.g. NaB(OAc)$_3$H, or NaB(CN)H$_3$] in a suitable solvent (e.g. 1,2-dichloroethane).

The alkylated diamines obtained using these methods can then be cyclised to form the urea (7.8) as described above. R$^3$ groups can then be introduced is desired as described herein.

The deprotection and amide coupling steps (Steps 10-12) can then be performed as described in Schemes 3 above.

Where A and/or W are other than CH, an analogous process to that shown in Schemes above can be followed using a compound of formula (7.12) shown below. Compounds of formula (7.12) can be prepared by following methods analagous to those described in the literature.

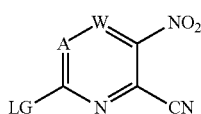 (7.12)

Amines of the formula H$_2$N—R$^5$ can be obtained from commercial sources or can be prepared by any of a large number of standard synthetic methods well known those skilled in the art, see for example see Advanced Organic Chemistry by Jerry March, 4th Edition, John Wiley & Sons, 1992, and Organic Syntheses, Volumes 1-8, John Wiley, edited by Jeremiah P. Freeman (ISBN: 0-471-31192-8), 1995, and see also the methods described in the experimental section below. Alternatively the appropriate nitro-compound can be reduced to give the corresponding amino-compound. The reduction may be carried out by standard methods such as catalytic hydrogenation, for example in the presence of palladium on carbon in a polar solvent such as ethanol or dimethylformamide at room temperature. As an alternative, reduction may be effected using a reducing agent such as tin (II) chloride in ethanol, typically with heating, for example to the reflux temperature of the solvent.

The required carboxylic acids R$^1$(PG)N—CHR$^2$—C(=O)OH (wherein PG is as defined previously) can be obtained commercially (e.g. appropriately protected or derivatised amino acids) or can be synthesised according to methods well known to the skilled person, see for example Advanced Organic Chemistry and Organic Syntheses, the details for which are given above. For example, compounds where R$^2$=alkyl, alkenyl, haloalkyl or cycloalkyl can be prepared by alkylation of a suitably protected glycine derivative (e.g. using KO$^t$Bu and iodoethane) or by using methods based on the Strecker synthesis (Harld Groger, Chem. Rev. 2003, 103, 2795). Alternatively, compounds of this type can be prepared using methodology based on chiral auxiliaries such as dioxopiperazine (Scholkopf) or benzyl (2R,3S)-6-oxo-2,3-diphenyl-4-morpholinecarboxylate intermediates (Williams) (Chiral Auxiliaries and Ligands in Asymmetric synthesis; J. Seyden-Penne, Publisher: John Wiley, 1995).

Further compounds (e.g. R$^2$=haloalkyl) could be prepared by functional group interconversion (FGI) of suitably protected amino acids such as serine. For example fluoroalanine analogues can be prepared in this way (H. R. Hoveyda et. al.; Org. Lett, 2006, 5849).

R$^1$ could be introduced by alkylation of compounds with the formula NH$_2$—CHR$^2$—C(=O)OMe with aldehydes and ketones (e.g. cyclohexanone) in the presence of a reducing agent (e.g. NaB(OAc)$_3$H) in solvent such as 1,2-dichloroethane. Alternatively, compounds with the formula (PG)NH—CHR$^2$—C(=O)OMe could be alkylated with the appropriate alkylating agent (R$^1$-LG, e.g. iodoethane) in the presence of a base (e.g. NaH) in a polar aprotic solvent (e.g. DMF).

Appropriate amides e.g. of formula R$^1$(PG)N—CHR$^2$—C(=O)NH$_2$ can be prepared from the corresponding carboxylic acids using EDC, HOAt and ammonium hydrogencarbonate at ambient temperature overnight.

A wide range of well known functional group interconversions are know by a person skilled in the art for converting a precursor compound to a compound of formula I and are described in Advanced Organic Chemistry by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in Scheme 1-5 are followed or preceded by one or more reactions known to the skilled of the art and are performed in an appropriate order to achieve the requisite substitutions on $R^1$, $R^2$, $R^3$, $R^4$, $R^5$, and $R^6$, defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

The compounds of formula (III) and (V) may be prepared in accordance with procedures apparent to the skilled person, such as those described herein. Compounds (III) and (V) are commercially available, known in the literature or can be prepared by methods analogous to those described in the literature or by methods similar to that described in the example experimental procedures below.

In a further embodiment the invention provides a novel intermediate. In one embodiment the invention provides a novel intermediate of formula (II), (IV), (VI) and (VII).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(═O)R), for example, as: a t-butyl ether; a tetrahydropyranyl (THP) ether; a benzyl, benzhydryl (diphenylmethyl), or trityl (triphenylmethyl)ether; a trimethylsilyl or t-butyldimethylsilyl ether; or an acetyl ester (—OC(═O)CH$_3$).

An aldehyde or ketone group may be protected, for example, as an acetal (R—CH(OR)$_2$) or ketal (R$_2$C(OR)$_2$), respectively, in which the carbonyl group (>C═O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH-Psec).

For example, in Scheme 1 above, the moiety R$_1$NH—CHR$_2$—C(═O)NH$_2$ contains two amino groups, the first amino group R$_1$NH— can be protected by means of a protecting group as hereinbefore defined, one preferred group being the tert-butyloxycarbonyl (Boc) group while the second amide NH$_2$ is introduced. Where no subsequent modification of the amino group is required, the protecting group can be carried through the reaction sequence to give an N-protected form of a compound of the formula (I) which can then be de-protected by standard methods (e.g. treatment with acid in the case of the Boc group) to give the compound of formula (I).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an $C_{1-7}$ alkyl ester (e.g., a methyl ester; a t-butyl ester); a $C_{1-7}$ haloalkyl ester (e.g., a $C_{1-7}$ trihaloalkyl ester); a tri$C_{1-7}$alkylsilyl-$C_{1-7}$alkyl ester; or a $C_{5-20}$ aryl-$C_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(═O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

The compounds of the invention, subgroups and examples thereof, are antagonists of inhibitor of apoptosis protein (IAP), and which may be useful in preventing or treating disease states or conditions described herein. In addition the compounds of the invention, and subgroups thereof, will be useful in preventing or treating diseases or condition mediated by IAP. References to the preventing or prophylaxis or treatment of a disease state or condition such as cancer include within their scope alleviating or reducing the incidence of cancer.

Thus, for example, it is envisaged that the compounds of the invention will be useful in alleviating or reducing the incidence of cancer.

The compounds of the present invention may be useful for the treatment of the adult population. The compounds of the present invention may be useful for the treatment of the pediatric population.

More particularly, the compounds of the formula (I) and sub-groups thereof are antagonists of IAP. For example, compounds of the invention have affinity against XIAP, cIAP1 and/or cIAP2, and in particular an IAP selected from XIAP and cIAP1.

Preferred compounds are compounds that have affinity for one or more IAP selected from XIAP, cIAP1 and cIAP2. Preferred compounds of the invention are those having $IC_{50}$ values of less than 0.1 µM.

The antagonist compounds of formula (I) are capable of binding to IAP and exhibiting potency for IAP. In one embodiment the antagonist compounds of formula (I) exhibit selectivity for one or more IAP over other IAP family members, and may be capable of binding to and/or exhibiting affinity for XIAP and/or cIAP in preference to binding to and/or exhibiting affinity for other of the IAP family members.

In addition many of the compounds of the invention exhibit selectivity for the XIAP compared to cIAP or vice versa, selectivity for the cIAP compared to XIAP (in particular cIAP1), and such compounds represent one embodiment of the invention. In particular compounds of the invention may have at least 10 times greater affinity against one or more IAP family member in particular XIAP, cIAP1 and/or cIAP2 than other IAP family members. This can be determined using the methods described herein. In a further embodiment compounds of the invention may have equivalent affinity for XIAP, cIAP1 and/or cIAP2, in particular equivalent affinity (i.e. less than 10-fold difference in affinity) for XIAP and cIAP1.

Activity against XIAP and cIAP may be particularly advantageous. Antagonising XIAP and cIAP1/2 with equipotency should enable triggering of apoptosis via activation of caspase-8 and the switch away from pro-survival NF-kappaB signalling towards apoptosis; and potent antagonism of XIAP will ensure that apoptosis is achieved before any inherent resistance mechanism is upregulated to block the process. On depletion of cIAP1/2 via autoubiquitination and proteasomal degradation there is a temporary upregulation of NF-kappaB signalling that is responsible for expression of TNF-alpha in sensitive cell lines—this is also responsible for upregulation of anti-apoptotic factors such as cIAP2 and c-FLIP. Hence the need for potent XIAP antagonism to potentiate effector caspase activation and cell death, rather than allowing cIAP1/2 antagonism-mediated resistance to build up. It is generally believed that toxicities that arise on dosing these compounds in vivo will arise from the temporary induction of NFkappaB signalling and resultant upregulation of pro-inflammatory cytokines, which is mediated solely by cIAP1/2 antagonism. Therefore dual potency should enable a therapeutic window to be achieved before dose-limiting toxicities are achieved.

IAP function in controlling programmed cell death has also been implicated in many diseases, including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

Therefore, it is also envisaged that the compounds of the invention may be useful in treating other conditions such as inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

As a consequence of their affinity for IAP, the compounds will be useful in providing a means of controlling programmed cell death. It is therefore anticipated that the compounds may prove useful in treating or preventing proliferative disorders such as cancers. In addition, the compounds of the invention may be useful in the treatment of diseases in which there is a disorder associated with cell accumulation or where excessive apoptosis results in cell loss.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer. Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

In one embodiment the haematological malignancies is leukaemia. In another embodiment the haematological malignancies is lymphoma.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours i.e. tumours that have formed from malignant cells which have circulated through the bloodstream (haematogenous spread) or via lymphatics or across body cavities (trans-coelomic) to other sites and tissues in the body.

Particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

Particular cancers include renal, melanoma, colon, lung, breast, ovarian and prostate cancers. In one embodiment the cancer is selected from melanoma, colon, breast and ovarian. In one embodiment the cancer is melanoma. In one embodiment the cancer is inflammatory breast cancer.

A further aspect of the invention includes a compound of the invention for use in the prophylaxis or treatment of cancer in a patient selected from a sub-population possessing cancers with a high inflammatory component. Such cancers are also known as "inflammatory phenotype" and include tumours with elevated cytokine signalling (e.g. TNF). In one embodiment the cancer is an inflammatory tumour, for example, melanoma, colon, breast and ovarian, in particular, melanoma.

In one embodiment the disease to be treated is leukaemia, such as acute and chronic leukaemias, acute myeloid leukaemia (AML), and chronic lymphocytic leukaemia (CLL). In one embodiment the leukaemia is refractory DLBCL.

In one embodiment the cancer is mesothelioma including malignant peritoneal mesothelioma or malignant pleural mesothelioma.

Certain cancers are resistant to treatment with particular drugs. This can be due to the type of the tumour (most common epithelial malignancies are inherently chemoresistant) or resistance can arise spontaneously as the disease progresses or as a result of treatment. In this regard, references to mesothelioma includes mesothelioma with resistance towards topoisomerase poisons, alkylating agents, antitubulines, antifolates, platinum compounds and radiation therapy, in particular cisplatin-resistant mesothelioma. Similarly references to multiple myeloma includes bortezomib-sensitive multiple myeloma or refractory multiple myeloma and references to chronic myelogenous leukemia includes imitanib-sensitive chronic myelogenous leukemia and refractory chronic myelogenous leukemia.

The cancers may be cancers which are sensitive to antagonism of any one or more IAP selected from XIAP, cIAP1, cIAP2, NAIP, ILP2, ML-IAP, survivin and BRUCE, more preferably XIAP, cIAP1, cIAP2, ML-IAP, most preferably XIAP.

It is further envisaged that the compounds of the invention, and in particular those compounds having IAP affinity will be particularly useful in the treatment or prevention of cancers of a type associated with or characterised by the presence of elevated levels of IAP or amplification of 11q22 for example the cancers referred to in this context in the introductory section of this application.

Elevated levels of IAP due to overexpression of IAP is found in many cancers and is associated with a poor prognosis. In addition, cancers with the 11q22 amplification may also be sensitive to an IAP antagonist. The elevated levels of IAP and amplification of 11q22 can be identified by the techniques outlined herein. Whether a particular cancer is one which is sensitive to IAP function, may be determined by a method as set out in the section headed "Methods of Diagnosis".

A further aspect provides the use of a compound for the manufacture of a medicament for the treatment of a disease or condition as described herein, in particular cancer.

The compounds may also be useful in the treatment of tumour growth, pathogenesis, resistance to chemo- and radiotherapy by sensitising cells to chemotherapy and as an antimetastatic agent.

Therapeutic anticancer interventions of all types necessarily increase the stresses imposed on the target tumour cells. In mitigating the deleterious effects of such stresses, IAPs are directly implicated in resisting the effects of cancer drugs and treatment regimens. Thus, antagonists of IAP represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

As a consequence of their affinity for IAP, the compounds will be useful in providing a means of controlling programmed cell death. Therefore, it is also envisaged that the compounds of the invention may be useful in treating other conditions such as inflammatory disorders such as hepatitis, ulcerative colitis, and gastritis; neurodegenerative conditions such as Alzheimers' disease, Parkinson's disease, Huntington's disease, myotonic dystrophy, and amyotrophic lateral sclerosis; AIDS, ischemia such as restenosis, traumatic brain injury, spinal cord injury, cerebral ischemia, cerebral ischemia/reperfusion (I/R) injury, acute and chronic CNS injury ischemia, stroke or myocardial infarction; degenerative diseases of the musculoskeletal system such as osteoporosis; autoimmune diseases such as multiple sclerosis (MS) and Type I diabetes, and eye diseases such as retinal degeneration.

The affinity of the compounds of the invention as antagonists of IAP can be measured using the biological and biophysical assays set forth in the examples herein and the level of affinity exhibited by a given compound can be defined in terms of the $IC_{50}$ value. Preferred compounds of the present invention are compounds having an $IC_{50}$ value of less than 1 µM, more preferably less than 0.1 µM.

In one embodiment the invention provides a compound for use in the treatment of a disease or condition which is mediated by IAP (e.g. XIAP and/or cIAP e.g. cIAP1). In a further embodiment the invention provides a compound for use in the treatment of a disease or condition which overexpresses IAP (e.g. XIAP and/or cIAP e.g. cIAP1).

In one embodiment the invention provides a compound for use in the treatment of a disease or condition which is mediated by IAP, wherein the compound is an antagonist of IAP having an $IC_{50}$ of less than 50 µM in at least one assay (e.g. a displacement binding) against an IAP. In particular the IAP is XIAP, cIAP1 and/or cIAP2. In a further embodiment the disease or condition which is mediated by IAP is a cancer which is characterised by overexpression of at least one IAP and/or amplication of 11q22.

In one embodiment the invention provides a compound for use in the treatment of a disease or condition which is mediated by IAP, wherein the compound has an $IC_{50}$ of less than 10 µM against at least one IAP in an assay (e.g. displacement binding) against IAP.

A further aspect provides the use of a compound for the manufacture of a medicament for the treatment of a disease or condition which is mediated by IAP, wherein the compound is an antagonist of IAP having an $IC_{50}$ of less than 50 µM against at least one IAP in an assay (e.g. a displacement binding).

Methods of Diagnosis

Prior to administration of a compound of the formula (I), a patient may be screened to determine whether a disease or condition from which the patient is or may be suffering is one which would be susceptible to treatment with a compound having affinity for IAP. The term 'patient' includes human and veterinary subjects.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of IAP or to sensitisation of a pathway to normal IAP function or to upregulation of a biochemical pathway downstream of IAP activation.

Examples of such abnormalities that result in activation or sensitisation of the IAP, loss of, or inhibition of apoptotic pathways, up-regulation of the receptors or ligands, cytogenetic aberrations or presence of mutant variants of the receptors or ligands. Tumours with up-regulation of IAP, in particular over-expression of IAP, may be particularly sensitive to IAP antagonists. For example, overexpression of XIAP and cIAP has been identified in a range of cancers as discussion in the Background section.

Amplification of chromosome 11q22 has been detected in cell lines and primary tumours from squamous cell carcinomas of the esophagus (Imoto et al., 2001) and cervix (Imoto et al., 2002) as well as in primary lung cancers/cell lines (Dai et al., 2003). Immunohistochemistry and western blot analysis have identified cIAP1 and cIAP2 as potential oncogenes in this region as both are overexpressed in cancers in which this rare amplification arises.

The term up-regulation includes elevated expression or over-expression, including gene amplification (i.e. multiple gene copies), cytogenetic aberration and increased expression by a transcriptional effect. Thus, the patient may be subjected to a diagnostic test to detect a marker characteristic of up-regulation of IAP. The term diagnosis includes screening. By marker we include genetic markers including, for example, the measurement of DNA composition to identify presence of mutations of IAP or 11q22 amplification. The term marker also includes markers which are characteristic of up regulation of IAP, including protein levels, protein state and mRNA levels of the aforementioned proteins.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal spears, skin biopsy or urine.

Methods of identification and analysis of cytogenetic aberration, genetic amplification, mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of IAP, detection of IAP variants or mutants, or detection of 11q22 amplification could be applicable in the present case.

Abnormal levels of proteins such as IAP can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured.

Alternative methods for the measurement of the over expression or elevation of IAPs including the isoforms thereof, include the measurement of microvessel density. This can for example be measured using methods described by Orre and Rogers (Int J Cancer (1999), 84(2), 101-8). Assay methods also include the use of markers.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having affinity for IAP (i.e. an IAP antagonist).

Another aspect of the invention includes a compound of the invention for use in the prophylaxis or treatment of cancer in a patient selected from a sub-population possessing overexpression of one or more of the IAP family members (e.g. cIAP and/or XIAP).

Another aspect of the invention includes a compound of the invention for use in the prophylaxis or treatment of cancer in a patient selected as possessing a cytogenetic abherration that results in overexpression of IAPs, for example, a patient selected as possessing the 11q22 amplification.

MRI determination of vessel normalization (e.g. using MRI gradient echo, spin echo, and contrast enhancement to measure blood volume, relative vessel size, and vascular permeability) in combination with circulating biomarkers may also be used to identify for treatment with a compound of the invention.

Thus a further aspect of the invention is a method for the diagnosis and treatment of a disease state or condition mediated by a IAP, which method comprises (i) screening a patient to determine whether a disease or condition from which the patient is or may be suffering is one which would be susceptible to treatment with a compound having affinity for IAP; and (ii) where it is indicated that the disease or condition from which the patient is thus susceptible, thereafter administering to the patient a compound of formula (I) and sub-groups or examples thereof as defined herein.

Pharmaceutical Formulations

While it is possible for the active compound to be administered alone, it is preferable to present it as a pharmaceutical composition (e.g. formulation).

Thus, the present invention further provides pharmaceutical compositions, as defined above, and methods of making a pharmaceutical composition comprising (e.g. admixing) at least one compound of formula (I) (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and pre-filled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer. Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g. solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads (non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by IAP. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It has been discovered that IAP antagonists can be used as a single agent or in combination with other anticancer agents. For example, it may be beneficial to combine an antagonist that induces apoptosis with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents.

Particular examples of anti-cancer agents or adjuvants (or salts thereof), include but are not limited to any of the agents selected from groups (i)-(xlvi), and optionally group (xlvii), below:
(i) Platinum compounds, for example cisplatin (optionally combined with amifostine), carboplatin or oxaliplatin;
(ii) Taxane compounds, for example paclitaxel, paclitaxel protein bound particles (Abraxane™), docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);
(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);
(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;
(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;
(xi) DNA methyl transferase inhibitors, for example temozolomide, azacytidine or decitabine;
(xii) Antifolates, for example methotrexate, pemetrexed disodium, or raltitrexed;
(xiii) Cytotoxic antibiotics, for example antinomycin D, bleomycin, mitomycin C, dactinomycin, caminomycin, daunomycin, levamisole, plicamycin, or mithramycin;
(xiv) Tubulin-binding agents, for example combrestatin, colchicines or nocodazole;
(xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), or vemurafenib (PLX4032/RG7204);
(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;
(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;
(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);
(xix) Hsp90 inhibitors for example AT13387, herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;

(xx) Monoclonal Antibodies (uncongjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), ipilimumab (CTLA4), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R3064651JNJ-16241199, JNJ-26481585, trichostatin A, vorinostat, chlamydocin, A-173, JNJ-MGCD-0103, PXD-101, or apicidin;

(xxxii) Proteasome Inhibitors for example bortezomib, carfilzomib, CEP-18770, MLN-9708, or ONX-0912;

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab;

(xxxvi) Telomerase inhibitors for example telomestain;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAIL/Apo2 Ligand;

(xlvii) Prophylactic agents (adjuncts); i.e. agents that reduce or alleviate some of the side effects associated with chemotherapy agents, for example anti-emetic agents, agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim), agents that inhibit bone resorption such as denosumab or bisphosphonates e.g. zoledronate, zoledronic acid, pamidronate and ibandronate, agents that suppress inflammatory responses such as dexamethasone, prednisone, and prednisolone, agents used to reduce blood levels of growth hormone and IGF-I (and other hormones) in patients with acromegaly or other rare hormone-producing tumours, such as synthetic forms of the hormone somatostatin e.g. octreotide acetate, antidote to drugs that decrease levels of folic acid such as leucovorin, or folinic acid, agents for pain e.g. opiates such as morphine, diamorphine and fentanyl, non-steroidal anti-inflammatory drugs (NSAID) such as COX-2 inhibitors for example celecoxib, etoricoxib and lumiracoxib, agents for mucositis e.g. palifermin, agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (I) is administered in combination therapy with one, two, three, four or more other therapeutic agents (preferably one or two, more preferably one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

In one embodiment is provided a combination of a compound of formula (I) with one or more (e.g. 1 or 2) other therapeutic agents (e.g. anticancer agents as described above).

In another embodiment is provided a compound of formula (I) in combination with one or more (e.g. 1 or 2) other therapeutic agents (e.g. anticancer agents) for use in therapy, such as in the prophylaxis or treatment of cancer.

In one embodiment the pharmaceutical composition comprises a compound of formula (I) together with a pharmaceutically acceptable carrier and optionally one or more therapeutic agent(s).

In another embodiment the invention relates to the use of a combination according to the invention in the manufacture of a pharmaceutical composition for inhibiting the growth of tumour cells.

In a further embodiment the invention relates to a product containing a compound of formula (1) and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples. Compounds are named using an automated naming package such as AutoNom (MDL) or are as named by the chemical supplier. In the examples, the following abbreviations are used.

ABBREVIATIONS

BINAP, 2,2'-bis(diphenylphosphino)-1,1'-binaphthalene; Boc$_2$O, di-tert-butyl dicarbonate; CDI, 1,1'-carbonyldiimidazole; DCE, 1,2-dichloroethane; DCM, Dichloromethane; DMSO, dimethylsulfoxide; DMF, N,N-dimethylformamide; DMAP, -(dimethylamino)pyridine; EtOAc, ethyl acetate; EtOH, ethanol; HATU, N,N,N',N'-tetramethyl-O-(7-azabenzotriazol-1-yl)uronium hexafluorophosphate; HCl, Hydrochloric acid; HPLC, High pressure liquid chromatography; LiHMDS, lithium bis(trimethylsilyl)amide; mins., Minutes; MeCN, acetonitrile; MS, Mass Spectrometry; NMR, Nuclear Magnetic Resonance Spectroscopy; PyBOP, benzotriazol-1-yloxy)tris(dimethylamino)phosphonium hexafluorophosphate; Pd$_2$(dba)$_3$, tris(dibenzylidineacetone)palladium (0); Petrol, petroleum ether fraction with boiling point range 40-60° C. Sat., Saturated; TFA, trifluoroacetic acid; THF, Tetrahydrofuran.

NMR Data

Unless indicated, $^1$H NMR spectra were recorded at 25° C. on a Bruker Avance I spectrometer operating at 400 MHz. The data were processed and analysed using Topspin 2.1 software. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

Analytical and Preparative LC-MS Systems

Analytical LC-MS System and Method Description

In the following examples, compounds were characterised by mass spectroscopy using the systems and operating conditions set out below. Where atoms with different isotopes are present and a single mass quoted, the mass quoted for the compound is the monoisotopic mass (i.e. $^{35}$Cl; $^{79}$Br etc.).

Waters Platform LC-MS System:
HPLC System: Waters 2795
Mass Spec Detector: Micromass Platform LC
PDA Detector: Waters 2996 PDA Platform MS Conditions:
Capillary voltage: 3.6 kV (3.40 kV on ES negative)
Cone voltage: 30 V
Source Temperature: 120° C.

Scan Range: 125-800 amu
Ionisation Mode: ElectroSpray Positive or
  ElectroSpray Negative or
  ElectroSpray Positive & Negative
Waters Fractionlynx LC-MS System:
HPLC System: 2767 autosampler—2525 binary gradient pump
Mass Spec Detector: Waters ZQ
PDA Detector: Waters 2996 PDA
  Fractionlynx MS conditions:
Capillary voltage: 3.5 kV (3.25 kV on ES negative)
Cone voltage: 40 V (25 V on ES negative)
Source Temperature: 120° C.
Scan Range: 125-800 amu
Ionisation Mode: ElectroSpray Positive or
  ElectroSpray Negative or
  ElectroSpray Positive & Negative
Agilent 1200SL-6140 LC-MS System—RAPID:
HPLC System: Agilent 1200 series SL
Mass Spec Detector: Agilent 6140 single quadrupole
Second Detector Agilent 1200 MWD SL
  Agilent MS Conditions:
Capillary voltage: 4000V on ES pos (3500V on ES Neg)
Fragmentor/Gain: 100
Gain: 1
Drying gas flow: 7.0 L/min
Gas Temperature: 345° C.
Nebuliser Pressure: 35 psig
Scan Range: 125-800 amu
Ionisation Mode ElectroSpray Positive-Negative switching
Preparative LC-MS System and Method Description Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.
Waters Fractionlynx system:
  Hardware:
  2767 Dual Loop Autosampler/Fraction Collector
  2525 preparative pump
  CFO (column fluidic organiser) for column selection
  RMA (Waters reagent manager) as make up pump
  Waters ZQ Mass Spectrometer
  Waters 2996 Photo Diode Array detector
  Waters ZQ Mass Spectrometer
  Waters MS Running Conditions:
  Capillary voltage: 3.5 kV (3.2 kV on ES Negative)
  Cone voltage: 25 V
  Source Temperature: 120° C.
  Scan Range: 125-800 amu
  Ionisation Mode: ElectroSpray Positive or
    ElectroSpray Negative
Agilent 1100 LC-MS Preparative System:
  Hardware:
  Autosampler: 1100 series "prepALS"
  Pump: 1100 series "PrepPump" for preparative flow gradient and 1100 series "QuatPump" for pumping modifier in prep flow
  UV detector: 1100 series "MWD" Multi Wavelength Detector
  MS detector: 1100 series "LC-MSD VL"
  Fraction Collector: 2×"Prep-FC"
  Make Up pump: "Waters RMA"
  Agilent Active Splitter
  Agilent MS Running Conditions:
  Capillary voltage: 4000 V (3500 V on ES Negative)
  Fragmentor/Gain: 150/1
  Drying gas flow: 12.0 L/min
  Gas Temperature: 350° C.
  Nebuliser Pressure: 50 psig
  Scan Range: 125-800 amu
  Ionisation Mode ElectroSpray Positive or
    ElectroSpray Negative
Columns:
A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge™ Prep OBD™ C18 and Phenyl, Atlantis® Prep T3 OBD™ and Sunfire™ Prep OBD C18 5 μm 19×100 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.
Eluents:
Mobile phase eluent was chosen in conjunction with column manufacturers recommended stationary phase limitations in order to optimise a columns separation performance.
Methods:
Achiral Preparative Chromatography
The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.
Chiral Preparative Chromatography
Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Synthetic Methods

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

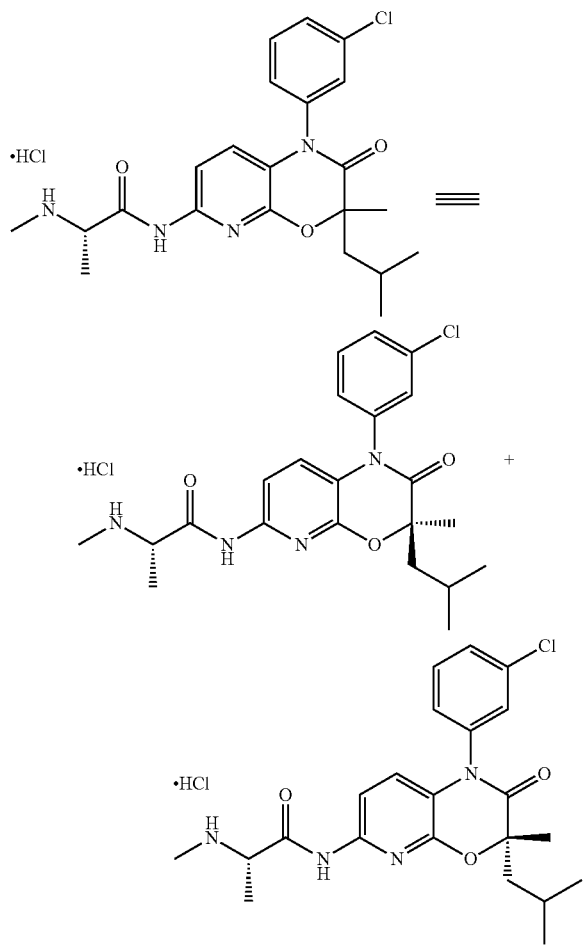

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

General Procedure 1 (TFA Deprotection)

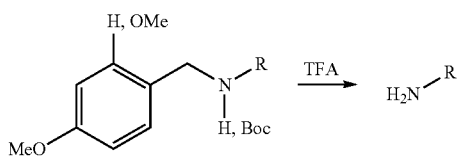

The substrate was treated with TFA (30-40 vol) and the mixture stirred at ambient temperature for 1 hour in case of 2,4-dimethoxybenzyl derivatives. In the case of 4-methoxybenzyl derivatives, the mixture was stirred for either 24-48 hours at ambient temperature or 3-4 hours at 70° C. The TFA was evaporated in vacuo and the residue was used as the TFA salt. In some cases the residue was partitioned between EtOAc or dichloromethane and saturated sodium hydrogen carbonate solution. The organic phase was washed with brine, dried over MgSO$_4$, filtered and concentrated in vacuo and occasionally the residue was purified using SiO$_2$ chromatography (EtOAc/Petrol) to give the product.

General Procedure 2 (HATU Coupling)

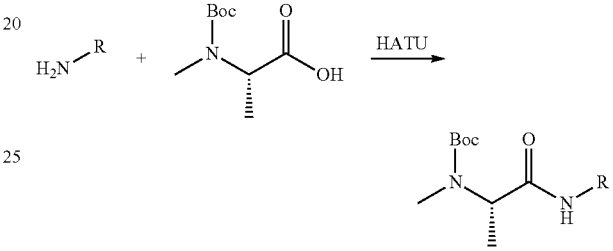

The amine (free base or TFA salt) was dissolved in DMF (30 vol) and treated successively with N,N-diisopropylethylamine (4.5 mol. eq), Boc-N-methyl-L-alanine (3 mol. eq.) and HATU (3 mol. eq). The mixture was stirred at ambient temperature for between 24-36 hours and then concentrated in vacuo. The residue was partitioned between EtOAc and dilute aqueous sodium carbonate solution. The EtOAc layer was then washed with dilute aqueous potassium hydrogenphosphate solution (optional), brine, dried over MgSO$_4$, filtered and concentrated in vacuo. In some cases the residue was then dissolved in toluene, filtered to remove insoluble impurities, and then evaporated to dryness. The filtrate was concentrated in vacuo and the residue purified using SiO$_2$ chromatography (EtOAc/Petrol) to give the product.

General Procedure 3 (HCl Deprotection)

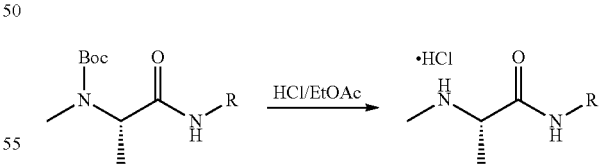

The substrate was treated with HCl (saturated solution in EtOAc, 30-40 vol) and the mixture stirred at ambient temperature for 1 hour. In some cases, the product crystallised from solution and was collected by filtration. In other cases, the mixture was evaporated to dryness and the residue purified by trituration or recrystallisation (using combinations of Et$_2$O, EtOAc, MeOH). Alternatively, the residue was purified by preparative LCMS.

General Procedure 4 (PyBOP Coupling)

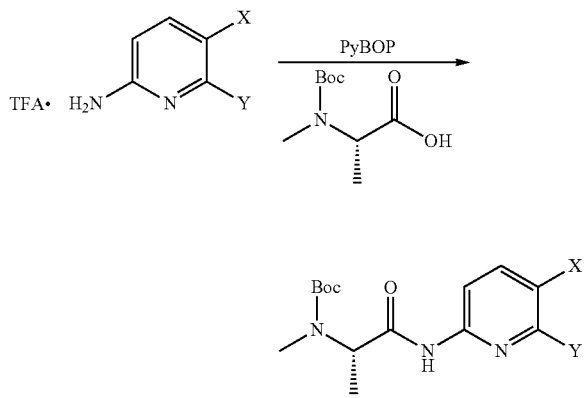

The starting material was dissolved in dichloromethane (30 vol) and treated successively with N,N-diisopropylethylamine (4.5 mol. eq), Boc-N-methyl-L-alanine (1.5 mol. eq.) and PyBOP (1.5 mol. eq). The mixture was stirred at ambient temperature for between 24-48 hours. The reaction mixture was diluted with dichloromethane, washed with saturated sodium hydrogen carbonate, brine, dried over MgSO$_4$, filtered and concentrated in vacuo and the residue purified using SiO$_2$ chromatography (EtOAc/Petrol) to give the product.

Intermediate A1

((S)-1-Carbamoyl-ethyl)-methyl-carbamic acid tert-butyl ester

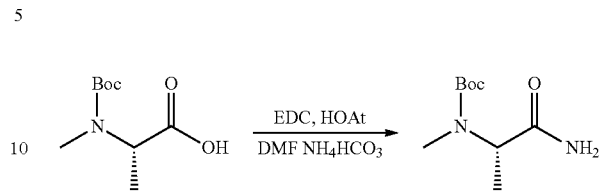

Boc-N-methyl-L-alanine (3.12 g, 15.3 mmol), EDC (2.94 g, 15.3 mmol), HOAt (2.09 g, 15.3 mmol) and ammonium hydrogencarbonate (3.63 g, 45.9 mmol) were added to DMF (20 mL) and stirred at ambient temperature overnight. The mixture was partitioned between EtOAc and water. The EtOAc layer was washed with aqueous potassium hydrogen sulfate solution (×2), dilute aqueous sodium carbonate solution and brine. The EtOAc was evaporated to give the title compound as a white solid (1 g). 1H NMR (400 MHz, DMSO-d6): 7.19 (1H, br), 6.95 (1H, br), 4.60-4.20 (1H, m), 2.73 (3H, s), 1.39 (9H, s), 1.24 (3H, d).

Example 1

N-[3-(4-Chloro-benzyl)-2-oxo-2,3-dihydro-1H-imidazo[4,5-b]pyridin-5-yl]-2-methylamino-propionamide hydrochloride (prepared as a mixture of enantiomers)

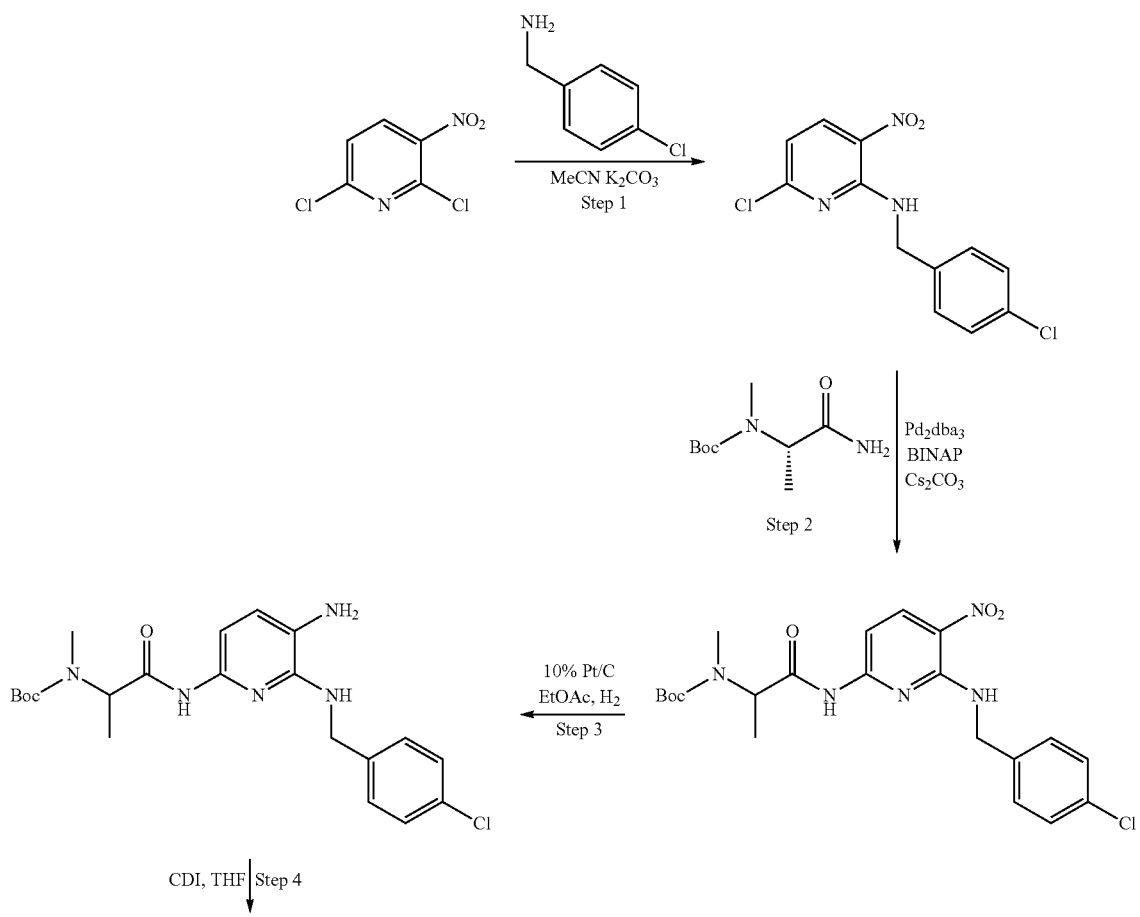

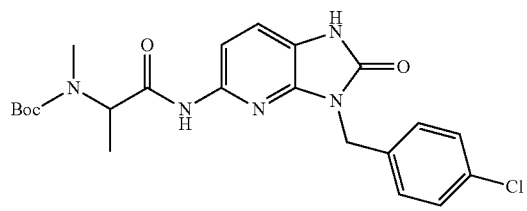 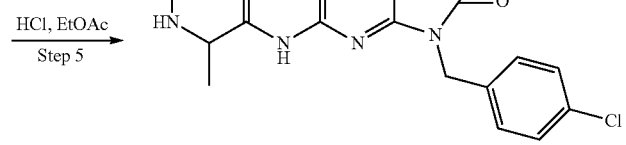

Step 1:

4-Chlorobenzylamine (7.3 mL, 60 mmol) was added dropwise to a stirred, cooled (~0° C.), solution of 2,6-dichloro-3-nitropyridine (10.1 g, 52.2 mmol) and K₂CO₃ (7.93 g, 57.4 mmol) in MeCN (60 mL). After stirring for 5 hours at ambient temperature, the mixture was concentrated in vacuo and then partitioned between EtOAc and water. The EtOAc layer was then washed successively with aqueous potassium hydrogen sulfate solution, brine and then dried (MgSO₄). The solution was evaporated in vacuo to give a yellow solid which was recrystallised from heptane/EtOAc (1:2) to give (4-chloro-benzyl)-(6-chloro-3-nitro-pyridin-2-yl)-amine as a yellow solid (7.67 g). The mother liquor was evaporated and the residue recrystallised from EtOH to give a second crop of product (3.39 g). MS: [M+H]⁺=298

Step 2:

(4-Chloro-benzyl)-(6-chloro-3-nitro-pyridin-2-yl)-amine (685 mg, 2.31 mmol), ((S)-1-carbamoyl-ethyl)-methyl-carbamic acid tert-butyl ester (Intermediate A1) (606 mg, 3.0 mmol), Pd₂dba₃ (210 mg, 0.23 mmol), BINAP (286 mg, 0.46 mmol) and Cs₂CO₃ (1.5 g, 4.62 mmol) were added to 1,4-dioxane (15 mL). The mixture was evacuated and flushed with N₂ three times and then heated at 90° C. for 2 hours. The mixture was cooled, diluted with EtOAc, filtered and concentrated in vacuo. The residue was purified by SiO₂ chromatography (10-30% EtOAc/Petrol) to give {1-[6-(4-chloro-benzylamino)-5-nitro-pyridin-2-ylcarbamoyl]-ethyl}-methyl-carbamic acid tert-butyl ester (611 mg) as an orange foamy solid. MS: [M+H]⁺=464.

Step 3:

EtOAc (15 mL) was added to {1-[6-(4-chloro-benzylamino)-5-nitro-pyridin-2-ylcarbamoyl]-ethyl}-methyl-carbamic acid tert-butyl ester (300 mg, 0.65 mmol) and 10% Pt/C (80 mg). The mixture was stirred under an atmosphere of hydrogen for 2 hours. The mixture was filtered and the filtrate was concentrated in vacuo to give {1-[5-amino-6-(4-chlorobenzylamino)-pyridin-2-ylcarbamoyl]-ethyl}-methyl-carbamic acid tert-butyl ester which was used immediately in the next step.

Step 4:

A solution of the product from Step 3, in THF (3 mL), was added to a solution of N,N'-carbonyldiimidazole (110 mg, 0.68 mmol) in THF (3 mL). The mixture was then heated at 70° C. for 3 hours. After allowing to cool, the mixture was concentrated in vacuo, treated with water and then left overnight. The product was extracted with EtOAc. The EtOAc layer was washed successively with aqueous potassium hydrogensulfate solution, brine and then dried (MgSO₄). The solution was concentrated to ~1 mL and then Et₂O (3 mL) was added. The resulting precipitate was collected by filtration to give {1-[3-(4-chloro-benzyl)-2-oxo-2,3-dihydro-1H-imidazo[4,5-b]pyridin-5-ylcarbamoyl]ethyl}-methyl-carbamic acid tert-butyl ester (90 mg) as a white crystalline solid. MS: [M+H]⁺=460.

Step 5:

The product from Step 4 was dissolved in THF (2 mL) and then added to a solution of saturated HCl in EtOAc. After 2 hours, the resulting precipitate was collected by filtration and washed with EtOAc to give the title compound as a white solid (30 mg). 1H NMR (400 MHz, DMSO-d6): 11.31-11.23 (1H, m), 10.87 (1H, s), 9.37 (1H, br), 8.99 (1H, br), 7.78 (1H, d), 7.47-7.35 (3H, m), 7.31 (2H, d), 5.00 (2H, s), 4.08-3.95 (1H, m), 2.57-2.53 (3H, m), 1.47 (3H, d). MS: [M+H]⁺ 360.

Example 2

(S)—N-[1-(4-Chloro-phenyl)-2-oxo-2,3-dihydro-1H-pyrido[2,3-b][1,4]oxazin-6-yl]-2-methylamino-propionamide hydrochloride

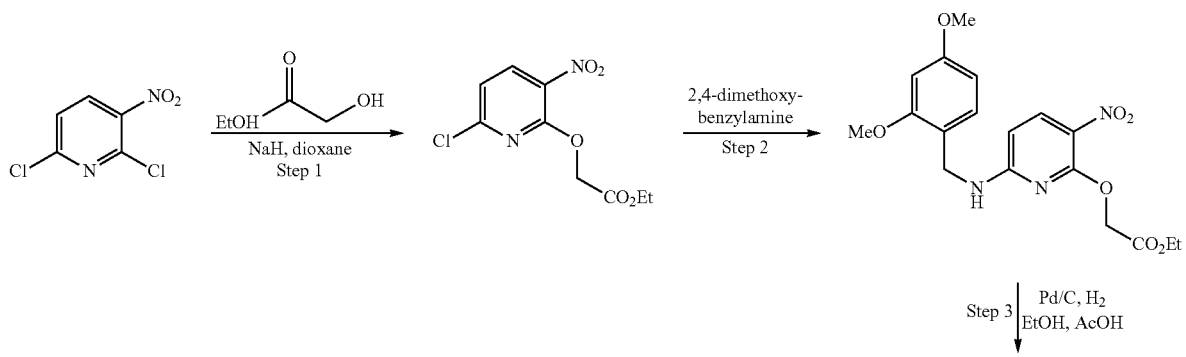

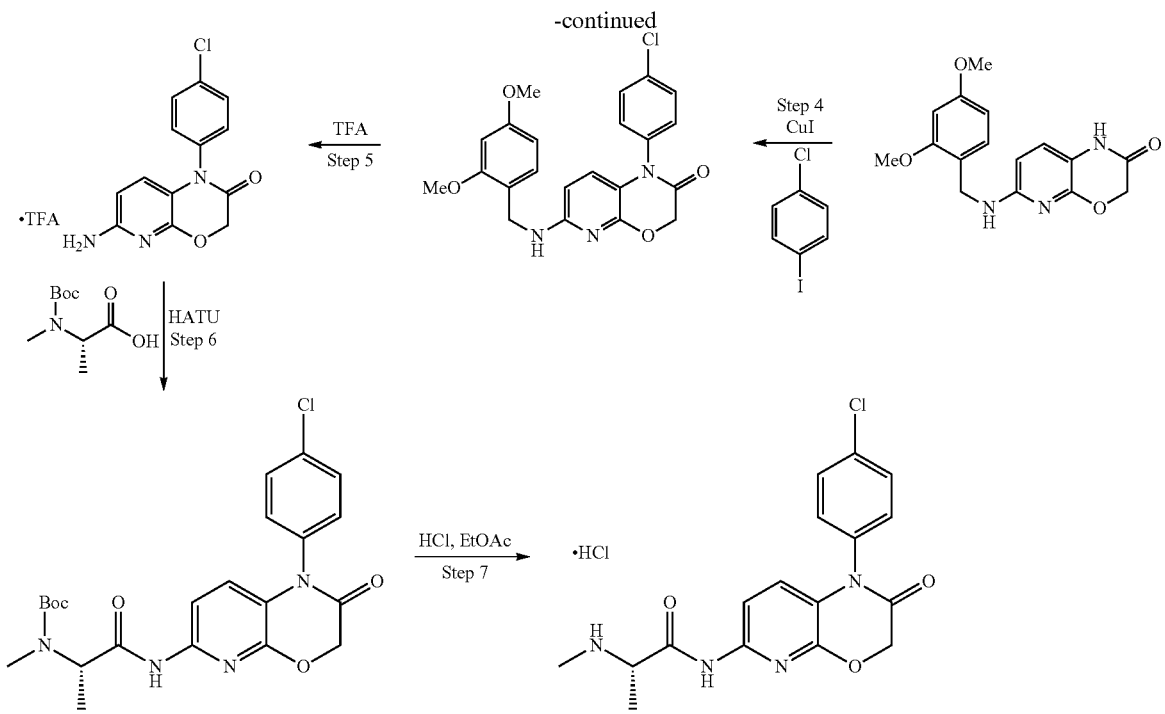

Step 1:

A stirred solution of 2,6-dichloro-3-nitropyridine (15 g, 78 mmol) and ethyl glycolate (8.1 mL, 86 mmol) in 1,4-dioxane (150 mL) was cooled to 10° C. NaH (60% dispersion in oil) (3.42 g, 86 mmol) was added batchwise. The mixture was then allowed to stir for 6 hours at ambient temperature. The mixture was then cooled (~10° C.) and treated with saturated aqueous ammonium chloride solution. Water was added until all the solid had dissolved and the mixture was extracted with EtOAc. The EtOAc layer was washed with brine, dried over MgSO$_4$, filtered and concentrated in vacuo. The residue was purified by crystallisation from EtOH (80 mL) to give (6-chloro-3-nitro-pyridin-2-yloxy)-acetic acid ethyl ester (8.55 g). [M+H]$^+$ 261

Step 2:

To a cooled (~10° C.) solution of (6-chloro-3-nitro-pyridin-2-yloxy)-acetic acid ethyl ester (8.0 g, 30.8 mmol) in MeCN (80 mL) was added a solution of triethylamine (6.4 mL, 46 mmol) and 2,4-dimethoxybenzylamine (5.5 mL, 37 mmol). The mixture was then stirred for 16 hours at ambient temperature and then concentrated in vacuo. The residue was partitioned between EtOAc and aqueous potassium hydrogenphosphate solution. The EtOAc layer was then washed with brine, dried over MgSO$_4$, filtered and concentrated in vacuo. The residue was purified using SiO$_2$ chromatography (10-50% EtOAc/Petrol) to give [6-(2,4-dimethoxy-benzylamino)-3-nitro-pyridin-2-yloxy]acetic acid ethyl ester (9.53 g) as a yellow solid. MS: [M+H]$^+$ 392

Step 3:

[6-(2,4-Dimethoxy-benzylamino)-3-nitro-pyridin-2-yloxy]acetic acid ethyl ester (6.35 g, 16.2 mmol) and acetic acid (8 mL) were dissolved EtOH (160 mL). 10% Pd/C (635 mg) was added and the mixture was stirred under a hydrogen atmosphere for 24 hours after which time the product precipitated. The solid was collected by filtration, suspended in 1,4-dioxane (200 mL) and then heated briefly to ~100° C. The mixture was allowed to cool and was then filtered while still luke-warm (to remove Pd/C). The filtrate was evaporated in vacuo to give 6-(2,4-dimethoxy-benzylamino)-1H-pyrido[2,3-b][1,4]oxazin-2-one (3.76 g) as a beige solid. MS: [M+H]$^+$=316.

Step 4:

6-(2,4-Dimethoxy-benzylamino)-1H-pyrido[2,3-b][1,4]oxazin-2-one (3.76 g, 11.9 mmol), 4-iodo-chlorobenzene (3.4 g, 14.3 mmol), N,N'-dimethylethylenediamine (1.27 mL, 11.9 mmol), and CsF (4.5 g, 29.7 mmol) were suspended in MeCN (100 mL) and sparged with nitrogen. CuI (238 mg, 1.19 mmol) was then added and the mixture stirred at 80° C. for 16 hours. The mixture was allowed to cool and was then concentrated in vacuo. The residue was partitioned between EtOAc and aqueous potassium hydrogenphosphate solution. The EtOAc layer was then washed with saturated aqueous ammonium chloride solution, brine, dried over MgSO$_4$, filtered and then concentrated in vacuo. The residue was purified using SiO$_2$ chromatography (20-70% EtOAc/Petrol) to give 1-(4-chloro-phenyl)-6-(2,4-dimethoxybenzylamino)-1H-pyrido[2,3-b][1,4]oxazin-2-one (4.42 g) as a pale yellow crystalline solid. MS: [M+H]$^+$=426.

Step 5 and 6:

Step 5 was performed in a fashion similar to General procedure 1 (TFA deprotection). A portion of the product (100 mg) was then used in Step 6 by following the method described in General procedure 2 (HATU coupling) to give {(S)-1-[1-(4-chloro-phenyl)-2-oxo-2,3-dihydro-1H-pyrido[2,3-b][1,4]oxazin-6-ylcarbamoyl]ethyl}-methyl-carbamic acid tert-butyl ester (23 mg). MS: [M+H]$^+$=461.

Step 7:

{(S)-1-[1-(4-Chloro-phenyl)-2-oxo-2,3-dihydro-1H-pyrido[2,3-b][1,4]oxazin-6-ylcarbamoyl]-ethyl}-methyl-carbamic acid tert-butyl ester (23 mg) was treated with HCl, according to General procedure 3 (HCl deprotection), to give the title compound (8 mg). 1H NMR (400 MHz, DMSO-d6): 11.10 (1H, s), 9.20 (1H, br), 8.94 (1H, br), 7.71-7.59 (3H, m), 7.47-7.38 (2H, m), 6.86 (1H, d), 5.03 (2H, s), 4.01-3.92 (1H, m), 2.58-2.53 (3H, m), 1.47 (3H, d). MS: [M+H]$^+$ 361.

Example 3

(S)—N—[(S)-1-(4-Chloro-phenyl)-3-methyl-2-oxo-3-phenyl-2,3-dihydro-1H-pyrido[2,3-b][1,4]oxazin-6-yl]-2-methylamino-propionamide hydrochloride 1H NMR (DMSO-d6) 1H NMR 11.17 (1H, br), 9.01 (2H, br), 7.67 (2H, d), 7.58 (1H, d), 7.53-7.30 (7H, m), 6.80 (1H, d), 3.98-3.92 (1H, m), 2.54 (3H, s), 1.90 (3H, s), 1.46 (3H, d). [M+H]$^+$ 451.

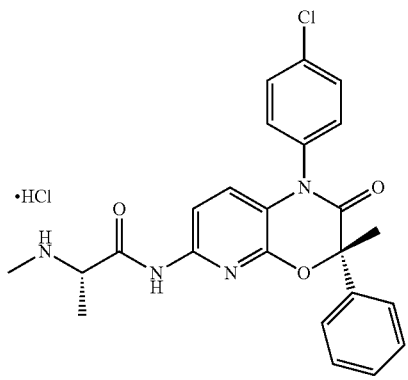 [SMILES: CN[C@@H](C)C(=O)Nc1ccc2c(n1)O[C@@](C)(c1ccccc1)C(=O)N2c1ccc(Cl)cc1 ; Cl]

Starting with (S)-(+)-2-hydroxy-2-phenylpropionic acid methyl ester and 2,6-dichloro-3-nitropyridine, the title compound was prepared by using similar methods to those described for Example 2 (Steps 1-7) with the exception of Step 3, which was performed using Fe/AcOH rather than Pd/C-hydrogen; as follows.

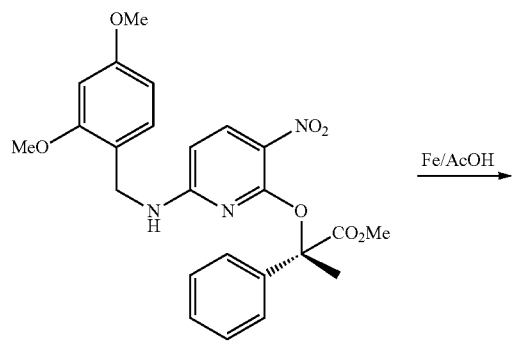

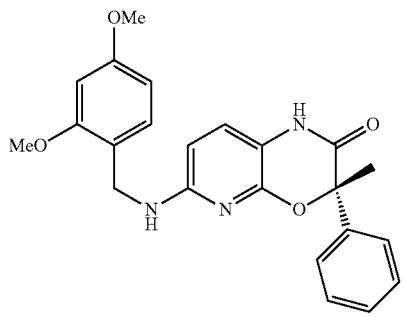

To (S)-2-[6-(2,4-dimethoxy-benzylamino)-3-nitro-pyridin-2-yloxy]-2-phenyl-propionic acid methyl ester (253 mg, 0.54 mmol) in AcOH (7 mL) was added Fe-powder (242 mg, 4.32 mmol). The mixture was heated at 60° C. for 3 hours and then allowed to cool. The mixture was evaporated in vacuo and then the residue was purified using SiO$_2$ chromatography (1-1.5% MeOH/CH$_2$Cl$_2$) to give (S)-6-(2,4-dimethoxy-benzylamino)-3-methyl-3-phenyl-1H-pyrido[2,3-b][1,4]oxazin-2-one (167 mg) as a beige solid. MS: [M+H]$^+$=406.

Example 4

(S)—N—((S)-3-Benzyl-2-oxo-2,3-dihydro-1H-pyrido[2,3-b][1,4]oxazin-6-yl)-2-methylamino-propionamide hydrochloride (prepared as a mixture of 2 diastereoisomers)

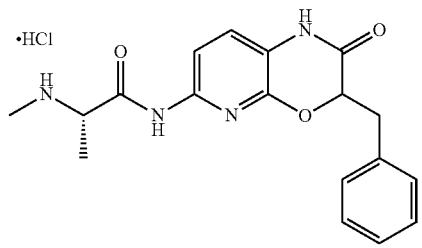 [SMILES: CN[C@@H](C)C(=O)Nc1ccc2c(n1)OC(Cc1ccccc1)C(=O)N2 ; Cl]

Starting with (S)-2-hydroxy-3-phenyl-propionic acid and 2,6-dichloro-3-nitropyridine, the title compound was prepared by using similar methods to those described for Example 2 (Steps 1-7). 1H NMR (400 MHz, DMSO-d6): 11.03 (1H, s), 10.89 (1H, s), 9.17 (1H, br), 8.92 (1H, br), 7.67 (1H, d), 7.34-7.19 (6H, m), 5.12 (1H, dd), 3.96-3.87 (1H, m), 3.26 (1H, dd), 3.09 (1H, dd), 2.54 (3H, t), 1.46 (3H, d). MS: [M+H]$^+$=341.

Example 5

(S)—N-[1-(4-Chloro-phenyl)-3,3-diethyl-2-oxo-2,3-dihydro-1H-pyrido[2,3-b][1,4]oxazin-6-yl]-2-methylamino-propionamide hydrochloride

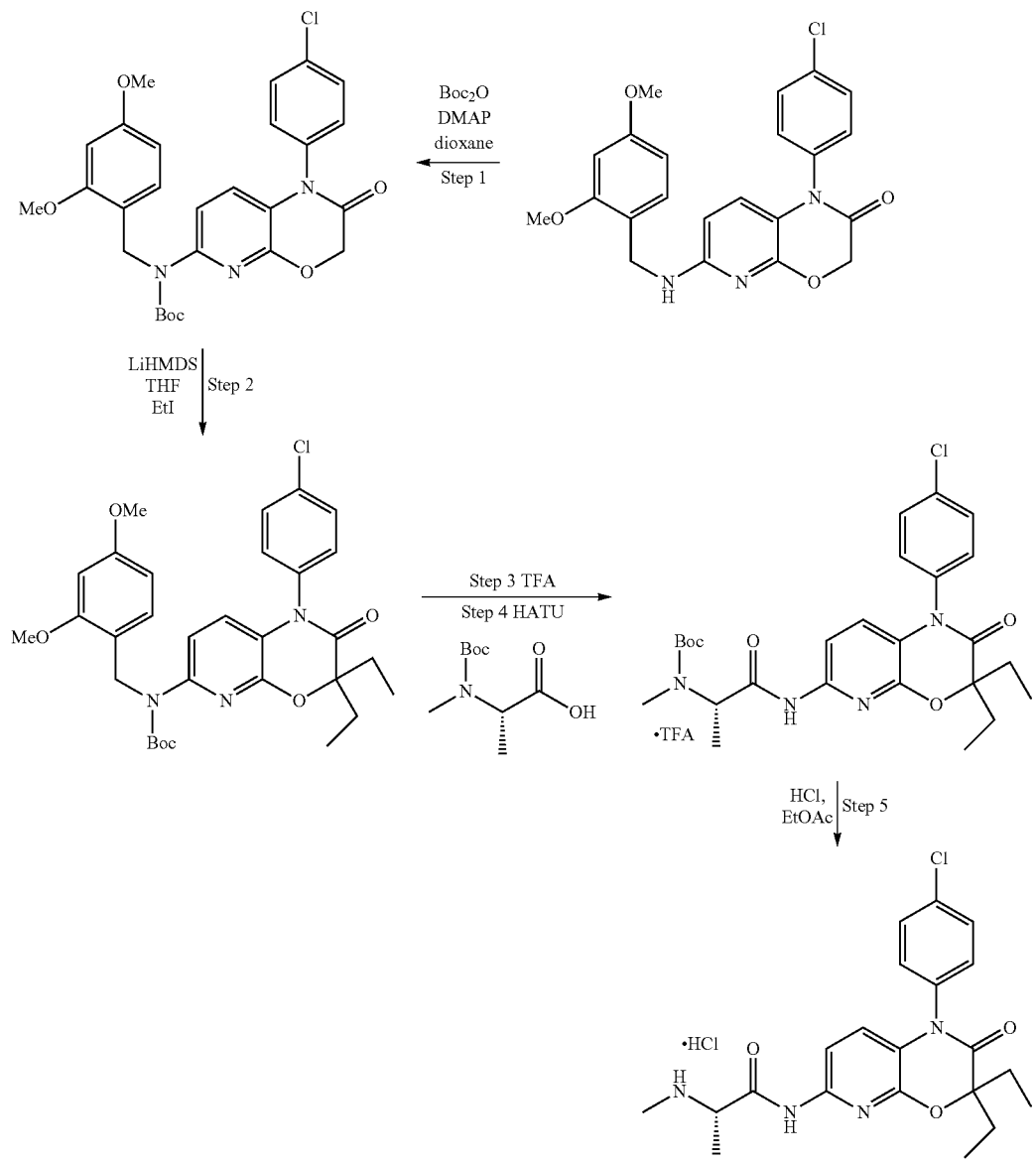

Step 1:

1-(4-Chloro-phenyl)-6-(2,4-dimethoxybenzylamino)-1H-pyrido[2,3-b][1,4]oxazin-2-one (from Example 2, Step 4) (4.42 g, 10.4 mmol), di-tert-butyl dicarbonate (4.53 g, 20.8 mmol) and DMAP (250 mg, 2.1 mmol) were dissolved in 1,4-dioxane and heated at 100° C. for 6 hours. A further 1.5 g of di-tert-butyl dicarbonate was added and heating continued for a further 2 hours. After allowing to cool to ambient temperature, water (30 mL) was added and the mixture stirred for a further 3 hours. The mixture was concentrated in vacuo and then partitioned between EtOAc and dilute aqueous potassium hydrogen phosphate solution. The EtOAc layer was then washed with brine, dried over MgSO$_4$ and concentrated in vacuo. The residue was purified using SiO$_2$ chromatography (20-40% EtOAc/Petrol) to give [1-(4-chloro-phenyl)-2-oxo-2,3-dihydro-1H-pyrido[2,3-b][1,4]oxazin-6-yl]-(2,4-dimethoxy-benzyl)-carbamic acid tert-butyl ester (4.88 g) as a white crystalline solid. MS: [M+H]$^+$526.

Step 2:

[1-(4-Chloro-phenyl)-2-oxo-2,3-dihydro-1H-pyrido[2,3-b][1,4]oxazin-6-yl]-(2,4-dimethoxy-benzyl)-carbamic acid tert-butyl ester (370 mg, 0.66 mmol) was dissolved in THF (8 mL) and cooled to –78° C. LiHMDS (1 M solution in THF, 2 mL, 1.98 mmol) was added and the mixture stirred at −78° C. for 15 minutes. Iodoethane (160 mL, 1.98 mmol) was then added to the mixture, the cooling bath removed and then stirring continued for a further 15 minutes, during which time, the mixture reached ambient temperature. Saturated aqueous ammonium chloride and EtOAc were added. The EtOAc layer was isolated and washed with dilute aqueous potassium hydrogen phosphate solution. The EtOAc layer was then washed with brine, dried over MgSO$_4$, filtered and concentrated in vacuo. The residue was purified using SiO$_2$ chromatography (10-30% EtOAc/Petrol) to give [1-(4-chloro-phenyl)-3,3-diethyl-2-oxo-2,3-dihydro-1H-pyrido[2,3-b][1,4]oxazin-6-yl]-(2,4-dimethoxy-benzyl)-carbamic acid tert-butyl ester (145 mg). MS: [M+H]$^+$ 582.

Step 3-5:

By following similar methods to those described in General procedures 1-3, [1-(4-chloro-phenyl)-3,3-diethyl-2-oxo-2,3-dihydro-1H-pyrido[2,3-b][1,4]oxazin-6-yl]-(2,4-dimethoxy-benzyl)-carbamic acid tert-butyl ester (145 mg) was used to give the title compound (41 mg). 1H NMR (400 MHz, Me-d3-OD): 7.76-7.58 (3H, m), 7.31 (2H, d), 6.79 (1H, d), 4.05-3.97 (1H, m), 2.74 (3H, s), 2.19-2.04 (2H, m), 2.04-1.86 (2H, m), 1.61 (3H, d), 1.06 (6H, t). MS: [M+H]$^+$ 417.

The compounds in the Table below, were prepared by following methods similar to those described for Example 5 (Steps 1-5) above. All MS Data is [M+H]$^+$

| Eg. | Compound and Name | N.M.R. Data | M.S | Procedure |
|---|---|---|---|---|
| 6 | 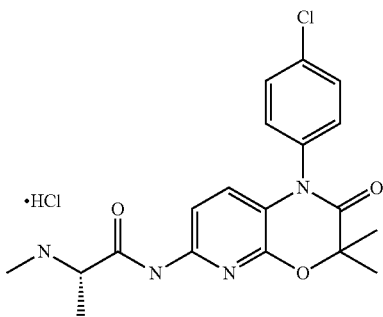<br>(S)-N-[1-(4-Chloro-phenyl)-3,3-dimethyl-2-oxo-2,3-dihydro-1H-pyrido[2,3-b][1,4]oxazin-6-yl]-2-methylamino-propionamide hydrochloride | 1H NMR (400 MHz, Me-d3-OD): 7.74 (1H, d), 7.69-7.57 (2H, m), 7.40-7.28 (2H, m), 6.86 (1H, d), 4.08-3.95 (1H, m), 2.74 (3H, s), 1.65 (6H, s), 1.62 (3H, d). | 389 | Using iodomethane in Step 2 |
| 7 | 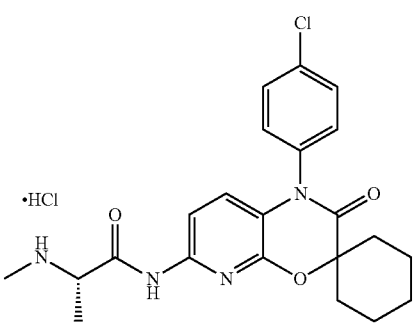 [SMILES: CN[C@@H](C)C(=O)Nc1ccc2c(n1)OC1(CCCCC1)C(=O)N2c1ccc(Cl)cc1 ; Cl]<br>(2S)-N-[4'-(4-Chlorophenyl)-3'-oxo-3',4'-dihydrospiro[cyclohexane-1,2'-pyrido[2,3-b][1,4]oxazine]-7'-yl]-2-(methylamino)propanamide hydrochloride | 1H NMR (DMSO-d6) 11.25 (1H, s), 9.38-8.91 (2H, m), 7.74-7.59 (3H, m), 7.39 (2H, d), 6.86 (1H, d), 3.98-3.92 (1H, m), 2.55 (3H, s), 2.00-1.82 (4H, m), 1.66 (5H, s), 1.48 (3H, d), 1.40-1.28 (1H, m). | 429 | Using 1,5-diiodopentane in Step 2 |

| Eg. | Compound and Name | N.M.R. Data | M.S | Procedure |
|---|---|---|---|---|
| 8 | 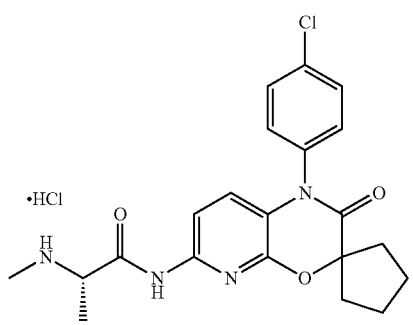 [SMILES: CN[C@@H](C)C(=O)Nc1ccc2c(n1)OC1(CCCC1)C(=O)N2c1ccc(Cl)cc1 ; Cl]<br><br>(2S)-N-[4'-(4-Chlorophenyl)-3'-oxo-3',4'-dihydrospiro[cyclopentane-1,2'-pyrido[2,3-b][1,4]oxazine]-7'-yl]-2-(methylamino)propanamide hydrochloride | 1H NMR (400 MHz, DMSO-d6): 11.15 (1H, s), 9.59-8.92 (2H, m), 7.72-7.60 (3H, m), 7.48-7.38 (2H, m), 6.88 (1H, d), 3.95 (1H, q), 2.53 (3H, s), 2.33-2.16 (2H, m), 2.07-1.93 (2H, m), 1.93-1.72 (4H, m), 1.48 (3H, d). | 415 | Using 1,4-diiodobutane in Step 2 |
| 9 | 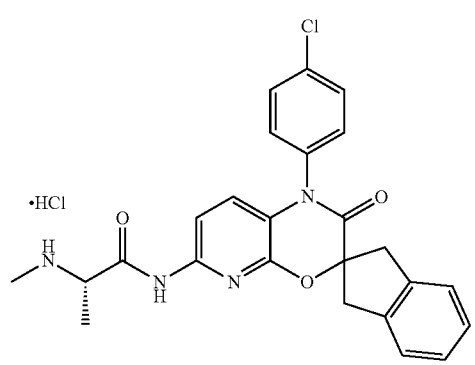 [SMILES: CN[C@@H](C)C(=O)Nc1ccc2c(n1)OC1(Cc3ccccc3C1)C(=O)N2c1ccc(Cl)cc1 ; Cl]<br><br>(2S)-N-[4'-(4-Chlorophenyl)-3'-oxo-1,3,3',4'-tetrahydrospiro[indene-2,2'-pyrido[2,3-b][1,4]oxazine]-7'-yl]-2-(methylamino)propanamide hydrochloride | 1H NMR (400 MHz, DMSO-d6): 11.04 (1H, s), 9.33-8.97 (2H, m), 7.74-7.60 (3H, m), 7.56-7.43 (2H, m), 7.35-7.17 (4H, m), 6.96 (1H, d), 3.98-3.86 (1H, m), 3.74 (2H, dd), 3.36-3.29 (2H, m), 2.53 (3H, s), 1.45 (3H, d). | 463 | Using 1,2-bis-bromomethyl-benzene in Step 2 |

Intermediate A2

1-(3-Chloro-phenyl)-6-(2,4-dimethoxy-benzylamino)-3-methyl-1H-pyrido[2,3-b][1,4]oxazin-2-one (prepared as a mixture of 2 enantiomers)

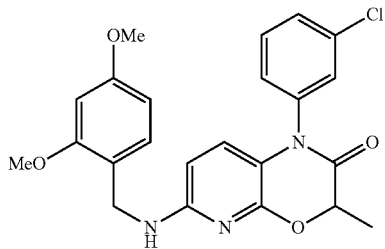 [SMILES: COc1ccc(CNc2ccc3c(n2)OC(C)C(=O)N3c2cccc(Cl)c2)c(OC)c1]

The title compound was prepared by using similar methods to those described for Example 2 (Steps 1-4) with the exception of Step 1, which was performed with (R)-2-hydroxy-propionic acid methyl ester instead of ethyl glycolate and Step 4 which was performed using 1-chloro-3-iodo-benzene instead of 4-iodo-chlorobenzene. 1H NMR (400 MHz, DMSO-d6): 7.61-7.53 (2H, m), 7.47 (1H, d), 7.33-7.24 (1H, m), 7.11 (1H, d), 6.76 (1H, t), 6.59-6.53 (2H, m), 6.46 (1H, dd), 6.13 (1H, d), 4.91 (1H, q), 4.27 (2H, d), 3.80 (3H, s), 3.74 (3H, s), 1.51 (3H, d). MS: [M+H]$^+$=440.

Example 10

(S)—N-[1-(3-Chloro-phenyl)-3,3-dimethyl-2-oxo-2,3-dihydro-1H-pyrido[2,3-b][1,4]oxazin-6-yl]-2-methylamino-propionamide hydrochloride Step 1:

1-(3-Chloro-phenyl)-6-(2,4-dimethoxy-benzylamino)-3-methyl-1H-pyrido[2,3-b][1,4]oxazin-2-one (Intermediate A2) (4.2 g, 9.6 mmol) was treated with di-tert-butyl dicarbonate (4.2 g, 19.1 mmol) and DMAP (232 mg, 1.9 mmol) following similar methods to those described in Example 5 (Step 1) to give [1-(3-chloro-phenyl)-3-methyl-2-oxo-2,3-dihydro-1H-pyrido[2,3-b][1,4]oxazin-6-yl]-(2,4-dimethoxy-benzyl)-carbamic acid tert-butyl ester as a pale yellow solid (4.2 g). 1H NMR (400 MHz, DMSO-d6): 7.68-7.53 (3H, m), 7.53-7.29 (1H, m), 7.17 (1H, d), 6.94 (1H, d), 6.76 (1H, d), 6.52 (1H, d), 6.45 (1H, dd), 5.09 (1H, q), 4.88 (2H, s), 3.73 (3H, s), 3.71 (3H, s), 1.55 (3H, d), 1.35 (9H, s).

Step 2:

Starting from [1-(3-chloro-phenyl)-3-methyl-2-oxo-2,3-dihydro-1H-pyrido[2,3-b][1,4]oxazin-6-yl]-(2,4-dimethoxy-benzyl)-carbamic acid tert-butyl ester (200 mg, 0.37 mmol), LiHMDS (1 M solution in THF, 440 μL, 0.44 mmol) and iodomethane (35 μL, 0.55 mmol), [1-(3-chloro-phenyl)-3,3-dimethyl-2-oxo-2,3-dihydro-1H-pyrido[2,3-b][1,4]oxazin-6-yl]-(2,4-di methoxy-benzyl)-carbamic acid tert-butyl ester (160 mg) was prepared by using similar methods to those described for Example 5 (Step 2). MS: [M+H]$^+$ 554.

Step 3-5:

Were performed by following methods similar to those described for General procedures 1-3 respectively, giving the title compound as a yellow solid (44 mg). 1H NMR (400 MHz, DMSO-d6): 11.08 (1H, s), 9.46 (1H, bs), 9.02 (1H, bs), 7.72-7.51 (4H, m), 7.42-7.32 (1H, m), 6.86 (1H, d), 4.04-3.91 (1H, m), 3.64-3.35 (3H, m), 1.57 (6H, s), 1.51-1.45 (3H, m). MS: [M+H]$^+$=389.

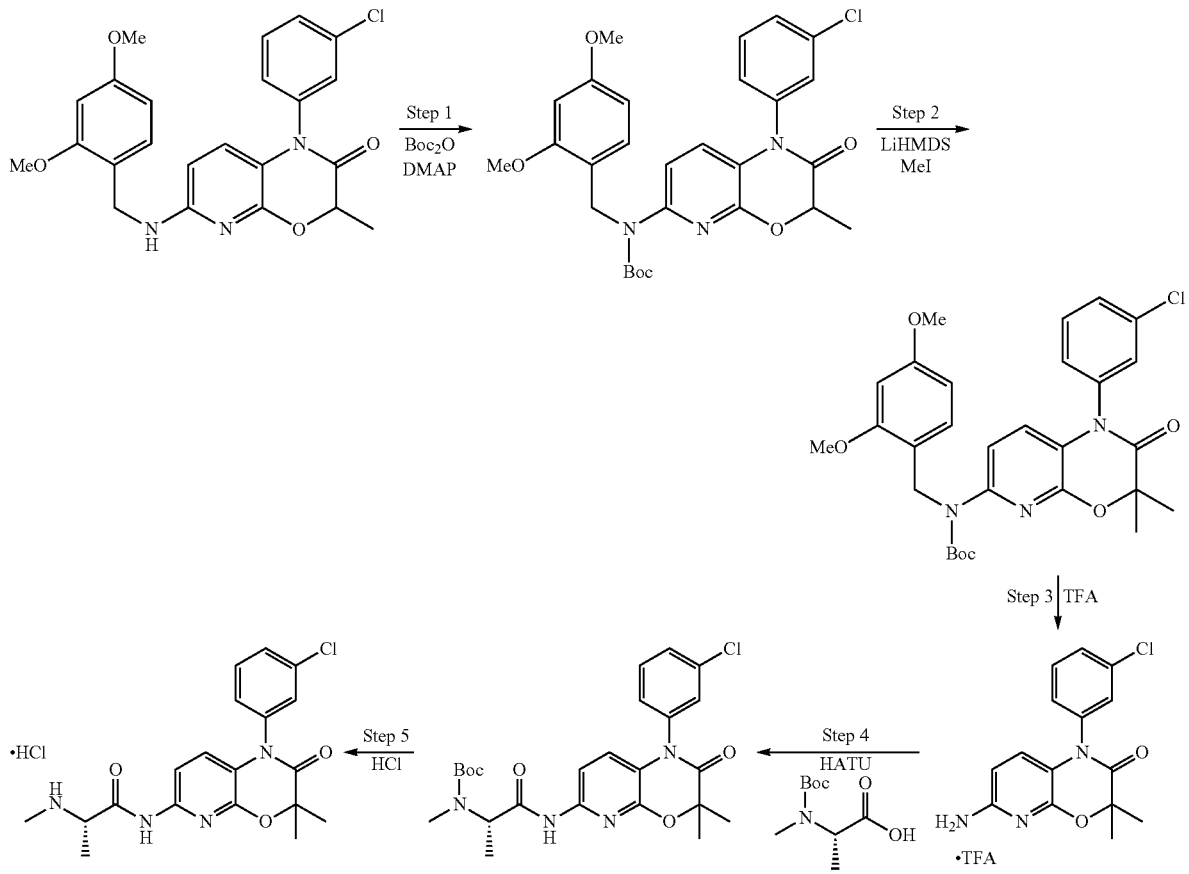

The Examples in the Table below, were prepared by following methods similar to those described for Example 10 (Steps 1-5) above (the examples were prepared as mixtures of 2 diastereoisomers). All MS Data is [M+H]+

| Eg. | Compound and name | N.M.R. data | M.S. | Procedure |
|---|---|---|---|---|
| 11 | 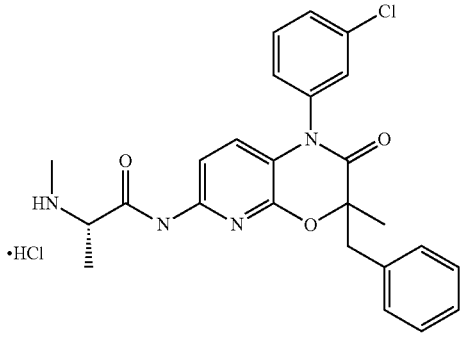 [SMILES: Cl ; CN[C@@H](C)C(=O)Nc1ccc2c(n1)OC(C)(Cc1ccccc1)C(=O)N2c1cccc(Cl)c1]<br>(S)-N-[3-Benzyl-1-(3-chloro-phenyl)-3-methyl-2-oxo-2,3-dihydro-1H-pyrido[2,3-b][1,4]oxazin-6-yl]-2-methylamino-propionamide hydrochloride | 1H NMR (400 MHz, DMSO-d6): 11.14 (1H, bs), 9.30 (1H, bs), 8.97 (1H, bs), 7.66-7.54 (3H, m), 7.46 (1H, s), 7.34-7.21 (6H, m), 6.71 (1H, dd), 3.97 (1H, s), 3.43-3.25 (5H, m), 1.55 (3H, s), 1.52-1.32 (3H, m) | 465 | Using benzyl bromide in Step 2 |
| 12 | 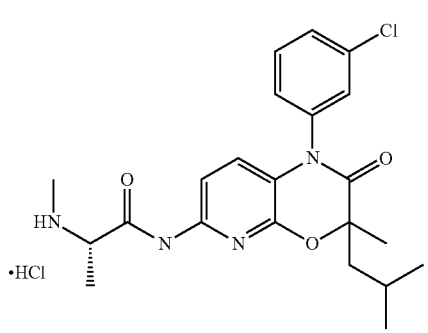<br>(S)-N-[1-(3-Chloro-phenyl)-3-isobutyl-3-methyl-2-oxo-2,3-dihydro-1H-pyrido[2,3-b][1,4]oxazin-6-yl]-2-methylamino-propionamide hydrochloride | 1H NMR (400 MHz, DMSO-d6): 11.11 (1H, s), 9.34 (1H, bs), 8.99 (1H, bs), 7.70-7.59 (3H, m), 7.55 (1H, s), 7.39-7.30 (1H, m), 6.83 (1H, d), 3.97 (1H, s), 3.34 (3H, s), 2.01-1.88 (2H, m), 1.82-1.70 (1H, m), 1.57 (3H, s), 1.54-1.41 (3H, m), 1.39-1.29 (1H, m), 1.26-1.04 (2H, m), 1.01-0.83 (3H, m) | 431 | Using 1-iodo-2-methyl-propane in Step 2 |
| 13 | 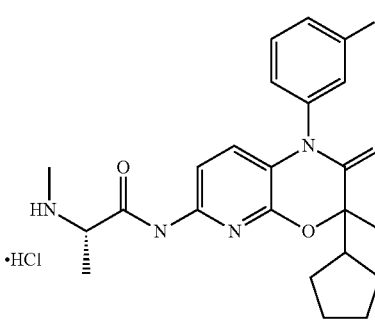<br>(S)-N-[1-(3-Chloro-phenyl)-3-cyclopentyl-3-methyl-2-oxo-2,3-dihydro-1H-pyrido[2,3-b][1,4]oxazin-6-yl]-2-methylamino-propionamide hydrochloride | 1H NMR (400 MHz, DMSO-d6): 11.16 (1H, s), 9.49 (1H, bs), 9.03 (1H, bs), 7.68-7.59 (3H, m), 7.56 (1H, s), 7.40-7.31 (1H, m), 6.80 (1H, d), 4.01-3.89 (1H, m), 3.48-3.29 (3H, m), 1.82-1.73 (1H, m), 1.73-1.62 (2H, m), 1.55 (9H, d), 1.48 (3H, d) | 443 | Using iodocyclopentane in Step 2 |

101

Intermediate A3

[1-(3-Chloro-phenyl)-3-methyl-3-(3-methyl-but-2-enyl)-2-oxo-2,3-dihydro-1H-pyrido[2,3-b][1,4]oxazin-6-yl]-(2,4-dimethoxy-benzyl)-carbamic acid tert-butyl ester (prepared as a mixture of 2 enantiomers)

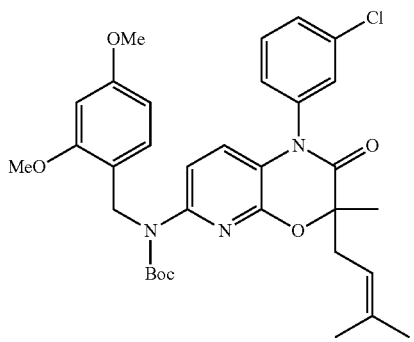 [SMILES: COc1ccc(CN(C(=O)OC(C)(C)C)c2ccc3c(n2)OC(C)(CC=C(C)C)C(=O)N3c2cccc(Cl)c2)c(OC)c1]

The title compound was prepared by using similar methods to those described for Example 10 (Steps 1-2) with the exception of Step 2, which was performed using 1-bromo-3-methyl-but-2-ene instead of iodomethane. MS: [M+N$^+$]=608.

Example 14

(S)-2-Methylamino-N-[3-methyl-3-(3-methyl-butyl)-2-oxo-1-phenyl-2,3-dihydro-1H-pyrido[2,3-b][1,4]oxazin-6-yl]-propionamide hydrochloride (prepared as a mixture of 2 diastereoisomers)

102

Step 1:

[1-(3-Chloro-phenyl)-3-methyl-3-(3-methyl-but-2-enyl)-2-oxo-2,3-dihydro-1H-pyrido[2,3-b][1,4]oxazin-6-yl]-(2,4-dimethoxy-benzyl)-carbamic acid tert-butyl ester (Intermediate A3) (360 mg, 0.59 mmol) was dissolved in MeOH (20 mL) and stirred at ambient temperature for 16 hours in the presence of Pd/C (10%, 63 mg) under H$_2$. The resulting suspension was filtered through Celite and the solvent was removed in vacuo to give (2,4-dimethoxy-benzyl)-[3-methyl-3-(3-methyl-butyl)-2-oxo-1-phenyl-2,3-dihydro-1H-pyrido[2,3-b][1,4]oxazin-6-yl]-carbamic acid tert-butyl ester as a pale yellow solid (120 mg). MS: [M+H]$^+$=576.

Step 2-4:

Were performed by following methods similar to those described for General procedures 1-3 respectively, to give the title compound as a pale yellow solid (22 mg). 1H NMR (400 MHz, DMSO-d6): 11.09 (1H, s), 9.35 (1H, s), 8.98 (1H, s), 7.68-7.49 (4H, m), 7.34 (2H, d), 6.75 (1H, d), 3.97 (1H, s), 3.56 (3H, d), 2.02-1.88 (1H, m), 1.87-1.74 (1H, m), 1.60-1.43 (7H, m), 1.43-1.25 (2H, m), 0.91-0.80 (6H, m). MS: [M+H]$^+$=411.

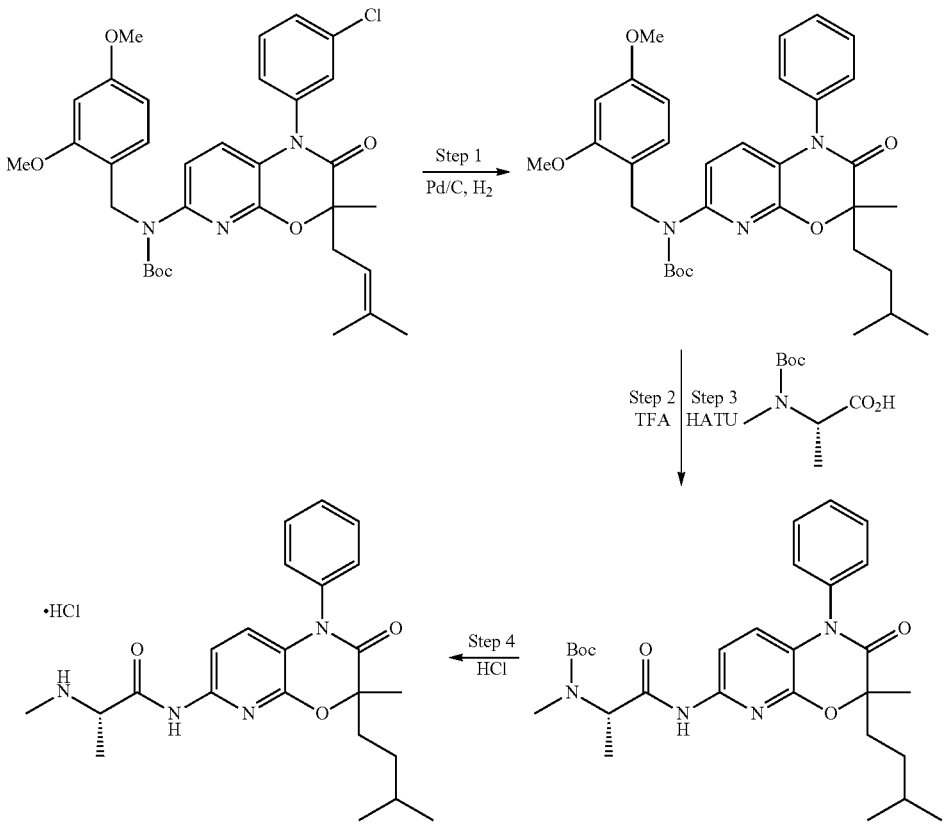

Example 15

(S)-2-Methylamino-N—((S)-3-methyl-2-oxo-1,2,3,4-tetrahydro-pyrido[2,3-b]pyrazin-6-yl)-propionamide hydrochloride

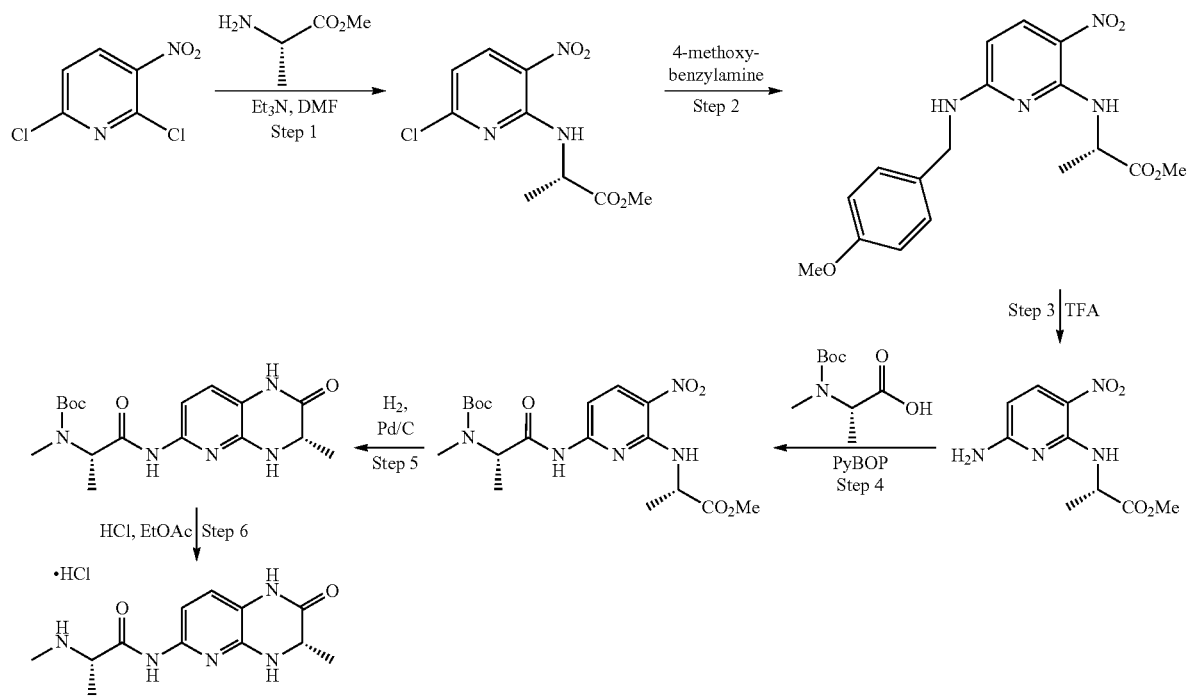

Step 1:

To a solution of L-alanine-methyl ester hydrochloride (1.68 g, 12.0 mmol, 1.1 equiv) and triethylamine (3.32 mL, 24.0 mmol 2.2 equiv) in DMF (20 mL) was added a solution of 2,6-dichloro-2-nitro-pyridine (2.14 g, 11.0 mmol, 1.0 equiv) in DMF (6 mL) and the reaction mixture was stirred at ambient temperature for 3 h. The reaction mixture was poured onto water and the product was extracted with EtOAc. The organic phase was washed with brine, dried (MgSO$_4$), filtered and concentrated under reduced pressure. The crude product was purified by column chromatography (SiO$_2$, eluted with petrol—EtOAc 0-30%) to afford (S)-2-(6-chloro-3-nitro-pyridin-2-ylamino)-propionic acid methyl ester (1.9 g). MS: [M+H]$^+$=260.

Step 2:

To a solution of (S)-2-(6-chloro-3-nitro-pyridin-2-ylamino)-propionic acid methyl ester (1.90 g, 7.3 mmol, 1.0 equiv) in EtOH (20 mL) was added 4-methoxy-benzylamine (1.4 mL, 11.0 mmol, 1.5 equiv) and the reaction mixture was stirred at ambient temperature for 16 h. The solvent was evaporated and the crude product was triturated with methanol to afford (S)-2-[6-(4-methoxy-benzylamino)-3-nitro-pyridin-2-ylamino]-propionic acid methyl ester (1.5 g) as a yellow solid. MS: [M+H]$^+$=361.

Step 3:

(S)-2-[6-(4-Methoxy-benzylamino)-3-nitro-pyridin-2-ylamino]-propionic acid methyl ester (300 mg, 0.83 mmol) was treated with TFA according to the General procedure 1 (TFA deprotection) to afford, after purification, (S)-2-(6-amino-3-nitro-pyridin-2-ylamino)-propionic acid methyl ester (125 mg). MS: [M+H]$^+$=241.

Step 4:

(S)-2-(6-Amino-3-nitro-pyridin-2-ylamino)-propionic acid methyl ester (121 mg, 0.5 mmol) was reacted according to the General procedure 4 (PyBop coupling) to afford 90 mg of (S)-2-{6-[(S)-2-(tert-butoxycarbonyl-methyl-amino)-propionylamino]-3-nitro-pyridin-2-ylamino}-propionic acid methyl ester. MS: [M+H]$^+$=426.

Step 5:

To a solution of (S)-2-{6-[(S)-2-(tert-butoxycarbonyl-methyl-amino)-propionylamino]-3-nitro-pyridin-2-ylamino}-propionic acid methyl ester (90 mg, 0.21 mmol) in THF (3 mL) and acetic acid (3 mL) and MeOH (3 mL) was added Pd/C (10%, 90 mg) and the reaction mixture was hydrogenated for 3 h. The catalyst was filtered and the filtrate evaporated. The residue was partitioned between saturated NaHCO$_3$ and EtOAc. The organic phase was dried (MgSO$_4$), filtered and evaporated. The crude material was purified by preparative HPLC to afford methyl-[(S)-1-((S)-3-methyl-2-oxo-1,2,3,4-tetrahydro-pyrido[2,3-b]pyrazin-6-ylcarbamoyl)-ethyl]-carbamic acid tert-butyl ester (33 mg). MS: [M+H]$^+$=364.

Step 6:

Methyl-[(S)-1-((S)-3-methyl-2-oxo-1,2,3,4-tetrahydro-pyrido[2,3-b]pyrazin-6-ylcarbamoyl)-ethyl]-carbamic acid tert-butyl ester (30 mg, 0.08 mmol) was treated with HCl according to the General procedure 3 (HCl deprotection) to afford the title compound (15 mg). 1H NMR (400 MHz, Me-d3-OD): 7.25 (1H, d), 6.91 (1H, d), 4.43-4.32 (1H, m), 4.12 (1H, d), 2.79 (3H, s), 1.67 (3H, d), 1.53 (3H, d). MS: [M+H]$^+$=264.

Example 16

(S)-2-Methylamino-N-(2-oxo-1,2,3,4-tetrahydro-pyrido[2,3-b]pyrazin-6-yl)-propionamide hydrochloride

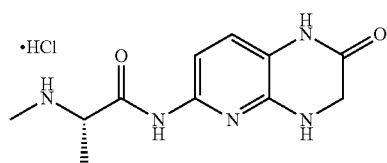 [SMILES: CN[C@@H](C)C(=O)Nc1ccc2c(n1)NCC(=O)N2 ; Cl]

The title compound was prepared by using methods similar to those described in Example 15, except that glycine ethyl ester hydrochloride was used in Step 1 instead of L-alanine methyl ester hydrochloride. 1H NMR (400 MHz, Me-d3-OD): 7.25 (1H, d), 6.83 (1H, d), 4.25 (2H, s), 4.19-4.06 (1H, m), 2.84-2.73 (3H, m), 1.73-1.58 (3H, m). MS: [M+H]$^+$=250.

Example 17

(S)—N-(1,3-Dimethyl-2-oxo-2,3-dihydro-1H-imidazo[4,5-b]pyridin-5-yl)-2-methylamino-propionamide hydrochloride

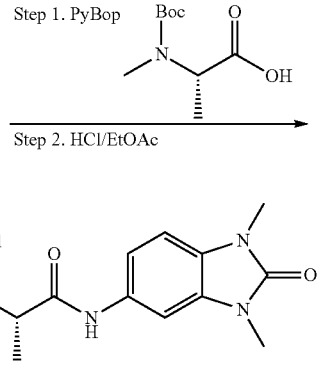

5-Amino-1,3-dimethyl-1,3-dihydro-imidazo[4,5-b]pyridin-2-one (Russian Journal of Organic Chemistry, 2007, 43, 11, 1706-1709) was treated with Boc-N-methyl-L-alanine according to the General procedure 4 (PyBop coupling) and the product of the reaction deprotected according to the General procedure 3 (HCl deprotection) to afford the title compound. 1H NMR (400 MHz, Me-d3-OD): 7.93 (1H, d), 7.48 (1H, d), 4.04 (1H, d), 3.45 (6H, s), 2.77 (3H, s), 1.64 (3H, d). MS: [M+H]$^+$=264.

Example 18

(S)—N-(3-Benzyl-2-oxo-1-phenyl-1,2,3,4-tetrahydro-pyrido[3,2-d]pyrimidin-6-yl)-2-methylamino-propionamide hydrochloride

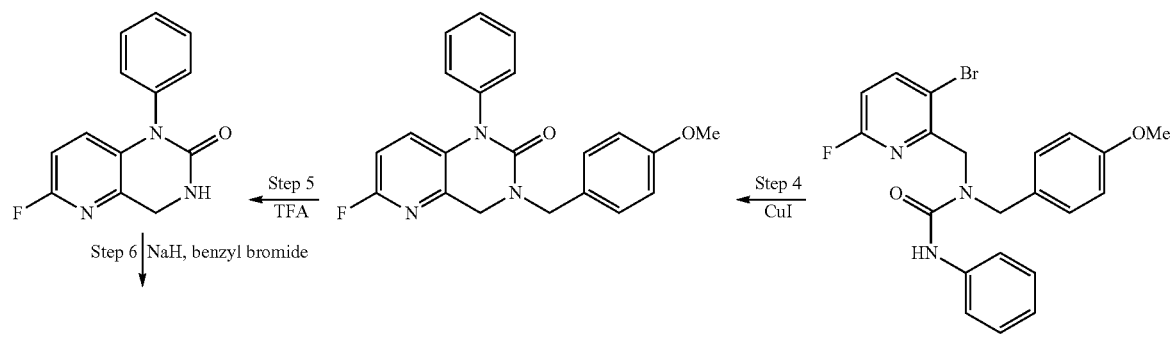

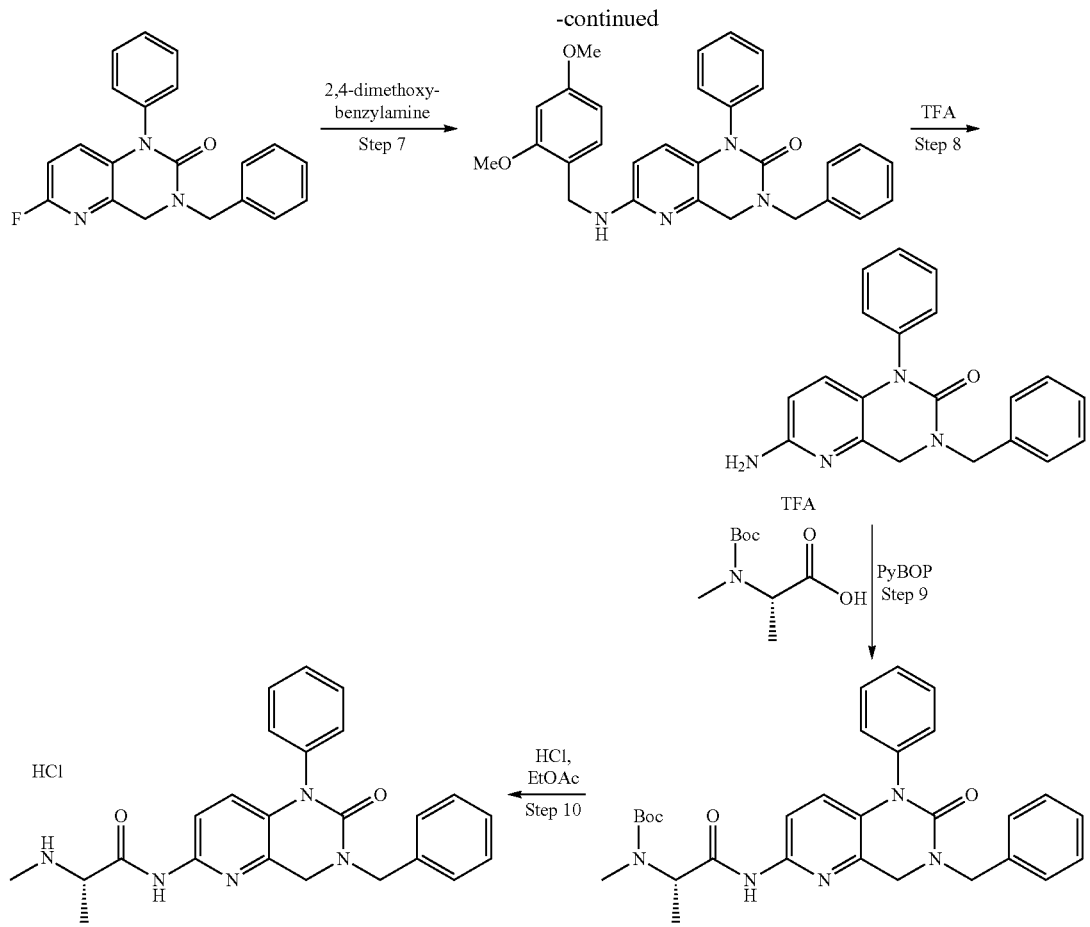

Step 1:

To a solution of 3-bromo-6-fluoro-2-methyl-pyridine (1.9 g, 10.0 mmol, 1.0 equiv) in CCl₄ (40 mL) was added N-bromo-succinimide (2.14 g, 12.0 mmol, 1.2 equiv) followed by 2,2'-azobis(2-methylpropionitrile) (0.16 g, 1.0 mmol, 0.1 equiv). The mixture was heated at reflux for 16 h, then left to stand at ambient temperature for 24 h. Water (100 mL) was added and the product was extracted with dichloromethane. The organic layer was washed with brine, dried (MgSO₄), filtered and concentrated under reduced pressure to afford 3-bromo-2-bromomethyl-6-fluoro-pyridine (2.7 g) which was used without further purification. 1H NMR (400 MHz, CDCl₃): 7.94 (1H, m), 7.84 (1H, m), 4.62 (2H, s).

Step 2:

To a solution of 3-bromo-2-bromomethyl-6-fluoro-pyridine (2.70 g, 10.0 mmol, 1.0 equiv) in dichloromethane (20 mL) was added a solution of 4-methoxybenzylamine (2.74 g, 20.0 mmol, 2.0 equiv) in dichloromethane (5 mL) and the reaction mixture was stirred at ambient temperature for 3 h. The reaction mixture was diluted with dichloromethane, washed with H₂O, dried (MgSO₄), filtered and concentrated under reduced pressure. The crude product was purified by column chromatography (SiO₂, eluted with petrol—EtOAc 0-50%) to afford (3-bromo-6-fluoro-pyridin-2-ylmethyl)-(4-methoxy-benzyl)-amine (1.2 g). MS: [M+H]⁺=326.

Step 3:

To a solution of (3-bromo-6-fluoro-pyridin-2-ylmethyl)-(4-methoxy-benzyl)-amine (637 mg, 2.0 mmol, 1.0 equiv) and N,N-diisopropylethylamine (700 µL, 4.0 mmol, 2.0 equiv) in dichloromethane (10 mL) was added phenyl isocyanate (260 µL, 2.4 mmol, 1.2 equiv) and the reaction mixture was stirred at ambient temperature for 2 h. The reaction mixture was diluted with dichloromethane, washed with H₂O, dried (MgSO₄), filtered and concentrated under reduced pressure. The crude product was purified by column chromatography (SiO₂, eluted with petrol—EtOAc 0-60%) to afford (1-(3-bromo-6-fluoro-pyridin-2-ylmethyl)-1-(4-methoxy-benzyl)-3-phenyl-urea (760 mg). MS: [M+H]⁺=445.

Step 4:

To a solution of (3-bromo-6-fluoro-pyridin-2-ylmethyl)-(4-methoxy-benzyl)-3-phenyl-urea (644 mg, 1.5 mmol, 1.0 equiv) and N,N-diisopropylethylamine (500 µL, 2.9 mmol, 2.0 equiv) in DMF (15 mL) was added CuI (331 mg, 1.7 mmol, 1.2 equiv) and the reaction mixture was heated at 150° C. for 5 h. The reaction mixture was cooled, H₂O was added and the product was extracted with EtOAc. The organic phase was washed with dilute NH₄OH, brine, dried (MgSO4), filtered and concentrated under reduced pressure. The crude product was purified by column chromatography (SiO₂, eluted with petrol—EtOAc 0-50%) to afford 6-fluoro-3-(4-methoxy-benzyl)-1-phenyl-3,4-dihydro-1H-pyrido[3,2-d]pyrimidin-2-one (300 mg). MS: [M+H]+=364.

Step 5:

6-Fluoro-3-(4-methoxy-benzyl)-1-phenyl-3,4-dihydro-1H-pyrido[3,2-d]pyrimidin-2-one (300 mg, 0.83 mmol) was deprotected according to the method of General procedure 1 (TFA deprotection). The free base was isolated and purified by column chromatography (SiO₂, eluted with petrol—

EtOAc 0-100%) to afford 6-fluoro-1-phenyl-3,4-dihydro-1H-pyrido[3,2-d]pyrimidin-2-one (120 mg). MS: [M+H]⁺=244.

Step 6:

To a solution of 6-fluoro-1-phenyl-3,4-dihydro-1H-pyrido[3,2-d]pyrimidin-2-one (120 mg, 0.5 mmol, 1.0 equiv) in DMF (3 mL) was added sodium hydride (60% in mineral oil, 24 mg, 0.6 mmol, 1.2 equiv) and the reaction mixture was stirred for 1 h. Benzyl bromide (70 µL, 0.6 mmol, 1.2 equiv) was added and the mixture was stirred for 16 h. H₂O was added and the product was extracted with EtOAc. The organic phase was washed with, brine, dried (MgSO₄), filtered and concentrated under reduced pressure. The crude product was purified by column chromatography (SiO₂, eluted with petrol—EtOAc 0-40%) to afford 3-benzyl-6-fluoro-1-phenyl-3,4-dihydro-1H-pyrido[3,2-d]pyrimidin-2-one (112 mg). MS: [M+H]⁺=334.

Step 7:

A mixture of 3-benzyl-6-fluoro-1-phenyl-3,4-dihydro-1H-pyrido[3,2-d]pyrimidin-2-one (112 mg, 0.34 mmol, 1.0 equiv) and 2,4-dimethoxybenzyl-amine (1.0 mL, 6.7 mmol, 20 equiv) was heated in the microwave reactor at 150° C. for 2 h. The crude reaction mixture was purified by column chromatography (SiO₂, eluted with petrol—EtOAc 0-50%) to afford 3-benzyl-6-(2,4-dimethoxy-benzylamino)-1-phenyl-3,4-dihydro-1H-pyrido[3,2-d]pyrimidin-2-one (66 mg). MS: [M+H]⁺=481.

Step 8-10:

Starting from 3-benzyl-6-(2,4-dimethoxy-benzylamino)-1-phenyl-3,4-dihydro-1H-pyrido[3,2-d]pyrimidin-2-one (64 mg, 0.13 mmol), Steps 8, 9 and 10 were performed by following methods similar to those described in General procedures 1, 4 and 3 respectively. This gave 19 mg of the title compound. 1H NMR (400 MHz, Me-d3-OD): 7.83 (1H, d), 7.65-7.47 (3H, m), 7.46-7.30 (7H, m), 6.61 (1H, d), 4.73 (2H, s), 4.53 (2H, s), 4.02-3.93 (1H, m), 2.72 (3H, s), 1.59 (3H, d). MS: [M+H]⁺=416.

Example 19

(S)-2-Methylamino-N-(2-oxo-1-phenyl-1,2,3,4-tetrahydro-pyrido[3,2-d]pyrimidin-6-yl)-propionamide hydrochloride

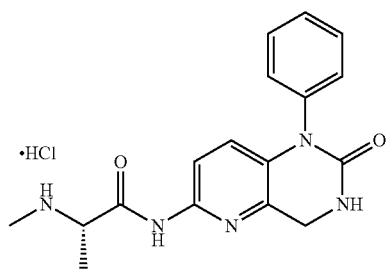 [SMILES: CN[C@@H](C)C(=O)Nc1ccc2c(n1)CNC(=O)N2c1ccccc1 ; Cl]

The compound was prepared using a similar procedure to Example 18 (Steps 1-4, then Steps 7-10) except that 2,4-dimethoxybenzyl-amine replaced 4-methoxybenzyl-amine in Step 2. 1H NMR (400 MHz, Me-d3-OD): 7.83 (1H, d), 7.63-7.45 (3H, m), 7.37-7.28 (2H, m), 6.62 (1H, d), 4.61 (2H, s), 4.01 (1H, q), 2.74 (3H, s), 1.62 (3H, d). MS: [M+H]⁺=326.

Example 20

(S)—N-(1,3-Dimethyl-2-oxo-1,2,3,4-tetrahydro-pyrido[3,2-d]pyrimidin-6-yl)-2-methylamino-propionamide hydrochloride

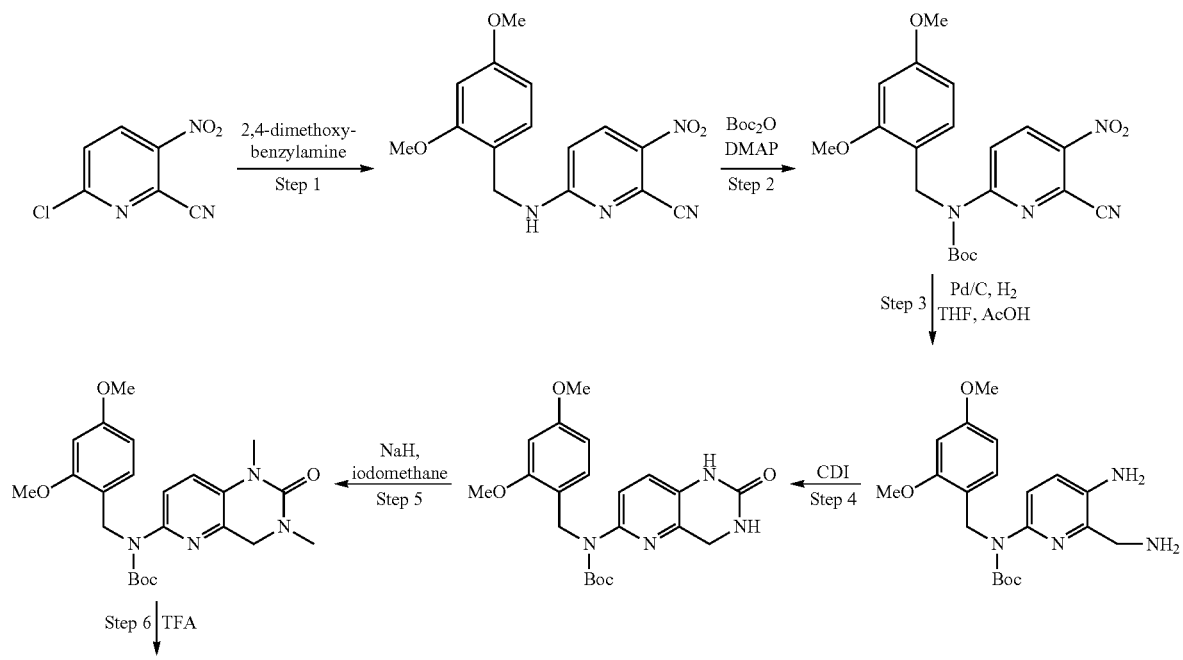

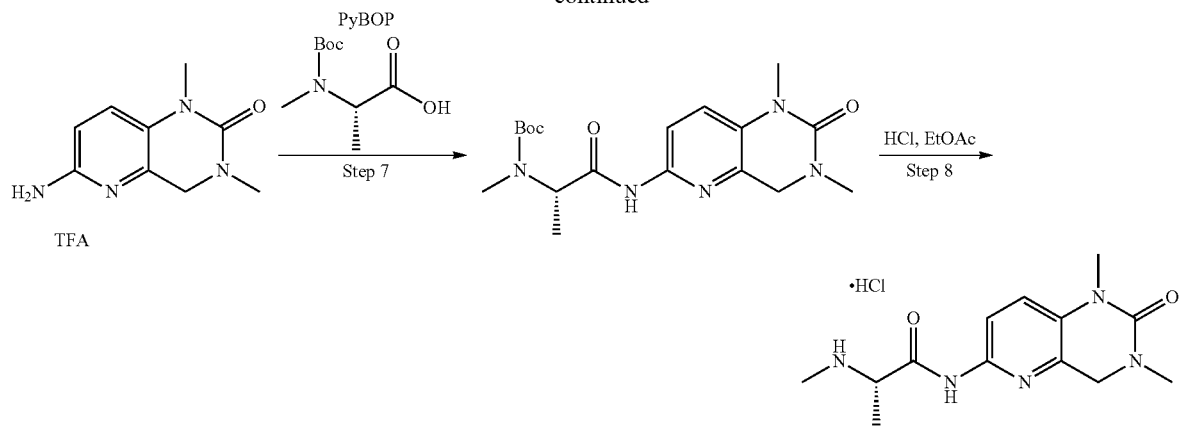

Step 1:

To an ice-cooled solution of 6-chloro-2-cyano-3-nitropyridine (52.0 g, 283 mmol) and triethylamine (43.0 mL, 425 mmol) in EtOH (950 mL) was added dropwise 2,4-dimethoxybenzylamine (53.2 mL, 312 mmol). The reaction was stirred at ambient temperature for 1.5 hours. The precipitate was filtered and washed with petrol to afford 75 g of 6-(2,4-dimethoxy-benzylamino)-3-nitro-pyridine-2-carbonitrile as a yellow solid. NMR $^1$H NMR (400 MHz, Me-d$_3$-OD): 8.19 (1H, d), 7.24 (1H, d), 6.77 (1H, d), 6.57 (1H, d), 6.49 (1H, dd), 4.56 (2H, s), 3.86 (3H, s), 3.80 (3H, s). MS: $[M+H]^+$=315.

Step 2:

To a solution of 6-(2,4-dimethoxy-benzylamino)-3-nitro-pyridine-2-carbonitrile (75.0 g, 239 mmol) in 1,4-dioxane (600 mL) was added Boc$_2$O (57 g, 262 mmol) in portions, and then the DMAP (1.5 g, 12 mmol), in a cold bath under N$_2$. The reaction mixture was stirred for 3 hours. The solvent was concentrated and water added. The aqueous layer was extracted with dichloromethane (×3). The combined organic layers were washed with brine, dried (MgSO$_4$), filtered and evaporated to dryness to leave (6-cyano-5-nitro-pyridin-2-yl)-(2,4-dimethoxy-benzyl)-carbamic acid tert-butyl ester (108 g) as a yellow/brown oil. NMR $^1$H NMR (400 MHz, Me-d$_3$-OD): 8.61 (1H, d), 8.37 (1H, d), 7.02 (1H, d), 6.52 (1H, d), 6.45 (1H, dd), 5.24 (2H, s), 3.78 (3H, s), 3.76 (3H, s), 1.48 (9H, s). MS: $[M-H]^-$=413.

Step 3:

To a solution of (6-cyano-5-nitro-pyridin-2-yl)-(2,4-dimethoxy-benzyl)-carbamic acid tert-butyl ester (1.06 g, 2.56 mmol) in THF (10 mL) and acetic acid (20 mL) was added Pd/C (10%, 200 mg) and the reaction mixture was hydrogenated overnight. The catalyst was filtered and the filtrate evaporated to afford (5-amino-6-aminomethyl-pyridin-2-yl)-(2,4-dimethoxy-benzyl)-carbamic acid tert-butyl ester (1.3 g) as the acetate salt, which was used without further purification. MS: $[M+H]^+$=389.

Step 4:

To a solution of (5-amino-6-aminomethyl-pyridin-2-yl)-(2,4-dimethoxy-benzyl)-carbamic acid tert-butyl ester acetate salt (1.3 g, 2.56 mmol) and N,N-diisopropylethylamine (890 µL, 5.12 mmol, 2 equiv) in THF (20 mL) was added a solution of 1,1'-carbonyldiimidazole (622 mg, 3.84 mmol, 1.5 equiv) and the reaction mixture was stirred overnight. The solvent was evaporated and the crude material was purified by column chromatography (SiO$_2$, eluted with petrol—EtOAc 50-100%) to afford (2,4-dimethoxy-benzyl)-(2-oxo-1,2,3,4-tetrahydro-pyrido[3,2-d]pyrimidin-6-yl)-carbamic acid tert-butyl ester (464 mg). MS: $[M+H]^+$=415

Step 5:

To a solution of (2,4-dimethoxy-benzyl)-(2-oxo-1,2,3,4-tetrahydro-pyrido[3,2-d]pyrimidin-6-yl)-carbamic acid tert-butyl ester (59 mg, 0.15 mmol, 1 equiv) in DMF (2 mL) was added NaH (60% in mineral oil, 15 mg, 0.38 mmol, 2.5 equiv) and the reaction mixture was stirred for 1 h. Iodomethane (28 µL, 0.45 mmol, 3 equiv) was added and the stirring was continued overnight. H$_2$O was added and the product was extracted with EtOAc. The organic phase was washed with brine, dried (MgSO$_4$), filtered and evaporated. The crude material was purified by column chromatography (SiO$_2$, eluted with petrol—EtOAc 0-100%) to afford (2,4-dimethoxy-benzyl)-(1,3-dimethyl-2-oxo-1,2,3,4-tetrahydro-pyrido[3,2-d]pyrimidin-6-yl)-carbamic acid tert-butyl ester (22 mg). MS: $[M+H]^+$=413.

Step 6-8:

Starting with (2,4-dimethoxy-benzyl)-(1,3-dimethyl-2-oxo-1,2,3,4-tetrahydro-pyrido[3,2-d]pyrimidin-6-yl)-carbamic acid tert-butyl ester (36 mg, 0.09 mmol), Steps 6, 7 and 8 were performed by following methods similar to those described in General procedures 1, 4 and 3 respectively. This gave 12 mg of the title compound. 1H NMR (400 MHz, Me-d3-OD): 8.06 (1H, d), 7.40 (1H, d), 4.49 (2H, s), 4.02 (1H, q), 3.29 (3H, s), 3.04 (3H, s), 2.76 (3H, s), 1.63 (3H, d). MS: $[M+H]^+$=278.

Example 21

(S)—N-[1,3-Bis-(4-chloro-phenyl)-2-oxo-1,2,3,4-tetrahydro-pyrido[3,2-d]pyrimidin-6-yl]-2-methylamino-propionamide hydrochloride

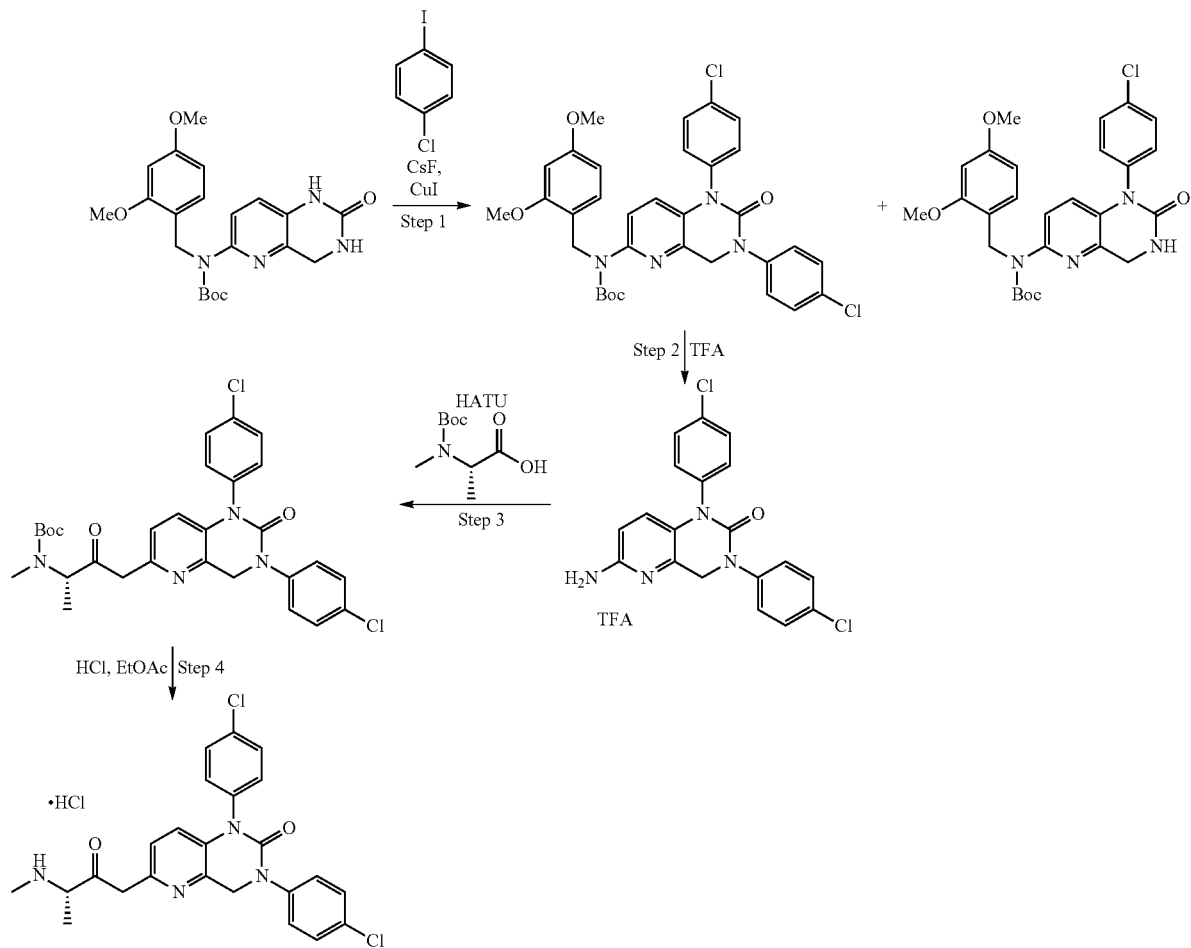

Step 1:

Into a reaction tube were placed CsF (1.0 g, 6.5 mmol, 2.5 equiv), CuI (50 mg, 0.26 mmol, 0.1 equiv), 1-chloro-4-iodobenzene (740 mg, 3.12 mmol, 1.2 equiv), (2,4-dimethoxy-benzyl)-(2-oxo-1,2,3,4-tetrahydro-pyrido[3,2-d]pyrimidin-6-yl)-carbamic acid tert-butyl ester (Example 20, product from Step 4) (1.09 g, 2.6 mmol, 1.0 equiv) and N,N'-dimethyl-ethylene diamine (280 µL, 2.6 mmol, 1.0 equiv). The tube was sealed, evacuated and back-filled with nitrogen, then acetonitrile (5 mL) was added and the reaction mixture was heated at 80° C. overnight. The reaction mixture was cooled, diluted with ethyl acetate and the reaction was quenched with saturated ammonium chloride. The products were extracted with ethyl acetate, the combined organics were washed with brine, dried (MgSO$_4$), filtered and the solvent evaporated. The crude material was purified by column chromatography (SiO$_2$, eluted with petrol—EtOAc 0-100%) to afford 490 mg of [1,3-bis-(4-chloro-phenyl)-2-oxo-1,2,3,4-tetrahydro-pyrido[3,2-d]pyrimidin-6-yl]-(2,4-dimethoxy-benzyl)-carbamic acid tert-butyl ester (high R$_F$ compound, MS: [M+H]$^+$=635) and 383 mg of [1-(4-chloro-phenyl)-2-oxo-1,2,3,4-tetrahydro-pyrido[3,2-d]pyrimidin-6-yl]-(2,4-dimethoxy-benzyl)-carbamic acid tert-butyl ester (low R$_F$ compound, MS: [M+H]$^+$=525).

Step 2-4:

Starting from [1,3-bis-(4-chloro-phenyl)-2-oxo-1,2,3,4-tetrahydro-pyrido[3,2-d]pyrimidin-6-yl]-(2,4-dimethoxy-benzyl)-carbamic acid tert-butyl ester, methods similar to described in General procedure 1-3 were used to obtain the title compound. 1H NMR (400 MHz, Me-d3-OD): 7.95 (1H, d), 7.64-7.55 (2H, m), 7.50-7.37 (6H, m), 6.76 (1H, d), 5.01 (2H, s), 4.02 (1H, d), 2.74 (3H, s), 1.62 (3H, d). MS: [M+H]$^+$=470.

Example 22

(S)—N-[1-(4-Chloro-phenyl)-2-oxo-1,2,3,4-tetrahydro-pyrido[3,2-d]pyrimidin-6-yl]-2-methylamino-propionamide hydrochloride

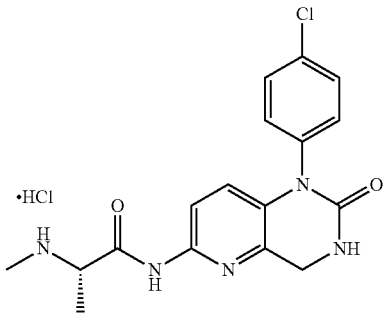 [SMILES: CN[C@@H](C)C(=O)Nc1ccc2c(n1)CNC(=O)N2c1ccc(Cl)cc1 ; Cl]

The compound was prepared according to Example 21 (Steps 1-4) except that the low R_F product [1-(4-chloro-phenyl)-2-oxo-1,2,3,4-tetrahydro-pyrido[3,2-d]pyrimidin-6-yl]-(2,4-dimethoxy-benzyl)-carbamic acid tert-butyl ester was used in an analogous procedure to Example 21 Step 2. 1H NMR (400 MHz, Me-d3-OD): 7.87 (1H, d), 7.63-7.53 (2H, m), 7.38-7.28 (2H, m), 6.67 (1H, d), 4.60 (2H, s), 4.01 (1H, q), 2.74 (3H, s), 1.62 (3H, d). MS: [M+H]⁺=360.

Example 23

(S)-2-Methylamino-N-(2-oxo-1,3-diphenyl-1,2,3,4-tetrahydro-pyrido[3,2-d]pyrimidin-6-yl)-propionamide hydrochloride

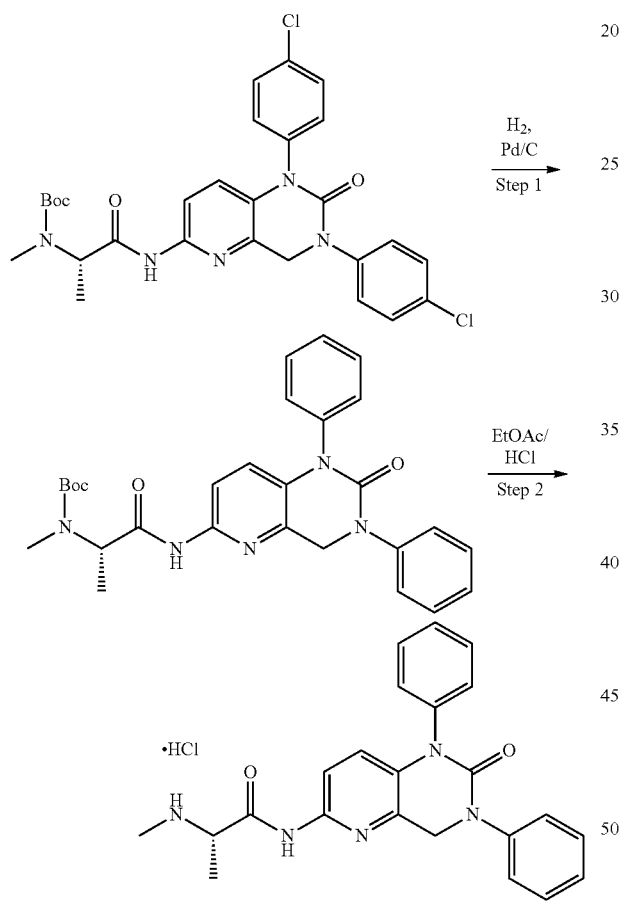

Step 1:

To a solution of {(S)-1-[1,3-bis-(4-chloro-phenyl)-2-oxo-1,2,3,4-tetrahydro-pyrido[3,2-d]pyrimidin-6-ylcarbamoyl]-ethyl}-methyl-carbamic acid tert-butyl ester (Example 21, product from Step 3) (100 mg, 0.18 mmol) in MeOH (10 mL) were added triethylamine (100 µL, 0.7 mmol, 4 equiv) and Pd/C (10%, 30 mg) and the mixture was hydrogenated overnight. The catalyst was filtered, the filtrate evaporated. The residue was dissolved in EtOAc and washed with H₂O. The organic phase was dried (MgSO₄), filtered and evaporated. The crude material was purified by column chromatography (SiO₂, eluted with petrol—EtOAc 0-60%) to afford methyl-[(S)-1-(2-oxo-1,3-diphenyl-1,2,3,4-tetrahydro-pyrido[3,2-d]pyrimidin-6-ylcarbamoyl)-ethyl]-carbamic acid tert-butyl ester (35 mg). MS: [M+H]⁺=502.

Step 2:

Methyl-[(S)-1-(2-oxo-1,3-diphenyl-1,2,3,4-tetrahydro-pyrido[3,2-d]pyrimidin-6-ylcarbamoyl)-ethyl]-carbamic acid tert-butyl ester (35 mg, 0.07 mmol) was treated with HCl according to the General procedure 3 to afford the title compound (28 mg). 1H NMR (400 MHz, Me-d3-OD): 7.91 (1H, d), 7.64-7.38 (9H, m), 7.38-7.28 (1H, m), 6.70 (1H, d), 5.03 (2H, s), 4.01 (1H, q), 2.74 (3H, s), 1.62 (3H, d). MS: [M+H]⁺=402.

Example 24

(S)—N-[1,3-Bis-(3-chloro-phenyl)-2-oxo-1,2,3,4-tetrahydro-pyrido[3,2-d]pyrimidin-6-yl]-2-methylamino-propionamide hydrochloride

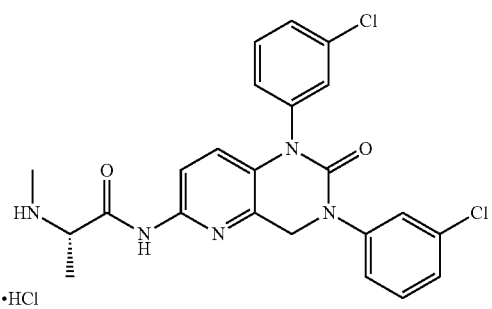 [SMILES: CN[C@@H](C)C(=O)Nc1ccc2c(n1)CN(c1cccc(Cl)c1)C(=O)N2c1cccc(Cl)c1 ; Cl]

The title compound was prepared by following methods similar to those described in Example 21 (Steps 1-4), except that 3-chloro-iodobenzene was used in Step 1 instead of 4-chloro-1-iodobenzene. 1H NMR (400 MHz, Me-d3-OD): 7.96 (1H, d), 7.63-7.29 (8H, m), 6.76 (1H, d), 5.03 (2H, s), 4.07-3.96 (1H, m), 2.75 (3H, s), 1.62 (3H, d). MS: [M+H]⁺=470.

Example 25

(S)—N-[1,3-Bis-(3,5-dichloro-phenyl)-2-oxo-1,2,3,4-tetrahydro-pyrido[3,2-d]pyrimidin-6-yl]-2-methylamino-propionamide hydrochloride

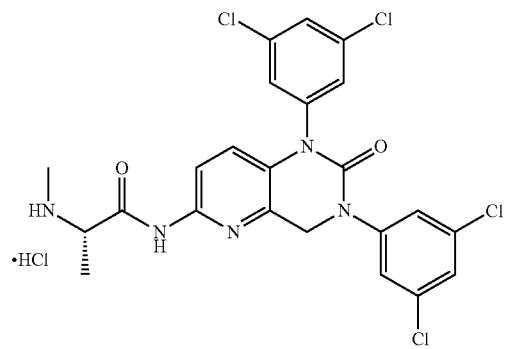 [SMILES: Cl ; CN[C@@H](C)C(=O)Nc1ccc2c(n1)CN(c1cc(Cl)cc(Cl)c1)C(=O)N2c1cc(Cl)cc(Cl)c1]

The title compound was prepared by following methods similar to those described in Example 21 (Steps 1-4), except that 3,5-dichloro-1-iodobenzene was used in Step 1 instead of 4-chloro-1-iodobenzene and HBTU replaced HATU in Step 3. 1HNMR (400 MHz, Me-d$_3$-OD): 7.99 (1H, d), 7.63 (1H, t), 7.52 (4H, dd), 7.40 (1H, t), 6.83 (1H, d), 5.02 (2H, s), 4.03 (1H, q), 2.75 (3H, s), 1.62 (3H, d). MS: [M+H]$^+$=538.

Example 26

(S)—N-[1-(4-Chloro-phenyl)-3-methyl-2-oxo-1,2,3,4-tetrahydro-pyrido[3,2-d]pyrimidin-6-yl]-2-methylamino-propionamide hydrochloride

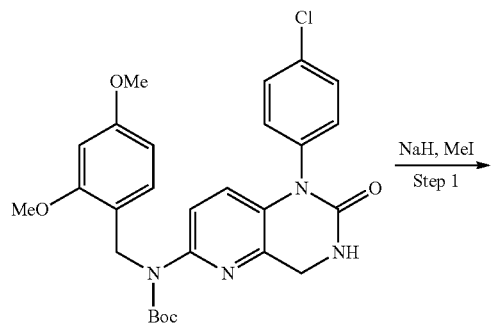

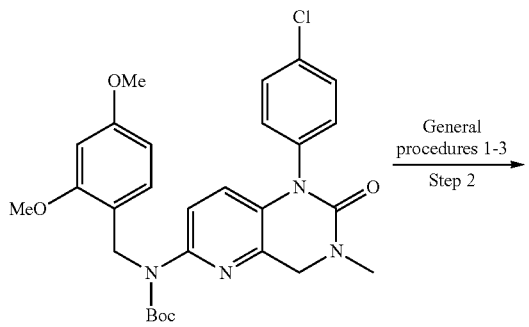

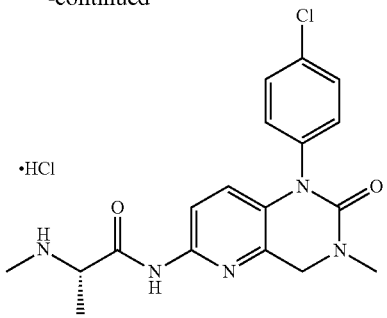

Step 1:

To a solution of [1-(4-chloro-phenyl)-2-oxo-1,2,3,4-tetrahydro-pyrido[3,2-d]pyrimidin-6-yl]-(2,4-dimethoxy-benzyl)-carbamic acid tert-butyl ester (Example 21, low R$_F$ compound from Step 1) (120 mg, 0.23 mmol) in DMF (3 mL) was added NaH (60% dispersion in oil, 14 mg, 0.34 mmol, 1.5 equiv) and the reaction mixture was stirred for 1 h. Iodomethane (30 μL, 0.46 mmol, 2 equiv) was added and stirring was continued overnight. Water was added and the product was extracted with EtOAc. The organic phase was washed with brine, dried (MgSO$_4$), filtered and the solvent evaporated. The crude material was purified by column chromatography (SiO$_2$, eluted with petrol—EtOAc 0-100%) to afford [1-(4-chloro-phenyl)-3-methyl-2-oxo-1,2,3,4-tetrahydro-pyrido[3,2-d]pyrimidin-6-yl]-(2,4-dimethoxy-benzyl)-carbamic acid tert-butyl ester (49 mg). MS: [M+H]$^+$=539.

Step 2:

Starting with [1-(4-chloro-phenyl)-3-methyl-2-oxo-1,2,3,4-tetrahydro-pyrido[3,2-d]pyrimidin-6-yl]-(2,4-dimethoxy-benzyl)-carbamic acid tert-butyl ester (49 mg, 0.09 mmol), methods similar to those described in General procedure 1-3 were used to obtain the title compound (12 mg). 1H NMR (400 MHz, Me-d3-OD): 7.87 (1H, d), 7.63-7.51 (2H, m), 7.46-7.26 (2H, m), 6.63 (1H, d), 4.65 (2H, s), 4.02 (1H, m), 3.08 (3H, s), 2.74 (3H, s), 1.62 (3H, d). MS: [M+H]$^+$=374.

Example 27

(S)—N-[3-(5-Chloro-2-fluoro-phenyl)-2-oxo-1-phenyl-1,2,3,4-tetrahydro-pyrido[3,2-d]pyrimidin-6-yl]-2-methylamino-propionamide hydrochloride

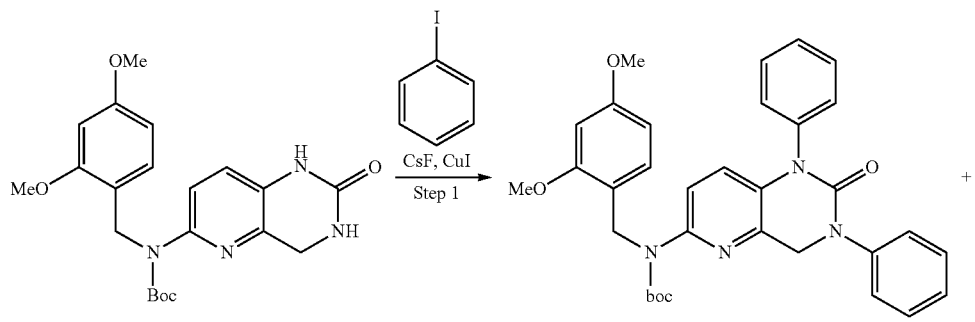

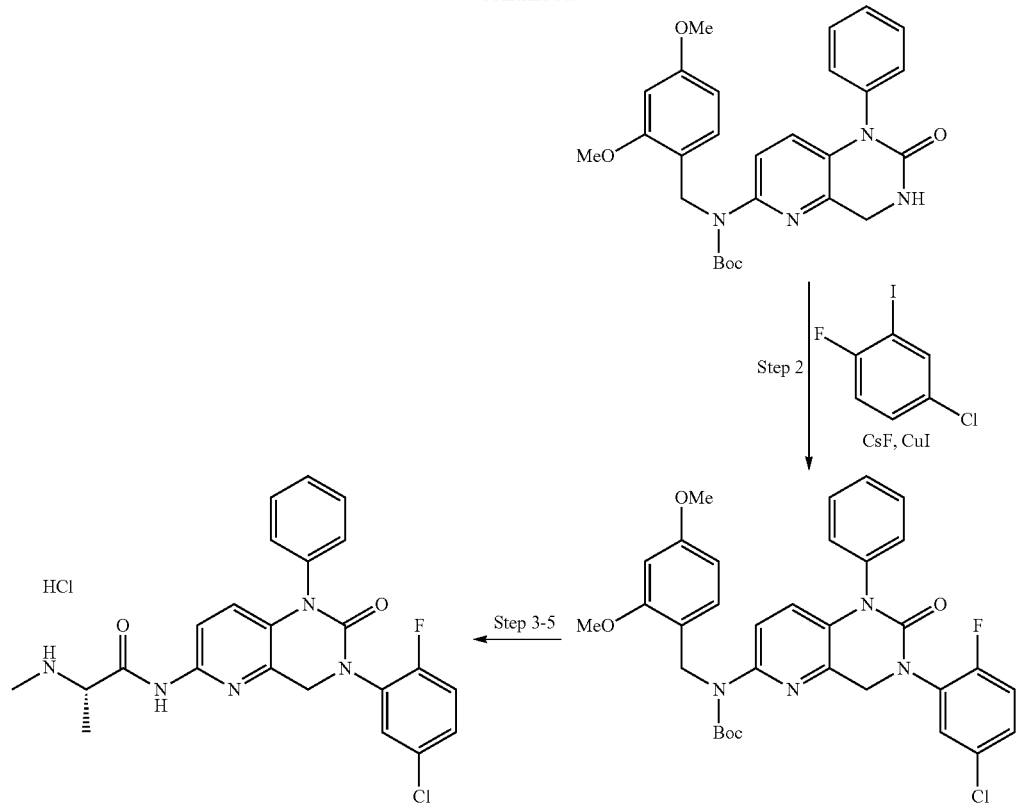

Step 1:

(2,4-Dimethoxy-benzyl)-(2-oxo-1,2,3,4-tetrahydro-pyrido[3,2-d]pyrimidin-6-yl)-carbamic acid tert-butyl ester (Example 20, product from Step 4) (1.09 g, 2.6 mmol, 1.0 equiv) was treated by following methods similar to those described in Example 21, Step 1 except that iodobenzene was used instead of 1-chloro-4-iodo-benzene to afford 420 mg of (2,4-dimethoxy-benzyl)-(2-oxo-1,3-diphenyl-1,2,3,4-tetrahydro-pyrido[3,2-d]pyrimidin-6-yl)-carbamic acid tert-butyl ester (MS: [M+H]⁺=567) and 358 mg of (2,4-dimethoxy-benzyl)-(2-oxo-1-phenyl-1,2,3,4-tetrahydro-pyrido[3,2-d]pyrimidin-6-yl)-carbamic acid tert-butyl ester. MS: [M+H]⁺=491.

Step 2:

(2,4-Dimethoxy-benzyl)-(2-oxo-1-phenyl-1,2,3,4-tetrahydro-pyrido[3,2-d]pyrimidin-6-yl)-carbamic acid tert-butyl ester (380 mg, 0.77 mmol) was treated according to the procedure of Example 21, Step 1, using 4-chloro-1-fluoro-2-iodo-benzene instead of 1-chloro-4-iodo-benzene to afford [3-(5-chloro-2-fluoro-phenyl)-2-oxo-1-phenyl-1,2,3,4-tetrahydro-pyrido[3,2-d]pyrimidin-6-yl]-(2,4-dimethoxy-benzyl)-carbamic acid tert-butyl ester (233 mg). MS: [M+H]⁺=619.

Step 3-5:

Starting with [3-(5-chloro-2-fluoro-phenyl)-2-oxo-1-phenyl-1,2,3,4-tetrahydro-pyrido[3,2-d]pyrimidin-6-yl]-(2,4-dimethoxy-benzyl)-carbamic acid tert-butyl ester (230 mg, 0.37 mmol), methods similar to those described in General procedures 1-3 were used to obtain the title compound (70 mg). 1H NMR (400 MHz, Me-d3-OD): 7.93 (1H, d), 7.69-7.48 (4H, m), 7.48-7.35 (3H, m), 7.28 (1H, t), 6.72 (1H, d), 4.98 (2H, s), 4.01 (1H, d), 2.74 (3H, s), 1.62 (3H, d). MS: [M+H]⁺=454.

Example 28

(S)-2-Methylamino-N-(2-oxo-1-phenyl-3-propyl-1,2,3,4-tetrahydro-pyrido[3,2-d]pyrimidin-6-yl)-propionamide hydrochloride

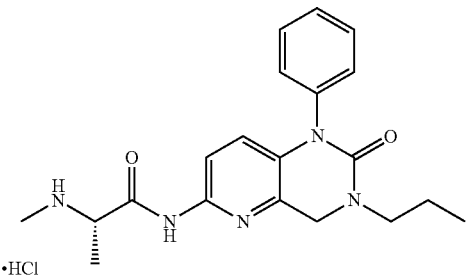 [SMILES: CCCN1Cc2nc(NC(=O)[C@H](C)NC)ccc2N(c2ccccc2)C1=O ; Cl]

The compound was prepared using similar method as described in Example 26 (Steps 1-2), except that (2,4-dimethoxy-benzyl)-(2-oxo-1-phenyl-1,2,3,4-tetrahydro-pyrido[3,2-d]pyrimidin-6-yl)-carbamic acid tert-butyl ester (Example 27, product from Step 1) and iodopropane were used in Step 1. 1H NMR (400 MHz, Me-d3-OD): 7.84 (1H, d), 7.63-7.45 (3H, m), 7.31 (2H, d), 6.58 (1H, d), 4.67 (2H, s), 4.07-3.95 (1H, m), 3.47 (2H, t), 2.74 (3H, s), 1.73 (2H, m), 1.62 (3H, d), 0.99 (3H, t). MS: [M+H]⁺=368

Example 29

(S)—N-[1-(4-Chloro-phenyl)-3-cyclohexyl-2-oxo-1,2,3,4-tetrahydro-pyrido[3,2-d]pyrimidin-6-yl]-2-methylamino-propionamide hydrochloride

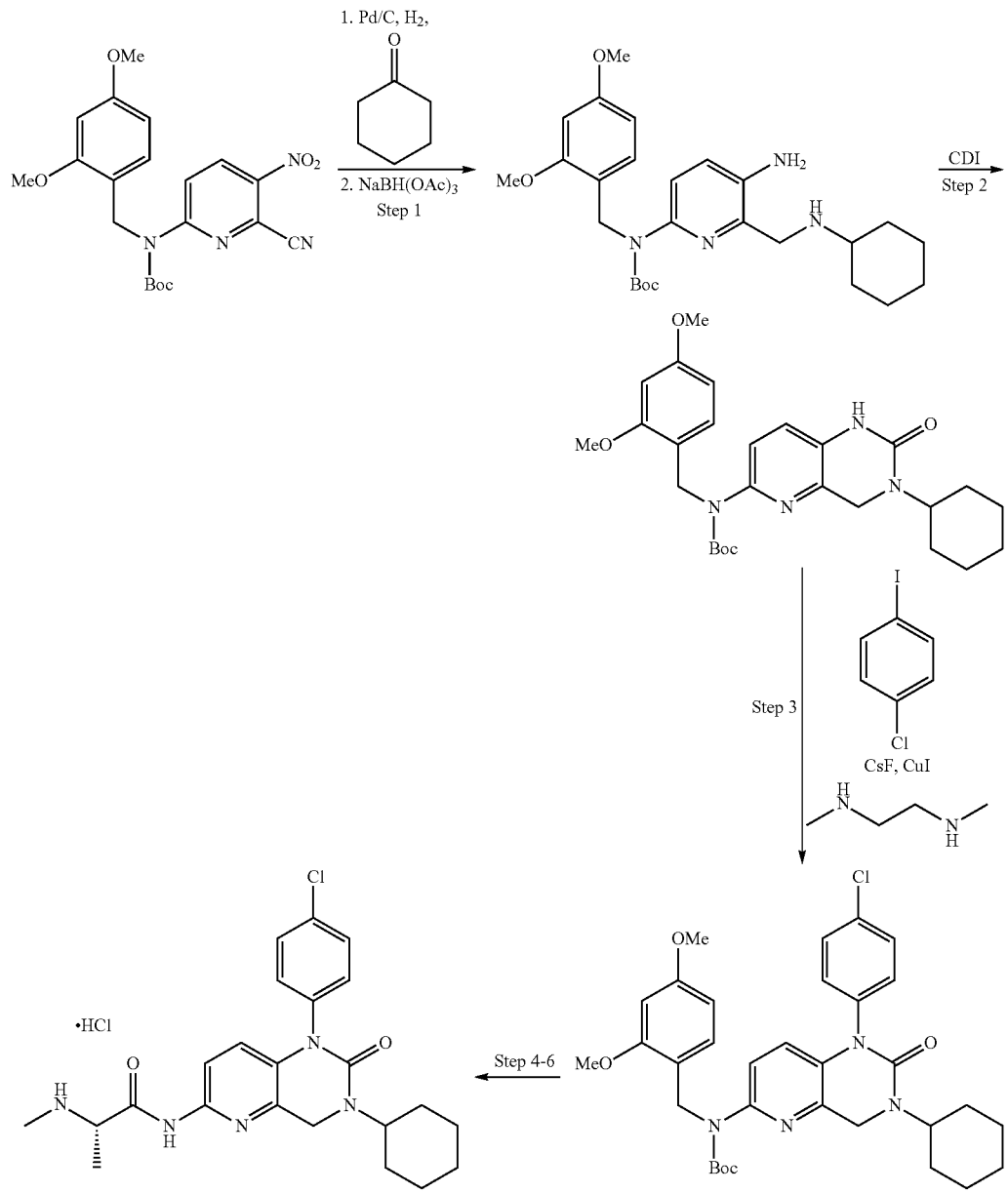

Step 1:

To a solution of (6-cyano-5-nitro-pyridin-2-yl)-(2,4-dimethoxy-benzyl)-carbamic acid tert-butyl ester Example 20 (Step 2) (1.10 g, 2.65 mmol, 1 equiv) and cyclohexanone (320 µL, 3.20 mmol, 1.2 equiv) in THF (10 mL) and acetic acid (20 mL), was added Pd/C (10%, 200 mg) and the reaction mixture was hydrogenated overnight. The catalyst was removed by filtration and the filtrate evaporated to give an oil. The oil was dissolved in DCE (15 mL) and treated with cyclohexanone (100 µL, 1.0 mmol) followed by sodium triacetoxyborohydride (954 mg, 4.5 mmol, 1.7 equiv). The reaction mixture was stirred at ambient temperature for 2 h, saturated NaHCO$_3$ was added and the product was extracted with dichloromethane. The organic phase was dried (MgSO$_4$), filtered and the solvent evaporated. The crude material was purified by column chromatography (SiO$_2$, eluted with dichloromethane—MeOH 0-10%) to afford (5-amino-6-cyclohexylaminomethyl-pyridin-2-yl)-(2,4-dimethoxy-benzyl)-carbamic acid tert-butyl ester (390 mg). MS: [M+H]$^+$=471.

Step 2:

To a solution of 1,1'-carbonyldiimidazole (162 mg, 1.0 mmol, 1.2 equiv) in THF (5 mL) was added a solution of (5-amino-6-cyclohexylaminomethyl-pyridin-2-yl)-(2,4-dimethoxy-benzyl)-carbamic acid tert-butyl ester (390 mg, 0.83 mmol, 1.0 equiv) in THF (5 mL) and the reaction mixture was stirred for 2 h. The solvent was evaporated, the residue was dissolved in EtOAc, washed with water, brine, dried (MgSO$_4$), filtered and the solvent was evaporated. The residue was crystallized from methanol to afford (3-cyclohexyl-2-oxo-1,2,3,4-tetrahydro-pyrido[3,2-d]pyrimidin-6-yl)-(2,4-dimethoxy-benzyl)-carbamic acid tert-butyl ester (282 mg) as a white solid. MS: [M+H]$^+$=496.

Step 3:

Into a reaction tube were placed CsF (211 mg, 1.4 mmol, 2.5 equiv), CuI (21 mg, 0.11 mmol, 0.2 equiv), 1-chloro-4-iodo-benzene (200 mg, 0.85 mmol, 1.5 equiv), (3-cyclohexyl-2-oxo-1,2,3,4-tetrahydro-pyrido[3,2-d]pyrimidin-6-yl)-(2,4-dimethoxy-benzyl)-carbamic acid tert-butyl ester (280 mg, 0.56 mmol, 1.0 equiv) and N,N'-dimethyl-ethylene diamine (60 μL, 0.56 mmol, 1.0 equiv). The tube was sealed, evacuated and back-filled with nitrogen 3 times, then THF (5 mL) was added and the reaction mixture was heated at 80° C. overnight. Further CuI (21 mg, 0.11 mmol, 0.2 equiv) and N,N'-dimethyl-ethylene diamine (30 μL, 0.28 mmol, 0.5 equiv) were added and the heating was continued for 24 h. The reaction mixture was cooled, diluted with EtOAc and the reaction was quenched with saturated ammonium chloride. The products were extracted with ethyl acetate, the combined organic extracts were washed with brine, dried (MgSO$_4$), filtered and the solvent evaporated. The crude material was purified by column chromatography (SiO$_2$, eluted with petrol—EtOAc 0-500%) to afford [1-(4-chloro-phenyl)-3-cyclohexyl-2-oxo-1,2,3,4-tetrahydro-pyrido[3,2-d]pyrimidin-6-yl]-(2,4-dimethoxy-benzyl)-carbamic acid tert-butyl ester (224 mg). MS: [M+H]$^+$=606.

Step 4-6:

Starting with [1-(4-chloro-phenyl)-3-cyclohexyl-2-oxo-1,2,3,4-tetrahydro-pyrido[3,2-d]pyrimidin-6-yl]-(2,4-dimethoxy-benzyl)-carbamic acid tert-butyl ester, methods similar to those described in General procedure 1-3 were used to obtain the title compound. 1H NMR (400 MHz, Me-d3-OD): 7.86 (1H, d), 7.63-7.52 (2H, m), 7.37-7.27 (2H, m), 6.63 (1H, d), 4.56 (2H, s), 4.32-4.19 (1H, m), 4.03 (1H, q), 2.74 (3H, s), 1.97-1.84 (2H, m), 1.84-1.65 (5H, m), 1.62 (3H, d), 1.59-1.14 (3H, m). MS: [M+H]$^+$=442.

The compounds in Table below, were prepared by following methods similar to those described for Example 29 above. All MS Data is [M+H]$^+$

| Eg. | Compound and Name | N.M.R. Data | M.S | Procedure |
|---|---|---|---|---|
| 30 | 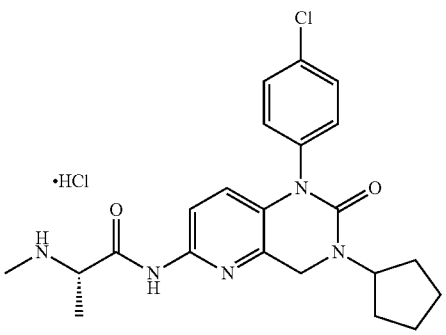 [SMILES: CN[C@@H](C)C(=O)Nc1ccc2c(n1)CN(C1CCCC1)C(=O)N2c1ccc(Cl)cc1 ; Cl]<br>(S)-N-[1-(4-Chloro-phenyl)-3-cyclopentyl-2-oxo-1,2,3,4-tetrahydro-pyrido[3,2-d]pyrimidin-6-yl]-2-methylamino-propionamide hydrochloride | 1H NMR (400 MHz, Me-d3-OD): 7.87 (1H, d), 7.63-7.52 (2H, m), 7.38-7.28 (2H, m), 6.64 (1H, d), 4.84-4.74 (1H, m), 4.56 (2H, s), 4.03 (1H, q), 2.75 (3H, s), 2.04-1.54 (11H, m). | 428 | Using cyclopentanone in Step 1 |
| 31 | 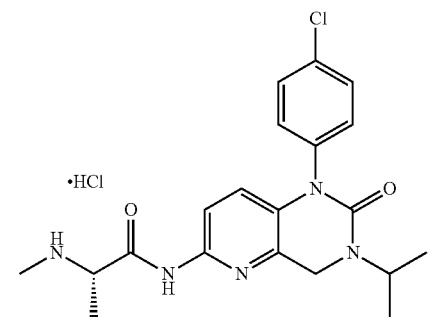 [SMILES: CN[C@@H](C)C(=O)Nc1ccc2c(n1)CN(C(C)C)C(=O)N2c1ccc(Cl)cc1 ; Cl]<br>(S)-N-[1-(4-Chloro-phenyl)-3-isopropyl-2-oxo-1,2,3,4-tetrahydro-pyrido[3,2-d]pyrimidin-6-yl]-2-methylamino-propionamide hydrochloride | 1H NMR (400 MHz, Me-d3-OD): 7.87 (1H, d), 7.62-7.53 (2H, m), 7.37-7.28 (2H, m), 6.64 (1H, d), 4.75-4.63 (1H, m), 4.53 (2H, s), 4.03 (1H, q), 2.75 (3H, s), 1.63 (3H, d), 1.30 (6H, d). | 402 | Using acetone in Step 1 |

| Eg. | Compound and Name | N.M.R. Data | M.S | Procedure |
|---|---|---|---|---|
| 32 | 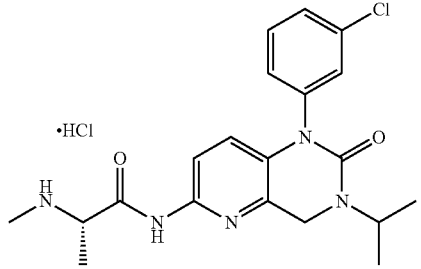 [SMILES: CN[C@@H](C)C(=O)Nc1ccc2c(n1)CN(C(C)C)C(=O)N2c1cccc(Cl)c1 ; Cl]<br>(S)-N-[1-(3-Chloro-phenyl)-3-isopropyl-2-oxo-1,2,3,4-tetrahydro-pyrido[3,2-d]pyrimidin-6-yl]-2-methylamino-propionamide hydrochloride | 1H NMR (400 MHz, Me-d3-OD): 7.88 (1H, d), 7.61-7.48 (2H, m), 7.41 (1H, t), 7.33-7.24 (1H, m), 6.64 (1H, d), 4.75-4.62 (1H, m), 4.54 (2H, s), 4.03 (1H, q), 2.75 (3H, s), 1.63 (3H, d), 1.30 (6H, d). | 402 | Using acetone in Step 1 and 3-chloro-1-iodo-benzene in step 3 |
| 33 | 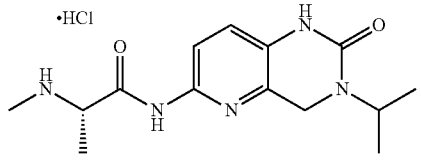<br>(S)-N-(3-Isopropyl-2-oxo-1,2,3,4-tetrahydro-pyrido[3,2-d]pyrimidin-6-yl)-2-methylamino-propionamide hydrochloride | 1H NMR (400 MHz, Me-d3-OD): 7.93 (1H, d), 7.20 (1H, d), 4.74-4.63 (1H, m), 4.41 (2H, s), 4.03 (1H, q), 2.76 (3H, s), 1.63 (3H, d), 1.25 (6H, d). | 292 | Using acetone in Step 1. Omitting Step 3 |
| 34 | 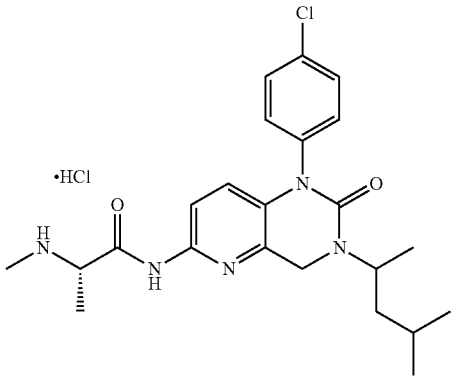 [SMILES: CN[C@@H](C)C(=O)Nc1ccc2c(n1)CN(C(C)CC(C)C)C(=O)N2c1ccc(Cl)cc1 ; Cl]<br>(S)-N-[1-(4-Chloro-phenyl)-3-(1,3-dimethyl-butyl)-2-oxo-1,2,3,4-tetrahydro-pyrido[3,2-d]pyrimidin-6-yl]-2-methylamino-propionamide hydrochloride | 1H NMR (400 MHz, Me-d3-OD): 7.88 (1H, d), 7.63-7.53 (2H, m), 7.37-7.28 (2H, m), 6.66 (1H, d), 4.73-4.61 (1H, m), 4.52 (1H, d), 4.42 (1H, dd), 4.02 (1H, q), 2.75 (3H, s), 1.75-1.59 (4H, m), 1.59-1.46 (1H, m), 1.44-1.29 (1H, m), 1.25 (3H, d), 0.94 (6H, d). | 444 | Using 4-methyl-2-pentanone in Step 1. Prepared as a mixture of 2 diastereoisomers |

| Eg. | Compound and Name | N.M.R. Data | M.S | Procedure |
|---|---|---|---|---|
| 35 | 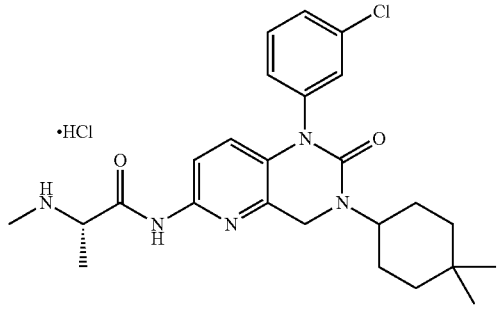<br><br>(S)-N-[1-(3-Chloro-phenyl)-3-(4,4-dimethyl-cyclohexyl)-2-oxo-1,2,3,4-tetrahydro-pyrido[3,2-d]pyrimidin-6-yl]-2-methylamino-propionamide hydrochloride | 1H NMR (400 MHz, Me-d3-OD): 7.87 (1H, d), 7.61-7.48 (2H, m), 7.45-7.37 (1H, m), 7.32-7.24 (1H, m), 6.64 (1H, d), 4.60 (2H, s), 4.24-4.12 (1H, m), 4.07-3.97 (1H, m), 2.75 (3H, s), 1.92 (2H, q), 1.67-1.48 (7H, m), 1.48-1.25 (2H, m), 1.00 (6H, d). | 470 | Using 4,4-dimethyl-cyclohexanone in Step 1 and 3-chloro-1-iodo-benzene in Step 3 |
| 36 | 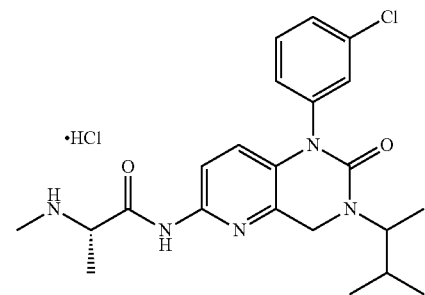<br><br>(S)-N-[1-(3-Chloro-phenyl)-3-(1,2-dimethyl-propyl)-2-oxo-1,2,3,4-tetrahydro-pyrido[3,2-d]pyrimidin-6-yl]-2-methylamino-propionamide hydrochloride | 1H NMR (400 MHz, Me-d3-OD): 7.89 (1H, d), 7.62-7.48 (2H, m), 7.41 (1H, t), 7.33-7.24 (1H, m), 6.66 (1H, d), 4.57 (1H, d), 4.44 (1H, d), 4.19-4.07 (1H, m), 4.03 (1H, q), 2.75 (3H, s), 1.99-1.86 (1H, m), 1.62 (3H, d), 1.32 (3H, d), 1.03 (3H, d), 0.93 (3H, d). | 430 | Using 3-methyl-butan-2-one in Step1 and 3-chloro-1-iodo-benzene in Step 3.<br>Prepared as a mixture of 2 diastereoisomers |
| 37 | 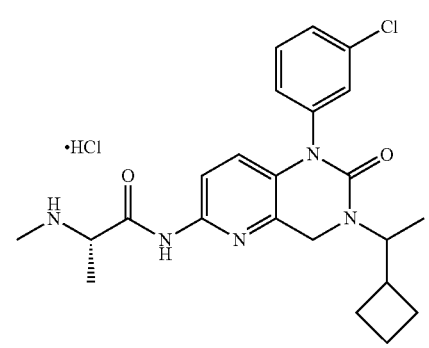 [SMILES: CN[C@@H](C)C(=O)Nc1ccc2c(n1)CN(C(C)C1CCC1)C(=O)N2c1cccc(Cl)c1 ; Cl]<br><br>(S)-N-[1-(3-Chloro-phenyl)-3-(1-cyclobutyl-ethyl)-2-oxo-1,2,3,4-tetrahydro-pyrido[3,2-d]pyrimidin-6-yl]-2-methylamino-propionamide hydrochloride | 1H NMR (400 MHz, Me-d3-OD): 7.87 (1H, d), 7.61-7.48 (2H, m), 7.41 (1H, t), 7.33-7.24 (1H, m), 6.64 (1H, d), 4.59-4.42 (2H, m), 4.37 (1H, d), 4.02 (1H, q), 2.75 (3H, s), 2.70-2.57 (1H, m), 2.24-2.11 (1H, m), 2.07-1.74 (5H, m), 1.63 (3H, d), 1.17 (3H, d). | 442 | Using 1-cyclobutyl-ethanone in Step1 and 3-chloro-1-iodo-benzene in Step 3.<br>Prepared as a mixture of 2 diastereoisomers |

| Eg. | Compound and Name | N.M.R. Data | M.S | Procedure |
|---|---|---|---|---|
| 38 | (S)-N-[3-(1-Acetyl-piperidin-4-yl)-1-(3-chloro-phenyl)-2-oxo-1,2,3,4-tetrahydro-pyrido[3,2-d]pyrimidin-6-yl]-2-methylamino-propionamide | 1H NMR NMR (400 MHz, Me-d3-OD): 7.89 (1H, d), 7.61-7.48 (2H, m), 7.42 (1H, t), 7.34-7.24 (1H, m), 6.63 (1H, d), 4.72 (1H, dd), 4.60-4.44 (3H, m), 4.08 (1H, d), 3.29-3.17 (2H, m), 2.78-2.64 (2H, m), 2.38 (3H, s), 2.16 (3H, s), 1.92-1.77 (3H, m), 1.33 (3H, d). | 485 | Using N-acetyl-4-piperidinone in Step1 and 3-chloro-1-iodo-benzene in Step 3 |
| 39 | (S)-N-[1-(3-Chloro-phenyl)-2-oxo-3-(1,3,3-trimethyl-butyl)-1,2,3,4-tetrahydro-pyrido[3,2-d]pyrimidin-6-yl]-2-methylamino-propionamide | 1H NMR (400 MHz, Me-d3-OD): 7.88 (1H, d), 7.62-7.48 (2H, m), 7.38 (1H, t), 7.31-7.22 (1H, m), 6.65 (1H, d), 4.82-4.71 (1H, m), 4.53 (2H, s), 4.03 (1H, q), 2.75 (3H, s), 1.87-1.74 (1H, m), 1.63 (3H, dd), 1.41-1.20 (4H, m), 0.94 (9H, d). | 458 | Using 4,4-dimethyl-pentan-2-one in Step1 and 3-chloro-1-iodo-benzene in Step 3. Prepared as a mixture of 2 diastereoisomers |

Example 40

(S)—N-[1-(4-Chloro-phenyl)-2-oxo-3-thiazol-4-ylmethyl-1,2,3,4-tetrahydro-pyrido[3,2-d]pyrimidin-6-yl]-2-methylamino-propionamide hydrochloride

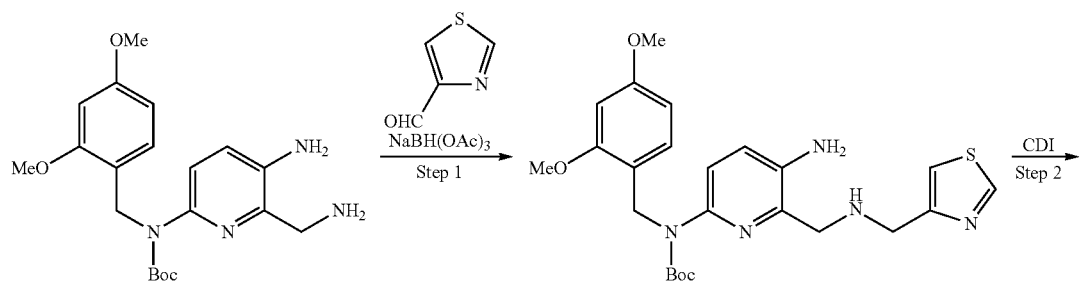

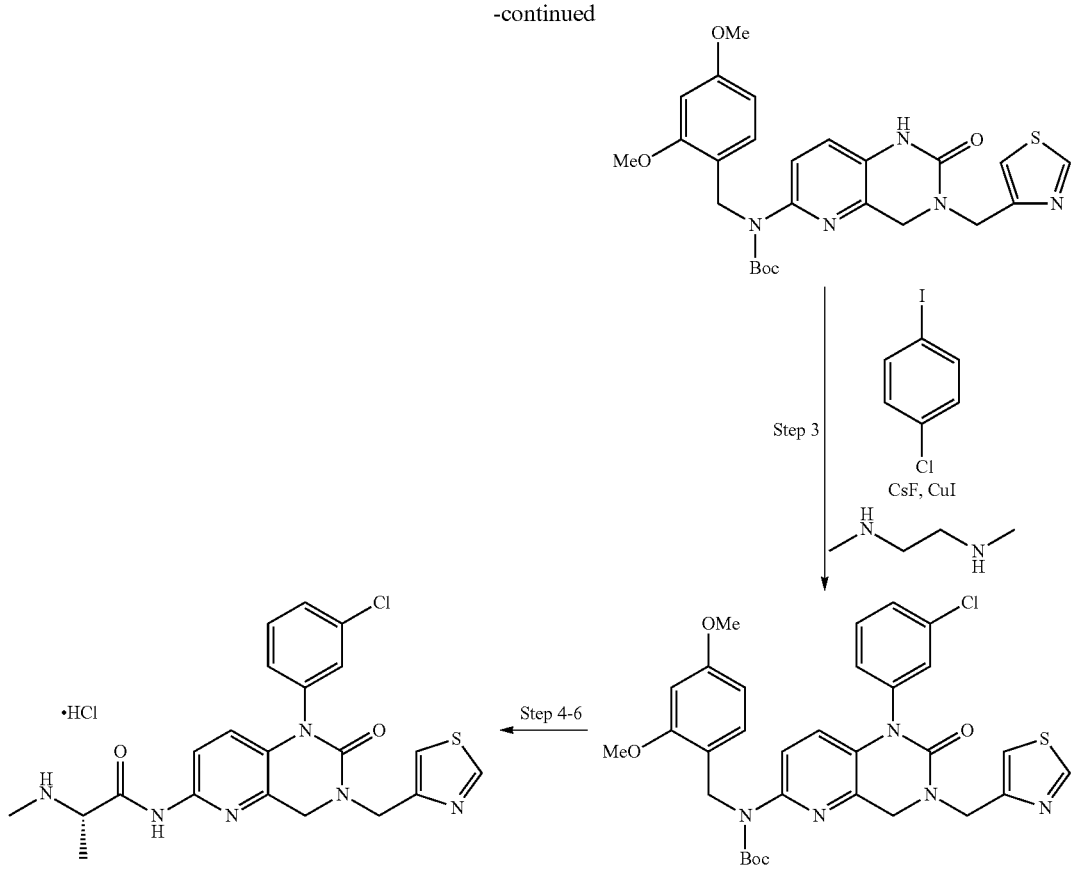

Step 1:

To a solution of (5-amino-6-aminomethyl-pyridin-2-yl)-(2,4-dimethoxy-benzyl)-carbamic acid tert-butyl ester (Example 20, product from Step 3) (422 mg, 1.1 mmol, 1 equiv), 1,3-thiazole-4-carbaldehyde (150 mg, 1.3 mmol, 1.2 equiv.) and acetic acid (32 µL, 2.2 mmol, 2 equiv) in DCE (5 mL) was added sodium triacetoxyborohydride (400 mg, 1.87 mmol, 1.7 equiv) and the reaction mixture was stirred for 16 h. Saturated NaHCO$_3$ was added and the product was extracted with dichloromethane. The organic phase was dried (MgSO$_4$), filtered and the solvent evaporated. The crude material was purified by column chromatography (SiO$_2$, eluted with dichloromethane—MeOH/NH$_3$ 0-10%) to afford (5-amino-6-{[(thiazol-4-ylmethyl)-amino]-methyl}-pyridin-2-yl)-(2,4-dimethoxy-benzyl)-carbamic acid tert-butyl ester (157 mg). MS: [M+H]$^+$=486.

Step 2-6:

(5-Amino-6-{[(thiazol-4-ylmethyl)-amino]-methyl}-pyridin-2-yl)-(2,4-dimethoxy-benzyl)-carbamic acid tert-butyl ester was converted to the title compound using similar procedure as described in Example 29, Steps 2-6, except that 3-chloro-1-iodo-benzene was used in Step 3, to afford the title compound. 1H NMR (400 MHz, Me-d3-OD): 9.29 (1H, d), 7.89 (1H, d), 7.77 (1H, s), 7.62-7.49 (2H, m), 7.46 (1H, d), 7.36-7.27 (1H, m), 6.66 (1H, d), 4.94-4.87 (2H, m), 4.72 (2H, s), 4.06-3.96 (1H, m), 2.73 (3H, s), 1.61 (3H, d). MS: [M+H]$^+$=457.

Example 41

(S)—N-[1-(4-Chloro-phenyl)-2-oxo-3-phenethyl-1,2,3,4-tetrahydro-pyrido[3,2-d]pyrimidin-6-yl]-2-methylamino-propionamide hydrochloride

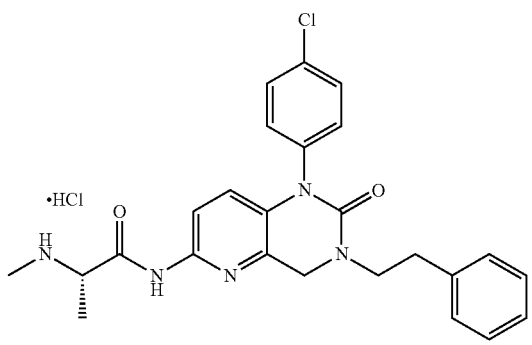 [SMILES: CN[C@@H](C)C(=O)Nc1ccc2c(n1)CN(CCc1ccccc1)C(=O)N2c1ccc(Cl)cc1 ; Cl]

The title compound was prepared by using similar methods to those described in Example 40 (Steps 1-6) except that phenylacetaldehyde was used in Step 1 and 4-chloro-1-iodo-benzene in Step 3. 1H NMR (400 MHz, Me-d3-OD): 7.87 (1H, d), 7.62-7.53 (2H, m), 7.37-7.28 (2H, m), 6.64 (1H, d), 4.75-4.63 (1H, m), 4.53 (2H, s), 4.03 (1H, q), 2.75 (3H, s), 1.63 (3H, d), 1.30 (6H, d). MS: [M+H]$^+$=464.

Example 42

(S)—N-[1-(3-Chloro-phenyl)-3-cyclopentylmethyl-2-oxo-1,2,3,4-tetrahydro-pyrido[3,2-d]pyrimidin-6-yl]-2-methylamino-propionamide hydrochloride

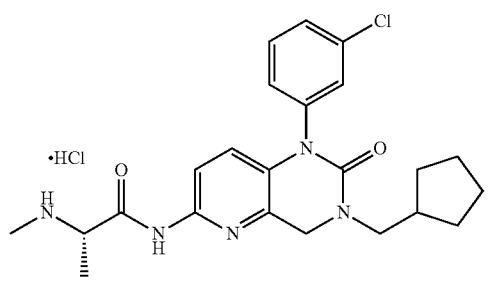 [SMILES: CN[C@@H](C)C(=O)Nc1ccc2c(n1)CN(CC1CCCC1)C(=O)N2c1cccc(Cl)c1 ; Cl]

The compound was prepared using methods similar to those described in Example 40 (Steps 1-6) except that cyclopentylaldehyde was used in Step 1. 1H NMR (400 MHz, Me-d3-OD): 7.88 (1H, d), 7.62-7.48 (2H, m), 7.40 (1H, t), 7.32-7.23 (1H, m), 6.64 (1H, d), 4.68 (2H, s), 4.07-3.97 (1H, m), 3.46 (2H, d), 2.74 (3H, s), 2.44-2.32 (1H, m), 1.87-1.52 (7H, m), 1.52-1.22 (4H, m). MS: [M+H]$^+$=442.

Example 43

N-(3-Benzyl-2-oxo-2,3-dihydro-1H-imidazo[4,5-b]pyridin-5-yl)-2-methylamino-propionamide hydrochloride

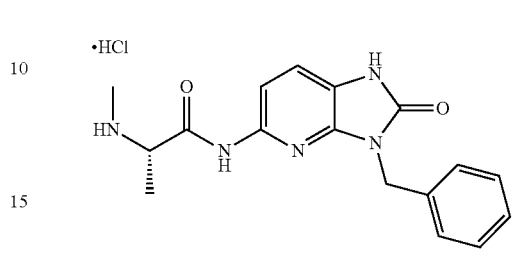

{1-[3-(4-Chloro-benzyl)-2-oxo-2,3-dihydro-1H-imidazo[4,5-b]pyridin-5-ylcarbamoyl]ethyl}-methyl-carbamic acid tert-butyl ester (100 mg, 0.22 mmol) (Example 1, product from Step 4) was dissolved in MeOH and stirred with Pd/C (50 mg) under hydrogen for 16 hours. The solution was filtered and evaporated in vacuo. Treatment with HCl (in an analogous fashion to General procedure 3) gave the title compound (38 mg) as a white solid. 1H NMR (400 MHz, DMSO-d6): 11.26 (1H, s), 10.86 (1H, s), 9.50 (1H, s), 9.03 (1H, s), 7.78 (1H, d), 7.42 (1H, d), 7.37-7.22 (5H, m), 5.01 (2H, s), 4.06-3.95 (1H, m), 2.55-2.52 (3H, m), 1.48 (3H, d). MS: [M+H]$^+$=326.

Example 44

(S)-2-Methylamino-N-(2-oxo-1,2,3,4-tetrahydro-pyrido[3,2-d]pyrimidin-6-yl)-propionamide hydrochloride

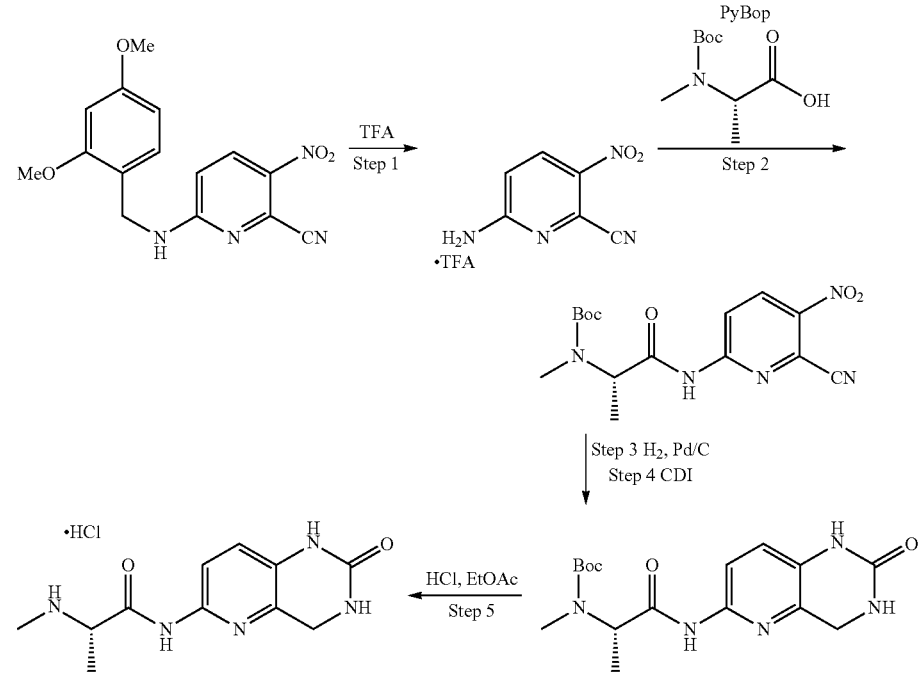

Step 1:

6-(2,4-Dimethoxy-benzylamino)-3-nitro-pyridine-2-carbonitrile (Example 20, product from Step 1) (700 mg, 2.23 mmol) was treated with TFA according to General procedure 1 to afford 6-amino-3-nitro-pyridine-2-carbonitrile as the trifluoroacetate salt (740 mg). MS: [M+H]$^+$=165.

Step 2:

The product from Step 1 was coupled with Boc-N-methyl-L-alanine according to General procedure 4 (but using dimethyl formamide instead of dichloromethane) to afford (S)-1-(6-cyano-5-nitro-pyridin-2-ylcarbamoyl)-ethyl]-methyl-carbamic acid tert-butyl ester. MS: [M–H]$^−$=348.

Step 3 and 4:

To a solution of (S)-1-(6-cyano-5-nitro-pyridin-2-ylcarbamoyl)-ethyl]-methyl-carbamic acid tert-butyl ester (400 mg, 1.15 mmol) in THF (15 mL) and acetic acid (10 mL) and MeOH (10 mL) was added Pd/C (10%, 100 mg) and the reaction mixture was hydrogenated for 2 hr. The catalyst was filtered and the filtrate evaporated. The residue was dissolved in THF (10 mL) and then treated with N,N-diisopropylethylamine (400 µL, 2.3 mmol, 2 equiv) and 1,1'-carbonyldiimidazole (186 mg, 1.15 mmol, 1.0 equiv). The reaction mixture was stirred for 1 hr. The solvent was evaporated and the crude material was purified by column chromatography (SiO$_2$, eluted with petrol—EtOAc 50-100%). The product was further purified by preparative LCMS to afford methyl-[(S)-1-(2-oxo-1,2,3,4-tetrahydro-pyrido[3,2-d]pyrimidin-6-ylcarbamoyl)-ethyl]-carbamic acid tert-butyl ester (62 mg). MS: [M+H]$^+$=350.

Step 5:

Methyl-[(S)-1-(2-oxo-1,2,3,4-tetrahydro-pyrido[3,2-d]pyrimidin-6-ylcarbamoyl)-ethyl]-carbamic acid tert-butyl ester (67 mg, 0.19 mmol) was treated with HCl according to the General procedure 3 to afford the title compound (27 mg).

1H NMR (400 MHz, Me-d3-OD): 1H NMR (400 MHz, Me-d3-OD): 7.94 (1H, d), 7.21 (1H, d), 4.49 (2H, s), 4.07-3.96 (1H, m), 2.76 (3H, s), 1.63 (3H, d). MS: [M+H]$^+$=250.

Example 45

(S)-2-Amino-N-[1-(4-chloro-phenyl)-3,3-diethyl-2-oxo-2,3-dihydro-1H-pyrido[2,3-b][1,4]oxazin-6-yl]-propionamide hydrochloride

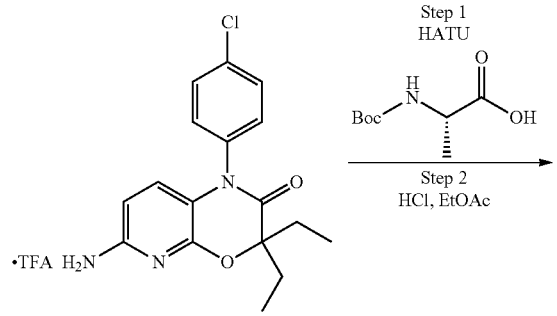

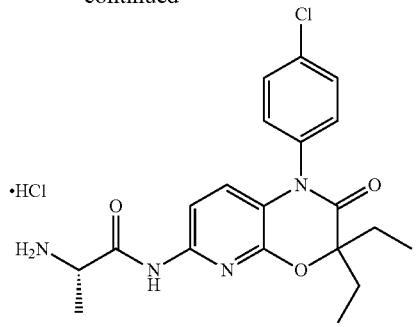

Step 1:

6-Amino-1-(4-chloro-phenyl)-3,3-diethyl-1H-pyrido[2,3-b][1,4]oxazin-2-one trifluoroacetate salt (Example 5, product from Step 3) (235 mg, 0.53 mmol) was coupled with N-(tert-butoxycarbonyl)-L-alanine (255 mg, 1.32 mmol) by following procedures similar to those described in General Procedure 2 to give {(S)-1-[1-(4-chloro-phenyl)-3,3-diethyl-2-oxo-2,3-dihydro-1H-pyrido[2,3-b][1,4]oxazin-6-ylcarbamoyl]-ethyl}-carbamic acid tert-butyl ester (177 mg) as a colourless gum. MS: [M+H]$^+$503.

Step 2 was performed by following a procedure similar to that described in General Procedure 3 to give the title compound as an off-white solid (100 mg). 1H NMR (400 MHz, Me-d3-OD): 7.75-7.56 (3H, m), 7.36-7.25 (2H, m), 6.78 (1H, d), 4.18-4.04 (1H, m), 2.17-2.08 (2H, m), 2.01-1.89 (2H, m), 1.60 (3H, d), 1.06 (6H, t). MS: [M+H]$^+$ 403.

Example 46

(S)-2-Amino-N-[1-(4-chloro-phenyl)-3,3-diethyl-2-oxo-2,3-dihydro-1H-pyrido[2,3-b][1,4]oxazin-6-yl]-propionamide (2,3,3,3-d$_4$) hydrochloride

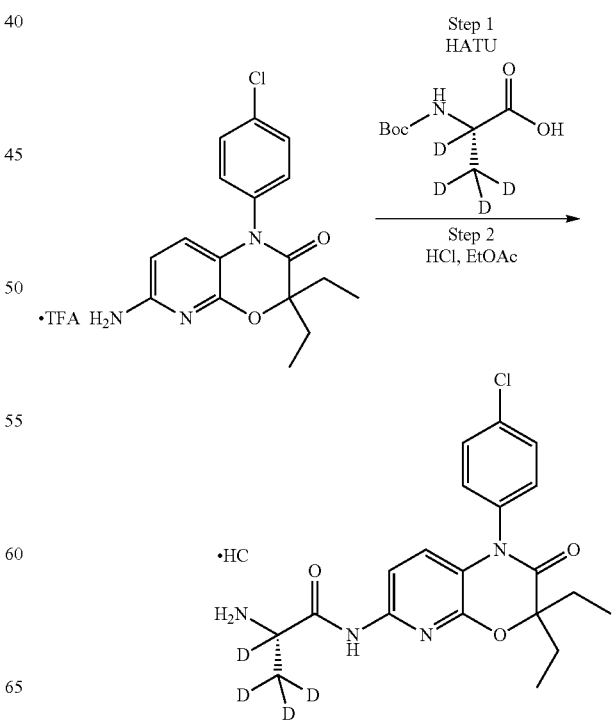

Example 2 was prepared by following procedures similar to those described in Example 1 or General Procedures 2 and 4, but using N-(tert-butoxycarbonyl)-L-alanine-(2,3,3,3-d$_4$) instead of N-(tert-butoxycarbonyl)-L-alanine. The title compound was obtained as a colourless solid (95 mg). 1H NMR (400 MHz, Me-d3-OD): 7.74-7.56 (3H, m), 7.36-7.25 (2H, m), 6.78 (1H, d), 2.19-2.02 (2H, m), 2.02-1.85 (2H, m), 1.06 (6H, t). MS: [M+H]$^+$ 407.

Biological Assays

Expression and Purification of XIAP, cIAP-1 and cIAP-2 BIR3 Domains

The recombinant BIR3 domain of human XIAP (residues 252-350) fused to a His-tag, human cIAP-1 (residues 267-363) fused to a GST-tag and human cIAP-2 (residues 244-337) fused to a His-tag were overexpressed from *Escherichia coli* cells grown in TB medium. Protein was isolated from lysates using Ni-NTA affinity chromatography (XIAP/cIAP-2) or glutathione sepharase 4B affinity chromatography (cIAP-1). Affinity tags for XIAP and cIAP-1 were cleaved with thrombin in 25 mM HEPES pH 7.5, 100 mM NaCl, 50 μM Zn(OAc)$_2$ and 1 mM Ca(OAc)$_2$ followed by purification of BIR3 domains by size-exclusion chromatography. The His-tag was uncleaved for cIAP-2 and the protein was not concentrated above 3 mg/ml due to aggregation induced covalent self-oligomerization issues. The purified protein was stored in 25 mM Tris pH 7.5, 100 mM NaCl at −80° C.

XIAP, cIAP-1 and cIAP-2 In Vitro Competitive Displacement Binding Assays

Modified SMAC peptides and compounds were tested for their ability to displace the fluorescent tracer from either XIAP, cIAP-1 or cIAP-2. BIR3 domains of cIAP-1, cIAP-2 and XIAP were incubated with test compounds or SMAC based peptides and their respective peptide probes (Peptide Protein Research) in assay buffer (50 mM Hepes pH 7.5, 0.025% Tween-20, 0.01% BSA, and 1 mM DTT). Positive controls consisted of BIR3 proteins and tracer (no inhibition) and negative controls contained tracer only (100% inhibition). The samples were incubated at room temperature for 1 hr (XIAP and cIAP-2) or 3 hrs (cIAP-1) prior to being read in the BMG Pherastar in Fluorescence Polarization mode (FP 485 nm, 520 nm, 520 nm). IC$_{50}$ values were determined from dose-response plots using nonlinear least-squares analysis.

Final Conditions for XIAP. cIAP-1 and cIAP-2 Assays

| Protein | Protein Conc | Peptide Probe | Peptide Conc |
|---|---|---|---|
| XIAP | 20 nM | AbuRPFK(5&6FAM)-amide | 5 nM |
| cIAP-1 | 4 nM | AbuRPFK(5&6FAM)-amide | 2 nM |
| cIAP-1 | 12 nM | AVPIK(5&6FAM)-amide | 2 nM |
| cIAP-2 | 20 nM | AVPWK(5&6FAM)-amide | 2 nM |

In the assays using XIAP and cIAP1, the compounds of Examples 2, 3, 4, 5, 6, 7, 8, 9, 10, 11, 12, 13, 14, 18, 19, 20, 21, 22, 23, 24, 25, 26, 27, 28, 29, 30, 31, 32, 33, 34, 35, 36, 37, 38, 39, 40, 41, 42, 45 and 46 have IC$_{50}$ values of less than 10 μM or provide at least 50% inhibition of the activity at a concentration of 10 μM in the assay against XIAP or cIAP1 whereas the compounds of Examples 2, 3, 4, 5, 6, 7, 8, 9, 10, 11, 12, 13, 14, 18, 19, 21, 22, 23, 24, 25, 26, 27, 28, 29, 30, 31, 32, 34, 35, 36, 37, 38, 39, 40, 41, 42, 45 and 46 have IC$_{50}$ values of less than 1 μM or provide at least 50% inhibition of the activity at a concentration of 1 μM in the assay against XIAP or cIAP1.

Preferred compounds of the invention have IC$_{50}$ values of less than 0.1 μM against XIAP and/or cIAP1 and or cIAP2.

Data for the compounds of the invention in the above assays are provided in Table A.

Examples 1, 4, 15, 16, 17, 18, 19, 20, 43 and 44 were tested in the cIAP1 assay using the AVPIK(5&6FAM)-amide probe (Probe A). The remaining compounds were tested in the cIAP1 assay using the AbuRPFK(5&6FAM)-amide probe (Probe B).

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours. At the end of the incubation period 10% (v/v) Alamar Blue is added and incubated for a further 6 hours prior to determination of fluorescent product at 535 nM ex/590 nM em.

The anti-proliferative activities of compounds of the invention can be determined by measuring the ability of the compounds to inhibit growth in 3 cancer cell lines:

EVSA-T (human breast carcinoma) DSMZ cat. no. ACC 433

MDA-MB-231 (human breast carcinoma) ECACC cat. no. 92020424

HCT116 (human colon carcinoma) ECACC cat. no. 91091005 (insensitive cell line used as a control for non-specific cytotoxicity)

Many compounds of the invention were found to have EC$_{50}$ values of less than 1 μM in EVSA-T cell line assays (and less than 10 μM against the MDA-MB-231 cell line) and preferred compounds have EC$_{50}$ values of less than 0.1 μM in EVSA-T cell assays (and less than 1 μM against the MDA-MB-231 cell line) and EC$_{50}$>10 μM against HCT116 cells.

In an assay using the EVSA-T cell line, Examples 2, 3, 5, 6, 7, 8, 9, 10, 11, 12, 13, 14, 21, 22, 23, 24, 25, 26, 27, 28, 29, 30, 31, 32, 34, 35, 36, 37, 38, 39, 40, 41, 45 and 46 have an EC$_{50}$ of less than 10 μM or greater than 50% at 10 μM.

Data for the compounds of the invention in the above assays are provided in Table A.

TABLE A

| Eg. No | IC$_{50}$ or PI Xiap (μM) | IC$_{50}$ or PI cIAP1 (μM) | EC$_{50}$ or PI EVSA-T prolif (μM) | Eg. No | IC$_{50}$ or PI Xiap (μM) | IC$_{50}$ or PI cIAP1 (μM) | EC$_{50}$ or PI EVSA-T prolif (μM) |
|---|---|---|---|---|---|---|---|
| 15 | 10-100 | 10-100 | nd | 5 | 0.01-1 | 0.01-1 | 0.089 |
| 17 | 10-100 | 10-100 | nd | 8 | 0.01-1 | 0.01-1 | 0.19 |
| 16 | 10-100 | 10-100 | nd | 34 | 0.01-1 | 0.01-1 | 0.24 |
| 20 | 10-100 | 1-10 | nd | 9 | 0.01-1 | 0.01-1 | 0.12 |
| 44 | 100-300 | 10-100 | nd | 35 | 0.01-1 | 0.01-1 | 0.65 |
| 18 | 1-10 | 0.1 | 0.86 | 10 | 0.01-1 | 0.01-1 | 0.092 |
| 4 | 1-10 | 0.01-1 | −13% at 10 | 3 | 0.01-1 | 0.01-1 | 0.28 |
| 1 | 28%@100 | 10%@30 | nd | 40 | 1-10 | 0.01-1 | 0.82 |

TABLE A-continued

| Eg. No | IC$_{50}$ or PI Xiap (μM) | IC$_{50}$ or PI cIAP1 (μM) | EC$_{50}$ or PI EVSA-T prolif (μM) | Eg. No | IC$_{50}$ or PI Xiap (μM) | IC$_{50}$ or PI cIAP1 (μM) | EC$_{50}$ or PI EVSA-T prolif (μM) |
|---|---|---|---|---|---|---|---|
| 19 | 1-10 | 0.01-1 | 3 | 36 | 0.01-1 | 0.01-1 | 0.88 |
| 21 | 0.01-1 | 0.01-1 | 0.91 | 7 | 0.01-1 | 0.01-1 | 0.44 |
| 22 | 1-10 | 0.01-1 | 0.69 | 11 | 0.01-1 | 0.01-1 | 0.11 |
| 23 | 0.01-1 | 0.01-1 | 1.4 | 12 | 0.01-1 | 0.01-1 | 0.11 |
| 24 | 0.01-1 | 0.01-1 | 0.36 | 13 | 0.01-1 | 0.01-1 | 0.17 |
| 26 | 0.01-1 | 0.01-1 | 1.6 | 37 | 0.01-1 | 0.01-1 | 0.62 |
| 2 | 1-10 | 0.01-1 | 0.54 | 42 | 0.01-1 | 0.01-1 | nd |
| 27 | 0.01-1 | 0.01-1 | 1.2 | 38 | 1-10 | 0.01-1 | 75% at 10 |
| 6 | 0.01-1 | 0.01-1 | 0.12 | 25 | 0.01-1 | 0.01-1 | 2.3 |
| 28 | 1-10 | 0.01-1 | 2.2 | 14 | 0.01-1 | 0.01-1 | 0.24 |
| 29 | 0.01-1 | 0.01-1 | 0.34 | 39 | 0.01-1 | 0.01-1 | 0.99 |
| 30 | 0.01-1 | 0.01-1 | 0.39 | 43 | 100-300 | 10-100 | nd |
| 31 | 0.01-1 | 0.01-1 | 0.49 | 45 | 0.01-1 | 0.01-1 | 2.9 |
| 41 | 1-10 | 0.01-1 | 2.5 | 46 | 0.01-1 | 0.01-1 | 7.4 |
| 32 | 0.01-1 | 0.01-1 | 1.6 | | | | |
| 33 | 1-10 | 1-10 | nd | | | | | nd—not determined

The enzyme data is represented by ranges to take account of inter-experimental variability. Where more than one data point has been obtained, the table above shows an average (e.g. geometric mean) of these data points (to 2 significant figures).

0.01-1 μM indicates that the compound has IC50 of between 0.01-1 μM or a Percentage Inhibition (PI) of greater than or approximately equal to 50% at a concentration of less than or approximately equal 1 μM. 1-10 μM indicates that the compound has IC50 of between 1-10 μM or a Percentage Inhibition (PI) of greater than or approximately equal to 50% at a concentration of less than or approximately equal to 10 μM. 10-100 μM indicates that the compound has IC50 of between 10-100 μM or a Percentage Inhibition (PI) of greater than or approximately equal to 50% at a concentration of less than or approximately equal to 100 μM. 100-300 μM indicates that the compound has IC50 of between 100-300 μM or a Percentage Inhibition (PI) of greater than or approximately equal to 50% at a concentration of less than or approximately equal to 300 μM.

The invention claimed is:

1. A compound of formula (I):

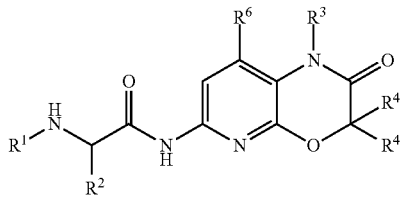

(I)

or a tautomeric or stereochemically isomeric form, N-oxide, pharmaceutically acceptable salt or solvate thereof; wherein $R^1$ is selected from hydrogen, $C_{1-6}$ alkyl, $C_{2-6}$ alkenyl, $C_{2-6}$ alkynyl, —$(CH_2)_s$—$C_{3-8}$ cycloalkyl and —$(CH_2)_s$—$C_{3-8}$ cycloalkenyl, wherein said $C_{1-6}$ alkyl, $C_{2-6}$ alkenyl, $C_{2-6}$ alkynyl, $C_{3-8}$ cycloalkyl and $C_{3-8}$ cycloalkenyl may be optionally substituted by one or more $R^a$ groups;

$R^a$ is selected from halogen, —OH and $C_{1-6}$ alkoxy;

$R^2$ is selected from hydrogen, $C_{1-4}$ alkyl, halo$C_{1-4}$ alkyl, $C_{2-4}$ alkenyl and —$(CH_2)_s$—$C_{3-8}$ cycloalkyl;

$R^3$ is selected from hydrogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —$(CH_2)_s$—CN, —$S(O)_q$—$R^x$, —C(=O)$R^x$, —C(=S)$R^x$, —C(=N)$R^x$, —$(CR^xR^y)_s$—C(=O)$OR^z$, —$(CR^xR^y)_s$—C(=O)$NR^xR^y$, —$(CR^xR^y)_s$—C(=S)$NR^z$, —$(CR^xR^y)_s$—C(=N)$NR^z$, and —$(CH_2)_s$—$SO_2NR^xR^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more $R^c$ groups;

$R^4$ and $R^{4'}$ are independently selected from hydrogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —$(CR^xR^y)_s$—O—$R^z$, —O—$(CR^xR^y)_n$—$OR^z$, —$(CH_2)_s$—CN, —$S(O)_q$—$R^x$, —C(=O)$R^x$, —C(=S)$R^x$, —C(=N)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—$NR^xC(=O)R^y$, —$(CH_2)_s$—OC(=O)$NR^xR^y$, —$(CH_2)_s$—$NR^xC(=O)OR^y$, —$(CH_2)_s$—$NR^xR^y$, —$NR^x$—$(CH_2)_s$—$R^z$, —$(CR^xR^y)_s$—C(=S)$NR^z$, —$(CR^xR^y)_s$—C(=N)$NR^z$, —$(CH_2)_s$—O—C(=O)—$C_{1-4}$alkyl-$NR^xR^y$, —$(CH_2)_s$—$NR^x$—$(CH_2)_s$—O—C(=O)—$R^z$, —$(CH_2)_s$—$NR^x$—$(CH_2)_s$—$SO_2$—$R^y$, —$(CH_2)_s$—NH—$SO_2$—$NR^xR^y$ and —$(CH_2)_s$—$SO_2NR^xR^y$ groups, or $R^4$ and $R^{4'}$ together with the carbon atom to which they are attached, can join to form a 3-10 membered carbocyclyl or heterocyclyl group, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more $R^c$ groups;

$R^6$ is selected from hydrogen, halogen, $C_{1-4}$ alkyl, halo$C_{1-4}$ alkyl, halo$C_{1-4}$ alkoxy and $C_{1-4}$alkoxy;

$R^b$ is independently selected from halogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, =O, =S, nitro, Si$(R^x)_4$, —$(CH_2)_s$—CN, —$S(O)_q$—$R^x$, —C(=O)$R^x$, —$(CR^xR^y)_s$—C(=O)$OR^z$, —$(CR^xR^y)_s$—O—C(=O)—$R^z$, —$(CR^xR^y)_s$—C(=O)$NR^xR^y$, —$(CH_2)_s$—$NR^xC(=O)R^y$, —$(CH_2)_s$—OC(=O)$NR^xR^y$, —$(CH_2)_s$—$NR^xC(=O)OR^y$, —$(CH_2)_s$—$NR^xR^y$, —NR$^x$—(CH$_2$)$_s$—R$^z$, —(CH$_2$)$_s$—O—C(=O)—C$_{1-4}$alkyl-NR$^x$R$^y$, —(CH$_2$)$_s$—NR$^x$—(CH$_2$)$_s$—O—C(=O)—R$^z$, —(CH$_2$)$_s$—NR$^x$—(CH$_2$)$_s$—SO$_2$—R$^y$, —(CH$_2$)$_s$—NH—SO$_2$—NR$^x$R$^y$, and —(CH$_2$)$_s$—SO$_2$NR$^x$R$^y$ groups, wherein said C$_{1-6}$ alkyl, C$_{2-6}$ alkenyl, C$_{2-6}$ alkynyl, C$_{3-8}$ cycloalkyl, C$_{3-8}$ cycloalkenyl and heterocyclyl groups may be optionally substituted by one or more RX groups;

R$^c$ is independently selected from halogen, C$_{1-6}$ alkyl, C$_{2-6}$ alkenyl, C$_{2-6}$ alkynyl, —(CH$_2$)$_s$—C$_{3-8}$ cycloalkyl, —(CH$_2$)$_s$—C$_{3-8}$ cycloalkenyl, —(CH$_2$)$_s$-phenyl, —(CH$_2$)$_s$-(4-7 membered saturated heterocyclyl), —(CR$^x$R$^y$)$_s$—O—R$^z$, —O—(CR$^x$R$^y$)$_s$—OR$^z$, haloC$_{1-6}$ alkyl, haloC$_{1-6}$ alkoxy, C$_{1-6}$ alkanol, =O, =S, nitro, Si(R$^x$)$_4$, —(CH$_2$)$_s$—CN, —S(O)$_q$—R$^x$, —C(=O)R$^x$, —(CR$^x$R$^y$)$_s$—C(=O)OR$^z$, —(CR$^x$R$^y$)$_s$—O—C(=O)—R$^z$, —(CR$^x$R$^y$)$_s$—C(=O)NR$^x$R$^y$, —(CH$_2$)$_s$—NR$^x$C(=O)R$^y$, —(CH$_2$)$_s$—OC(=O)NR$^x$R$^y$, —(CH$_2$)$_s$—NR$^x$C(=O)OR$^y$, —(CH$_2$)$_s$—NR$^x$R$^y$, —NR$^x$—(CH$_2$)$_s$—R$^z$, —(CH$_2$)$_s$—O—C(=O)—C$_{1-4}$alkyl-NR$^x$R$^y$, —(CH$_2$)$_s$—NR$^x$—(CH$_2$)$_s$—O—C(=O)—R$^z$, —(CH$_2$)$_s$—NR$^x$—(CH$_2$)$_s$—SO$_2$—R$^y$, —(CH$_2$)$_s$—NH—SO$_2$—NR$^x$R$^y$, —(CH$_2$)$_s$—SO$_2$NR$^x$R$^y$ and —P(=O)(R$^x$)$_2$ groups, wherein said C$_{1-6}$ alkyl, C$_{2-6}$ alkenyl, C$_{2-6}$ alkynyl, C$_{3-8}$ cycloalkyl, C$_{3-8}$ cycloalkenyl and heterocyclyl groups may be optionally substituted by one or more R$^x$ groups;

R$^x$, R$^y$ and R$^z$ independently represent hydrogen, C$_{1-6}$ alkyl, C$_{2-6}$ alkenyl, C$_{2-6}$ alkynyl, —(CH$_2$)$_s$—C$_{3-8}$ cycloalkyl, —(CH$_2$)$_s$—C$_{3-8}$ cycloalkenyl, —(CH$_2$)$_s$-(4-7 membered saturated heterocyclyl), C$_{1-6}$ alkanol optionally substituted with one or more halo, —C(=O)OC$_{1-6}$ alkyl, hydroxy, C$_{1-6}$ alkoxy, haloC$_{1-6}$ alkyl, —(CH$_2$)$_n$—O—C$_{1-6}$alkyl, —C(=O)—(CH$_2$)$_s$—C$_{1-6}$ alkoxy, —C(=O)—C$_{1-6}$alkyl, —(CH$_2$)$_s$—CN, C$_{1-6}$ alkyl-N(H)$_{2-q}$(C$_{1-6}$alkyl)$_q$, —N(H)$_{2-q}$(C$_{1-6}$alkyl)$_q$, —C(=O)—N(H)$_{2-q}$(C$_{1-6}$ alkyl)$_q$, —(CH$_2$)$_s$—NH—SO$_2$—N(H)$_{2-q}$(C$_{1-6}$ alkyl)$_q$, —(CH$_2$)$_s$—N(C$_{1-4}$ alkyl)-SO$_2$—N(H)$_{2-q}$(C$_{1-6}$ alkyl)$_q$ or —(CH$_2$)$_s$—O—C(=O)—C$_{1-4}$alkyl-N(H)$_{2-q}$(C$_{1-6}$ alkyl)$_q$, and when attached to nitrogen or carbon or phosphorus or silicon atom R$^x$ and R$^y$ may join to form a 3-7 membered ring optionally containing one or two additional heteroatoms selected from O, N, S and oxidised forms of N or S;

Y and Z are independently selected from a bond, —(CR$^x$R$^y$)$_m$—, —NR$^x$—, —C(=O)NR$^x$—, —NR$^x$C(=O)—, —(CR$^x$R$^y$)$_q$—O—, —O—(CR$^x$R$^y$)$_q$— and —S(O)$_q$—;

s independently represents an integer from 0-4;
n independently represents an integer from 1-4;
q represents an integer from 0-2;
m represents an integer from 1-2.

2. A compound according to claim 1 where R$^6$ is H, or a tautomeric or stereochemically isomeric form, N-oxide, pharmaceutically acceptable salt or solvate thereof.

3. A compound according to claim 1 wherein R$^1$ is unsubstituted methyl, or a tautomeric or stereochemically isomeric form, N-oxide, pharmaceutically acceptable salt or solvate thereof.

4. A compound according to claim 1 wherein R$^2$ is unsubstituted methyl, or a tautomeric or stereochemically isomeric form, N-oxide, pharmaceutically acceptable salt or solvate thereof.

5. A compound according to claim 1 wherein R$^3$ is selected from C$_{1-8}$ alkyl, —Y—C$_{3-12}$ carbocyclyl, and —Z-(3-12 membered heterocyclyl) groups, wherein said C$_{1-8}$ alkyl groups may be optionally substituted by one or more R$^b$ groups and wherein said carbocyclyl and heterocyclyl groups may be optionally substituted by one or more R$^c$ groups, or a tautomeric or stereochemically isomeric form, N-oxide, pharmaceutically acceptable salt or solvate thereof.

6. A compound according to claim 1 wherein R$^3$ is phenyl, wherein said phenyl group may be optionally substituted by one or more R$^c$ groups, or a tautomeric or stereochemically isomeric form, N-oxide, pharmaceutically acceptable salt or solvate thereof.

7. A compound according to claim 1 wherein R$^4$ and R$^{4'}$ are both C$_{1-6}$ alkyl, wherein said C$_{1-6}$ alkyl groups may be optionally substituted by one or more R$^b$ groups, or a tautomeric or stereochemically isomeric form, N-oxide, pharmaceutically acceptable salt or solvate thereof.

8. A compound according to claim 1 wherein R$^4$ and R$^{4'}$ together with the carbon atom to which they are attached, join to form a 3-6 membered non-aromatic carbocyclyl or join to form a 8-10 membered aromatic carbocyclyl group group, wherein said carbocyclyl group may be optionally substituted by one or more R$^c$ groups, or a tautomeric or stereochemically isomeric form, N-oxide, pharmaceutically acceptable salt or solvate thereof.

9. A compound as defined in claim 1 which is a compound of formula (Ic)

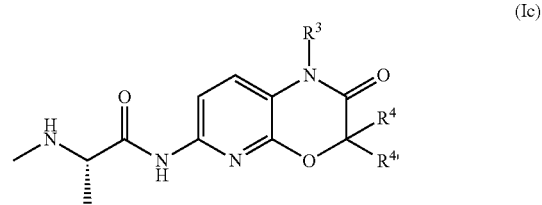

(Ic)

or a tautomeric or stereochemically isomeric form, N-oxide, pharmaceutically acceptable salt or solvate thereof.

10. A compound according to claim 1 selected from:
(S)—N-[1-(4-Chloro-phenyl)-2-oxo-2,3-dihydro-1H-pyrido[2,3-b][1,4]oxazin-6-yl]-2-methylamino-propionamide;
(S)—N—[(S)-1-(4-Chloro-phenyl)-3-methyl-2-oxo-3-phenyl-2,3-dihydro-1H-pyrido[2,3-b][1,4]oxazin-6-yl]-2-methylamino-propionamide;
(S)—N—((S)-3-Benzyl-2-oxo-2,3-dihydro-1H-pyrido[2,3-b][1,4]oxazin-6-yl)-2-methylamino-propionamide;
(S)—N-[1-(4-Chloro-phenyl)-3,3-diethyl-2-oxo-2,3-dihydro-1H-pyrido[2,3-b][1,4]oxazin-6-yl]-2-methylamino-propionamide;
(S)—N-[1-(4-Chloro-phenyl)-3,3-dimethyl-2-oxo-2,3-dihydro-1H-pyrido[2,3-b][1,4]oxazin-6-yl]-2-methylamino-propionamide;
(2S)—N-[4'-(4-Chlorophenyl)-3'-oxo-3',4'-dihydrospiro[cyclohexane-1,2'-pyrido[2,3-b][1,4]oxazine]-7'-yl]-2-(methylamino)propanamide;
(2S)—N-[4'-(4-Chlorophenyl)-3'-oxo-3',4'-dihydrospiro[cyclopentane-1,2'-pyrido[2,3-b][1,4]oxazine]-7'-yl]-2-(methylamino)propanamide;
(2S)—N-[4'-(4-Chlorophenyl)-3'-oxo-1,3,3',4'-tetrahydrospiro[indene-2,2'-pyrido[2,3-b][1,4]oxazine]-7'-yl]-2-(methylamino)propanamide;
(S)—N-[1-(3-Chloro-phenyl)-3,3-dimethyl-2-oxo-2,3-dihydro-1H-pyrido[2,3-b][1,4]oxazin-6-yl]-2-methylamino-propionamide;
(S)—N-[3-Benzyl-1-(3-chloro-phenyl)-3-methyl-2-oxo-2,3-dihydro-1H-pyrido[2,3-b][1,4]oxazin-6-yl]-2-methylamino-propionamide;

(S)—N-[1-(3-Chloro-phenyl)-3-isobutyl-3-methyl-2-oxo-2,3-dihydro-1H-pyrido[2,3-b][1,4]oxazin-6-yl]-2-methylamino-propionamide;
(S)—N-[1-(3-Chloro-phenyl)-3-cyclopentyl-3-methyl-2-oxo-2,3-dihydro-1H-pyrido[2,3-b][1,4]oxazin-6-yl]-2-methylamino-propionamide;
(S)-2-Methylamino-N-[3-methyl-3-(3-methyl-butyl)-2-oxo-1-phenyl-2,3-dihydro-1H-pyrido[2,3-b][1,4]oxazin-6-yl]-propionamide;
(S)-2-Amino-N-[1-(4-chloro-phenyl)-3,3-diethyl-2-oxo-2,3-dihydro-1H-pyrido[2,3-b][1,4]oxazin-6-yl]-propionamide hydrochloride; and
(S)-2-Amino-N-[1-(4-chloro-phenyl)-3,3-diethyl-2-oxo-2,3-dihydro-1H-pyrido[2,3-b][1,4]oxazin-6-yl]-propionamide (2,3,3,3-d4) hydrochloride;
or a tautomeric or stereochemically isomeric form, N-oxide, pharmaceutically acceptable salt or solvate thereof.

11. A pharmaceutical composition comprising a compound of formula (I) as defined in claim 1, or a tautomeric or stereochemically isomeric form, N-oxide, pharmaceutically acceptable salt or solvate thereof.

12. A pharmaceutical composition comprising a compound of formula (I) as defined in claim 1, or a tautomeric or stereochemically isomeric form, N-oxide, pharmaceutically acceptable salt or solvate thereof, in combination with one or more therapeutic agents.

13. A method for the treatment of cancer, wherein the cancer is mediated by an inhibitor of apoptosis (IAP), comprising administering to a subject in need thereof a compound as defined in claim 1, or a tautomeric or stereochemically isomeric form, N-oxide, pharmaceutically acceptable salt or solvate thereof.

14. A method for inhibiting binding of IAP protein, said method comprising contacting the IAP protein with a compound of formula (I) as defined in claim 1, or a tautomeric or stereochemically isomeric form, N-oxide, pharmaceutically acceptable salt or solvate thereof.

15. A process for preparing a compound of formula (I) as defined in claim 1, or a tautomeric or stereo chemically isomeric form, N-oxide, pharmaceutically acceptable salt or solvate thereof, which comprises:

(a) (i) reacting a compound of formula (II):

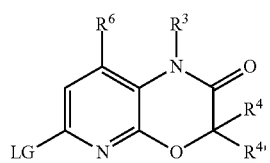

(II)

wherein LG represents a suitable leaving group such as a triflate group or halogen atom e.g. Cl, Br, I, with a compound of formula (III), for example using transition metal (e.g. Pd or Cu) couplings:

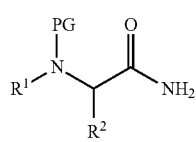

(III)

wherein PG represents a suitable protecting group such as a tert-butyloxycarbonyl (tBoc), followed by a deprotection reaction suitable to remove the PG protecting group; or (ii) reacting a compound of formula (IV):

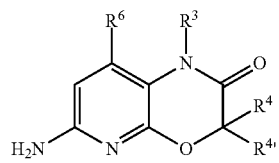

(IV)

with a compound of formula (V), for example using standard amide couplings:

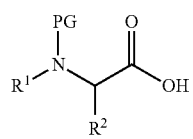

(V)

wherein PG represents a suitable protecting group such as a tert-butyloxycarbonyl (tBoc), followed by a deprotection reaction suitable to remove the PG protecting group; or (iii) compounds of formula (I) can be synthesised by reacting a compound of formula (VI):

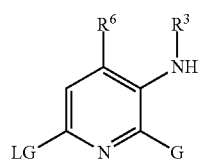

(VI)

wherein G is OH and LG represents a suitable leaving group such as a triflate group or halogen atom e.g. Cl, Br, I, with a compound of formula (III), for example using transition metal (Pd or Cu) metal couplings:

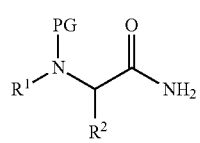

(III)

wherein PG represents a suitable protecting group such as a tert-butyloxycarbonyl (tBoc), followed by a deprotection reaction suitable to remove the PG protecting group, and then synthesising the second ring; or (iv) compounds of formula (I) can be synthesised by reacting a compound of formula (VII):

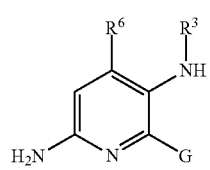

(VII)

wherein G is OH, with a compound of formula (V), for example using standard amide couplings:

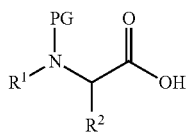

(V)

wherein PG represents a suitable protecting group such as a tert-butyloxycarbonyl (tBoc), followed by a deprotection reaction suitable to remove the PG protecting group, and then synthesising the second ring; and/or
(b) deprotection of a protected derivative of a compound of formula (I); and/or
(c) interconversion of a compound of formula (I) or protected derivative thereof to a further compound of formula (I) or protected derivative thereof; and
(d) optional formation of a pharmaceutically acceptable salt of a compound of formula (I).

16. A method according to claim 13, wherein the cancer is selected from a solid tumor, lymphoma, metastatic cancer, breast cancer, non-small cell lung carcinoma, pancreatic cancer, hepatocellular carcinoma, leukaemia, colorectal cancer, prostate cancer, ovarian cancer, peritoneum cancer, and melanoma.

17. A method according to claim 16, wherein the cancer is selected from chronic lymphocytic leukaemia (CLL), acute myeloid leukaemia (AML), and B-cell lymphoma.

18. A method according to claim 16, wherein the cancer is selected from breast cancer, non-small cell lung carcinoma, colorectal cancer, prostate cancer, acute myeloid leukaemia (AML), and melanoma.

* * * * *

UNITED STATES PATENT AND TRADEMARK OFFICE
CERTIFICATE OF CORRECTION

Page 1 of 1

PATENT NO.        : 9,155,743 B2
APPLICATION NO.   : 14/112581
DATED             : October 13, 2015
INVENTOR(S)       : Buck et al.

It is certified that error appears in the above-identified patent and that said Letters Patent is hereby corrected as shown below:

In the claims

Column 142, Line 18: Claim 8, Delete "group group" and insert --group--

Column 143, Line 39: Claim 15, Delete "stereo chemically" and insert --stereochemically--

Signed and Sealed this
Eighth Day of March, 2016

Michelle K. Lee
*Director of the United States Patent and Trademark Office*